US007972853B2

(12) United States Patent
Harrington et al.

(10) Patent No.: US 7,972,853 B2
(45) Date of Patent: Jul. 5, 2011

(54) COMPOSITIONS AND METHODS FOR MAKING MUTATIONS IN CELL LINES AND ANIMALS

(75) Inventors: John Joseph Harrington, Mentor, OH (US); Paul David Jackson, Shaker Heights, OH (US); Li Jiang, Hudson, OH (US)

(73) Assignee: ABT Holding Company, Cleveland, OH (US)

( * ) Notice: Subject to any disclaimer, the term of this patent is extended or adjusted under 35 U.S.C. 154(b) by 1624 days.

(21) Appl. No.: 10/345,115

(22) Filed: Jan. 15, 2003

(65) Prior Publication Data
US 2003/0224519 A1 Dec. 4, 2003

Related U.S. Application Data

(63) Continuation-in-part of application No. 10/277,612, filed on Oct. 22, 2002, which is a continuation-in-part of application No. 10/196,721, filed on Jul. 15, 2002, now abandoned.

(60) Provisional application No. 60/336,497, filed on Oct. 22, 2001.

(51) Int. Cl.
C12N 15/01 (2006.01)
C12N 15/00 (2006.01)
C07H 21/04 (2006.01)

(52) U.S. Cl. ........ 435/440; 435/455; 435/441; 435/446; 536/23.1

(58) Field of Classification Search .................. None
See application file for complete search history.

(56) References Cited

U.S. PATENT DOCUMENTS

| 6,436,707 | B1 | 8/2002 | Zambrowicz et al. | ........ 435/455 |
| 6,835,867 | B1 * | 12/2004 | Woychik et al. | ................. 800/21 |
| 2003/0143578 | A1 * | 7/2003 | Pruitt et al. | ........................ 435/6 |

FOREIGN PATENT DOCUMENTS

WO WO 96/39803 12/1996

OTHER PUBLICATIONS deWeese, T.L. et al. Mouse Embryonic Stem Cells Carrying One or Two Defective Msh2 Alleles Respond Abnormally to Oxidative Stress Inflicted by Low-level Radiation, PNAS 95:11915-11920, 1998.*
deWind, N. et al. Inactivation of the Mouse Msh2 Gene Results in Mismatch Repair Deficiency, Methylation Tolerance, Hyperrecombination, and Predisposition to Cancer, Cell 82:321-330, 1995.*
Amsterdam, A. et al. "A large-scale insertional mutagenesis screen in zebrafish," *Genes & Development* 13:2713-2724 (1999).
Brown, S.D.M. et al. "Mouse mutagenesis—systematic studies of mammalian gene function," *Human Molecular Genetics* 7(10):1627-33.

Chen, Y. et al. "Genotype-based screen of ENU-induced mutations in mouse embryonic stem cells" *Nat. Genet.* 24(3):314-7 (2000).
Friedberg, E.C et al. "Chapter 2: Introduction to Mutagenesis" in *DNA Repair and Mutagenesis*, pp. 59-90, ASM Press, Washington, D.C. (1995).
Friedberg, E.C et al. "Chapter 11: Mutagenesis in Prokaryotes" in *DNA Repair and Mutagenesis*, pp. 465-522, ASM Press, Washington, D.C. (1995).
Friedberg, E.C et al. "Chapter 12: DNA Damage Tolerance and Mutagenesis in Eukaryotic Cells" in *DNA Repair and Mutagenesis*, pp. 523-592, ASM Press, Washington, D.C. (1995).
Gogos, J.A. et al. "Selection for retroviral insertions into regulated genes" *Journal of Virology* 71(2):1644-50 (1997).
Hartwell, L.H. et al. "Integrating genetic approaches into the discovery of anticancer drugs" *Science* 278:1064-1068 (1997).
Rodriguez, C.I. et al. "High-efficiency deleter mice show that FLPe is an alternative to Cre-*loxP*" *Nat. Genet.* 25(2):139-40 (2000).
Soriano, P. et al. "Targeted disruption of the c-*src* proto-oncogene leads to osteopetrosis in mice" *Cell* 64:693-702 (1991).
Stark, G.R. et al. "Forward genetics in mammalian cells: functional approaches to gene discovery" *Human Molecular Genetics* 8(10):1925-38 (1999).
te Riele, H. et al. "Consecutive inactivation of both alleles of the *pim-1* proto-oncogene by homologous recombination in embryonic stem cells" *Nature* 348:649-651 (1990).
Voss, A.K. et al. "Efficiency assessment of the gene trap approach" *Developmental Dynamics* 212:171-180 (1998).
Cooley, Lynn et al., "Inertional Mutagenesis of the *Drosophila* Genome with Single P Elements" *Science*, 239(4844):1121-1128, 1988.
Bier, E., et al., "Searching for pattern and mutation in the *Drosophila* genome with a P- lacZ vector," *Genes & Development*, vol. 3:1273-1287 (1989).
Boeck, Ronald, et al., "Capped mRNA Degradation Intermediates Accumulate in the Yeast *spb8-2* Mutant," *Molecular and Cellular Biology*, vol. 18(9):5062-5072 (1998).
Gaiano, Nicholas, et al., "Insertional mutagenesis and rapid cloning of essential genes in zebrafish," *Nature*, vol. 383:829-832 (1996).
Gaiano, Nicholas, et al., "Highly efficient germ-line transmission of proviral insertions in zebrafish," *Proc. Natl. Acad. Sci.*, vol. 93:7777-7782 (1996).

(Continued)

*Primary Examiner* — Michele K Joike
(74) *Attorney, Agent, or Firm* — Tarolli, Sundheim, Covell & Tummino LLP

(57) ABSTRACT

The present invention is directed generally to reduction or inactivation of gene function or gene expression in cells in vitro and in multicellular organisms. The invention encompasses methods for mutating cells using a combination of mutagens, particularly wherein at least one mutagen is an insertional mutagen, to achieve homozygous gene mutation or mutation of multiple genes required cumulatively to achieve a phenotype to create knock-outs, knock-downs, and other modifications in the same cell. The invention is also directed to cells (and libraries thereof) and organisms created by the methods of the invention, including those in which at least one of the genes created by insertional mutagenesis is tagged by means of the insertion sequences thereby allowing identification of the mutated gene(s). The invention is also directed to libraries of mutated cells and their uses. The invention is also directed to methods of identifying mutations with methods of the invention, in cells (and libraries thereof) and organisms, by means of the insertional tag.

15 Claims, 21 Drawing Sheets

OTHER PUBLICATIONS

Figure 1A:
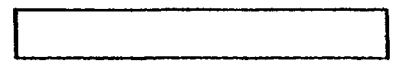
Figure 1B:
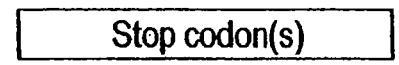
Figure 1C:
Figure 1D:
Figure 1E:
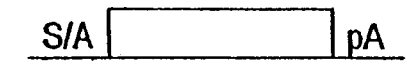
Figure 1F:
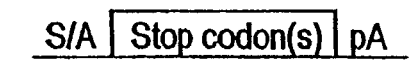
Figure 1G:
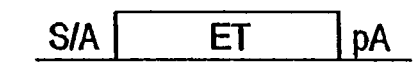
Figure 1H:
Figure 1I:
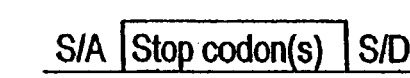
Figure 1J:
Figure 2A:
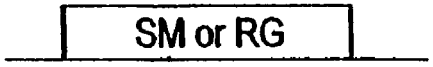
Figure 2B:
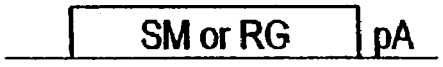
Figure 2C:
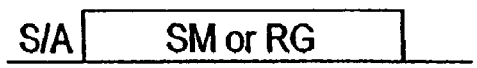
Figure 2D:
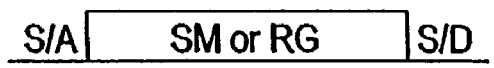
Figure 2E:
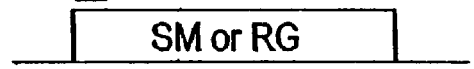
Figure 2F:
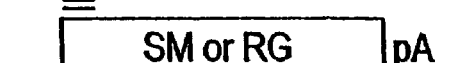
Figure 2G:
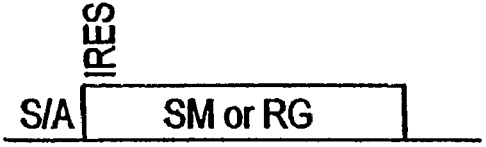
Figure 2H:
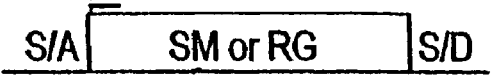

Harrington, John J., et al., "Creation of genome-wide protein expression libraries using random activation of gene expression," *Nature Biotechnology*, vol. 19:440-445 (2001).

Ibañez, Ester, et al., "Role of the *yiaR* and *yiaS* Genes of *Escherichia coli* in Metabolism of Endogenously Formed L-Xylulose," *Journal of Bacteriology*, vol. 182(16):4625-4627 (2000).

Krysan, Patrick J., et al., "T-DNA as an Insertional Mutagen in Arabidopsis," *The Plant Cell*, vol. 11:2283-2290 (1999).

Lee, Myeong S., et al., "Construction and Analysis of a Library for Random Insertional Mutagenesis in *Streptococcus pneumoniae*: Use for Recovery of Mutants Defective in Genetic Transformation and for Identification of Essential Genes," *Applied and Environmental Microbiology*, vol. 65(5):1883-1890 (1999).

Lobel, Leslie I, et al., "Construction of mutants of Moloney murine leukemia virus by suppressor-linker insertional mutagenesis: Positions of viable insertion mutations," *Proc. Natl. Acad. Sci.*, vol. 81:4149-4153 (1984).

Morrison, Paul T., et al., "Molecular Analysis of the *Escherichia coli recO* Gene," *Journal of Bacteriology*, vol. 171(7):3641-3649 (1989).

Morton, Daniel J., et al., "Effect of Multiple Mutations in the Hemoglobin- and Hemoglobin-Haptoglobin-Binding Proteins, HgpA, HgpB, and HgpC, of *Haemophilus influenzae* Type b," *Infection and Immunity*, vol. 67(6):2729-2739 (1999).

Ponce, Elizabeth, et al., "Cloning of the Two Pyruvate Kinase Isoenzyme Structural Genes from *Escherichia coli*: the Relative Roles of These Enzymes in Pyruvate Biosynthesis," *Journal of Bacteriology*, vol. 177(19):5719-5722 (1995).

Ueguchi, Chiharu, et al., "A Study of the Double Mutation of *dnaJ* and *cbpA*, Whose Gene Products Function as Molecular Chaperones in *Escherichia coli*," *Journal of Bacteriology*, vol. 177(13):3894-3896 (1995).

European Search Report Application No. 02776253.3-2406, dated Jan. 16, 2006.

* cited by examiner (C)

I

II

III

IV

# COMPOSITIONS AND METHODS FOR MAKING MUTATIONS IN CELL LINES AND ANIMALS

CROSS-REFERENCE TO RELATED APPLICATIONS

This application is a continuation-in-part of U.S. patent application No. 10/277,612, filed on Oct. 22, 2002, which is a continuation-in-part of U.S. patent application Ser. No. 10/196,721, filed on Jul. 15, 2002 now abandoned, which claims the benefit of U.S. Provisional Appl. No. 60/336,497 filed Oct. 22, 2001, the entire disclosures of which are incorporated herein by reference.

STATEMENT REGARDING FEDERALLY-SPONSORED RESEARCH AND DEVELOPMENT

Not applicable.

REFERENCE TO MICROFICHE APPENDIX/SEQUENCE LISTING/TABLE/COMPUTER PROGRAM LISTING APPENDIX

Not applicable.

BACKGROUND OF THE INVENTION

1. Field of the Invention

The present invention is in the fields of molecular biology, cell biology, and genetics. The invention is directed generally to mutating genes in cells in vitro and in multi-cellular organisms. The invention encompasses methods for mutating genes in cells using a combination of mutagens, wherein at least one mutagen is a polynucleotide that acts as an insertional mutagen. Such methods are used to achieve mutation of a single gene to achieve a desired phenotype as well as mutation of multi-cellular organism. The invention is also directed to methods of identifying one or more mutated genes, made by the methods of the invention, in cells and in multi-cellular organisms, by means of a tagging property provided by the insertional mutagen(s). The insertional mutagen thus allows identification of one or more genes that are mutated by insertion of the insertional mutagen.

The invention is also directed to cells and multi-cellular organisms created by the methods of the invention and uses of the cells and multicellular organisms. The invention is also directed to libraries of cells created by the methods of the invention and uses of the libraries.

2. Background

Mutagenesis has been used to identify the function of a large and growing number of genes. Mutation of one or more genes in a multi-cellular organism or cell allows the artisan to study the mutant organism or cell and compare it to the non-mutagenized (which may be wildtype) parent organism or cell. By identifying phenotypes associated with the mutant organism or cell, the function of the mutated gene(s) can be ascertained. Furthermore, mutagenesis provides a means for altering the genetic make up of a cell or multi-cellular organism to obtain a desired result. For example, it may be desirable to create a physiological disorder in a eukaryotic organism by mutating one more genes and then to identify one or more of the relevant genes. Thus, mutations that have a desired use (e.g., for commercial production of proteins, foodstuffs, or pharmaceuticals, or for production of transgenic animals as models of certain diseases) can be identified and selected. The possibilities for use of this technology, whether in vitro, ex vivo, or in vivo, are well known in the art.

Identification of novel genes and characterization of their function using mutagenesis has also been shown to be productive in identifying new drugs and drug targets. Creating in vitro cellular models that exhibit phenotypes that are clinically relevant provides a valuable substrate for target identification and screening for compounds that modulate not only the phenotype but also the target(s) that controls the phenotype. Modulation of such a target can provide information that validates the target as important for therapeutic intervention in a clinical disorder when such modulation of the target serves to modulate a clinically relevant phenotype.

Animal models exhibiting clinically relevant phenotypes are also valuable for drug discovery and development and for drug target identification. For example, mutation of somatic or germ cells facilitates the production of genetically modified offspring or cloned animals having a phenotype of interest. Such animals have a number of uses, for example as models of physiological disorders (e.g., of human genetic diseases) that are useful for screening the efficacy of candidate therapeutic compounds or compositions for treating or preventing such physiological disorders. Furthermore, identifying the gene(s) responsible for the phenotype provides potential drug targets for modulating the phenotype and, when the phenotype is clinically relevant, for therapeutic intervention. In addition, the manipulation of the genetic makeup of organisms and the identification of new genes have important uses in agriculture, for example in the development of new strains of animals and plants having higher nutritional value or increased resistance to environmental stresses (such as heat, drought, or pests) relative to their wildtype or non-mutant counterparts.

Since most eukaryotic cells are diploid, two copies of most genes are present in each cell. As a consequence, homozygous mutation is usually required to produce a desired phenotype, since mutating one copy of a gene may not produce a sufficient change in the level of gene expression or activity of the gene product from that in the non-mutated or wildtype cell or multicellular organism, and since the remaining wildtype copy would still be expressed at sufficient levels to produce a functional gene product. Thus, to create a desired change in the level of gene expression and/or function in a cell or multicellular organism, at least two mutations, one in each copy of the gene, are required in the same cell.

In other instances, mutation in multiple genes may be required to produce a desired phenotype. In some instances, a mutation in one copy of a gene may affect the expression levels of the gene but not the activity of the gene product to a desired extent, so that the desired physiological effects on the cell or multi-cellular organism is not achieved. However, a mutation in a second gene, even in only one copy of that second gene, can reduce gene expression levels of the second gene to produce a cumulative phenotypic effect in combination with the first mutation, if the expression levels of both genes are sufficiently low. This effect can alter the function of a cell or multi-cellular organism. An example of this phenomenon is the synergy between blood clotting Factors VIII and IX. A mutation in either gene alone could result in levels that are severely reduced but with no effect on the clotting function. Severe reductions in the level of expression of both genes, however, can have a major impact. This principle can be extended to other instances where mutations in multiple (two, three, four, or more, for example) genes are required cumulatively to produce an effect on activity of a gene product or on another phenotype in a cell or multi-cellular organism. It should be noted that, in this instance, such genes may all be expressed in the same cell type and therefore, all of the required mutations occur in the same cell. However, the genes may normally be expressed in different cell types (for example, secreting the different gene products from the different cells). In this case, the gene products are expressed in different cells but still have a biochemical relationship such that one or more mutations in each gene is required to produce the desired phenotype.

Unfortunately, few methods exist for creating cultured cells that contain multiple gene mutations that produce, cumulatively, a desired phenotype. Such methods often are time-consuming and prone to error. In addition, it is often very difficult or impossible to identify the genes that have been mutated using such methods.

Further, methods for making homozygous mutations in cultured cells, where the mutated genes are not known in advance of mutation, are not known to currently exist. Still further, without a way to identify a homozygous mutation, the artisan cannot associate the phenotype with a given mutation. Currently, to associate a desired phenotype with a homozygous mutation in a cultured cell, the location, structure and/or function of the gene must be known to the artisan in advance. Hence, the methods of mutation known in the art are not suitable for homozygously mutating a cell to achieve a desired phenotype and identifying the gene(s) responsible for the phenotype. Nor are there methods suitable for making cells with multiple mutations that cumulatively produce a desired phenotype and identifying the genes responsible for the phenotype.

Several approaches for introducing mutations into eukaryotic genes are currently in use. Each has significant limitations.

One approach is homologous recombination to mutate the level of gene expression or activity of a gene product in a cell. 1: Montgomery et al., Cell. 1991 Feb. 22;64(4):693-702; 2: Riele et al. Nature. 1990 Dec. 13;348(6302):649-51; 3: Mansour et. al., Proc Natl Acad Sci USA. 1990 October;87(19):7688-92; 4: Koller et al., Proc Natl Acad Sci USA. 1989 November;86(22):8927-31; 5: Capecchi M R. Science. 1989 Jun. 16;244(4910):1288-92; 6: Zimmer A, Gruss P. Nature. 1989 Mar. 9;338(6211):150-3; 7: Joyner A L, Skarnes W C, Rossant J. Nature. 1989 Mar. 9;338(6211):153-6; 8: Thompson S, Clarke A R, Pow A M, Hooper M L, Melton D W. Cell. 1989 Jan. 27;56(2):313-21; 9: Doetschman T, Maeda N, Smithies O. Proc Natl Acad Sci USA. 1998 November;85 (22):8583-7; 10: Doetschman T, Gregg R G, Maeda N, Hooper M L, Melton D W, Thompson S, Smithies O. Nature. 1987 Dec. 10-16;330(6148):576-8; 11: Thomas K R, Capecchi M R. Cell. 1987 Nov. 6;51(3):503-12.

Typically, this approach is taken in embryonic stem cells or embryonic germ cells, which are used to make transgenic animals carrying the mutation of interest. An important limitation of this approach is that the gene to be mutated must be known in advance of mutation, cloned and sequenced to ensure that the mutagenic vector used in homologous recombination contains the appropriate targeting sequences. Furthermore, the process is laborious and results in only one mutant copy of the gene of interest in the cell. Where a phenotype depends on homozygosity for expression, the heterozygous cell, therefore, cannot be used to screen for a change in a phenotype of interest unless additional work is carried out to eliminate the second copy of the gene by homologous recombination. This additional work is time consuming and expensive, and more importantly can only be done on genes that are known to the artisan in advance.

Such mutated heterozygous cells can be used to make transgenic animals. However, such animals will also be heterozygous and may not express a phenotype different from the wildtype or nonmutant animal. Further breeding of the animals to homozygosity is therefore required if one desires to analyze the phenotypic effect of the mutation. Such breeding is time consuming and expensive.

Another approach involves chemical mutagenesis of cells and/or organisms (see, e.g., Brown et al., *Hum. Mol. Genet.* 7:1627-1633 (1998); Chen et al., *Nature Gen.* 24:314-317 (2000); Munroe et al., *Nature Gen.* 24:318-321 (2000); Nolan et al., *Nature Gen.* 25:440-443 (2000); the disclosures of all of which are incorporated herein by reference in their entireties for teaching the use of ENU to generate mutations that result in detectable phenotypes in cells or animals). This approach relies upon the use of one or more chemical mutagens that are able to produce one or more mutations in the genome. As is the case for mutation by homologous recombination, however, chemical mutagenesis also typically results in mutagenesis of only a single copy of a given gene. Since in cases where homozygous mutation is required to achieve a desired phenotype, both copies of a given gene must be mutated before a desired phenotype can be achieved, cells or organisms that undergo a single round of chemical mutagenesis typically do not show a desired change in phenotype. Hence, these cells or organisms generally are not useful for achieving for a desired phenotype.

A further problem is that while chemical mutagenesis results in the mutation of one or more genes in a cell, there is no straightforward way to determine the mutated gene(s) responsible for the phenotype. This approach also fails to provide a method for making multiple mutations that cumulatively provide a desired phenotype that also permits the genes responsible for the phenotype to be easily identified.

As discussed above (for homologous recombination mutagenesis) mutated heterozygous cells prepared by chemical mutagenesis can be used to create transgenic animals. However, the animals will also be heterozygous and may not, therefore, manifest a change in a desired phenotype from the wildtype. Time-consuming and costly breeding of the animals to homozygosity is required. Even if a change in the desired phenotype is observed in the transgenic animals (even in homozygous transgenic animals), it is very difficult, if not impossible, to identify the mutated gene(s) responsible for the phenotype. Therefore, a large number of breedings must be carried out to clone the mutated gene by standard positional cloning methods. Hence, this process is slow, expensive, difficult to carry out on large numbers of mutant animals, and has a high failure rate. Thus, chemical mutagenesis fails to provide homozygous mutations in cultured cells (and hence, in transgenic animals produced from such cells) and fails to provide a simple way to identify the mutated gene(s) responsible for a phenotype in cultured cells or in multi-cellular organisms.

Another approach that has been used to mutate genes involves the use of insertional mutagens, such as gene trap vectors, to mutate genes (e.g., Amsterdam et al., *Genes Dev.* 13:2713-2724 (1999); von Melcher et al., *Genes Dev.* 6:919-927 (1992); Gogos et al., *J. Virol.* 71:1644-1650 (1997); Voss et al., *Dev. Dyn.* 212:171-180 (1998); Zambrowicz et al., *Proc. Natl. Acad. Sci. USA* 94:3789-3794 (1997); Friedrich et al., *Genes Dev.* 5:1513-1523 (1991); the disclosures of all of which are incorporated herein by reference in their entireties for teaching the use of gene traps as a mutagenesis technique). These vectors are typically inserted into the genome of a cell by non-homologous recombination. Upon insertion, these vectors are designed to disrupt transcription and/or translation of a gene. Unfortunately, gene trap vectors are inefficient mutagens and mutate only one copy of a given gene. As a result, homozygous mutations typically cannot be created in cell culture with such mutagens. In animals, the mutant animal must be bred to homozygosity of the mutant gene prior to phenotypic analysis. Since it is difficult and expensive to breed large numbers of animals to homozygosity, this approach has only been used on a relatively small number of genes to date.

This approach also fails to provide a method for making multiple mutations that cumulatively provide a desired phenotype and where the genes responsible for the phenotype can be identified. The probabilities of achieving, in a single cell, insertions in each of the genes required, is low and decreases with the number of genes required to be mutated in order to achieve the desired phenotype. Thus, gene traps fail to mutate multiple genes and fail to create homozygous mutations in cultured cells.

Stark et al. (Human Molecular Genetics 8:1925-1938 (1999)), in a review article on forward genetics in mammalian cells with functional approaches to gene discovery, suggested a potential alternative to complementation of mutants by using expression libraries in order to clone the missing gene. They indicated that the alternative involves retrovirus-mediated insertional mutagenesis in conjunction with chemical mutagenesis. They indicated that it was impractical to use insertional mutagenesis de novo to inactivate two alleles of a target gene. However, there was no indication of how this might be achieved and the reference failed to disclose a description of the method having been carried out in practice. It was suggested to obtain a population of heavily mutagenized cells and then insert retroviruses into those cells to inactivate and mark the gene. However, there was no report of this suggestion having been carried out, no guidance regarding how to perform either of the mutagenesis steps to achieve a successful homozygous mutation.

Accordingly, there exists a need in the art to create homozygous gene mutations on a genome-wide basis in cell culture and in multicellular organisms without knowledge of the gene in advance. There is also a need to provide a way to identify the gene. There is also a need for a method of mutating multiple genes in a cell, required cumulatively to achieve a desired phenotype and to identify one or more of the mutated genes. The ability to mutate multiple genes or to mutate both copies of the same gene in cultured cells or multi-cellular organisms, coupled with the ability to identify the mutant gene(s) would be a highly useful approach to identify novel genes, correlate genes with functions, and use the mutant genes, their wildtype counterparts, and other variants, for example, in drug screening and development, transgenic animal and plant production and in the production of desirable gene products.

BRIEF SUMMARY OF THE INVENTION

The present invention provides, for the first time, a solution to the needs identified above by providing methods of efficiently mutating multiple genes in the same cell and tagging at least one of the mutated genes in cells that contain the mutated multiple genes, so that the identity of one or more of the mutated genes can be achieved. The present invention also provides methods of making homozygous gene mutations and tagging the mutated gene.

In general terms, the present invention is directed to methods for creating mutated cells and multicellular organisms using two or more mutagens where at least one of the mutagens is a polynucleotide that acts as an insertional mutagen. The polynucleotide can be used as a tag to identify the cell containing the mutated gene and/or to identify the mutated gene itself. One aspect of the invention is directed to methods for mutating multiple genes, that cumulatively produce a desired phenotype, within the same cell, and tagging at least one of the mutated genes. Another aspect of the invention is directed to methods of creating one or more homozygous mutations in a cell, that sufficiently alter the mutated gene function to generate a desired phenotype, and that tag at least one of the mutated genes.

One mutational approach used in accordance with the invention relates to methods of mutating cells using physicochemical mutagens. These methods have been shown to efficiently produce mutations in cells, but cannot be used to tag the mutated genes. Since the genes cannot be tagged identification of chemically mutated genes is difficult or impossible.

The other mutational approach used in accordance with the invention relates to methods of mutating cells using insertional mutagens. These methods are known to create heterozygous gene mutations and, in certain cases, to tag the mutated gene. But these methods have not been shown to produce homozygous gene mutations within individual cells or to efficiently produce mutation of multiple genes in a cell which cumulatively produce a desired phenotype. Thus, the present invention utilizes physicochemical mutagenesis in conjunction with insertional mutagenesis to achieve multiple mutations (that cumulatively produce a desired phenotype) within a cell, such that at least one of the mutated genes in each cell containing the multiple mutations is tagged. Thus, one or more of the mutated genes can be identified by detecting the tag. In the case of homozygous mutations, at least one of the mutated copies of the gene is tagged so that the mutation that is responsible for the desired phenotype can be identified.

According to the invention, physicochemical mutagens are used to mutate one or more genes in a cell. Mutations include, but are not limited to, point mutations, insertions, deletions, inversions, base modifications and translocations. Such mutations result in events such as splicing defects that alter exon utilization, frame shifts, truncation (5' and 3') of transcripts and of proteins (amino terminal and carboxy-terminal) and alteration of the sequence or abundance of the protein products of mutated genes by changing the identify of individual residues in the primary protein sequence, by fusing the coding sequence of more than one gene to create fusion protein and by changing the abundance of otherwise normal proteins through mutagenesis-induced changes in the production, stability or translatability of transcripts from mutated genes.

Since most eukaryotic genomes are at least diploid (e.g. each gene consists of at least two copies), when a gene is mutated in a eukaryotic cell in this fashion, only one copy is typically mutated so that the other copy remains unmutated. Therefore, a homozygous mutation, in which gene expression from both copies of a given gene is eliminated, is not typically achieved by physicochemical mutagenesis alone.

Therefore, in order to circumvent this deficiency, insertional mutagenesis is also carried out in addition to the physicochemical mutagenesis. In this procedure, the level of physicochemical mutagenesis is adjusted to be mutagenic but not to generate the phenotype of interest in the absence of the insertional mutagenesis. One or more insertional mutagens is inserted into the genome of the host cell or organism in such a manner so as to alter the expression of a functional gene product (e.g., an RNA or protein) of one or more cellular genes. The one or more inserted mutagens also have the property of "tagging" the insertionally mutated gene, thereby allowing it to be identified.

By carrying out both physicochemical mutagenesis and insertional mutagenesis on the same cell, a cell is created in which one or more genes have been mutated by the physicochemical mutagen and one or more genes have been mutated by the insertional mutagen. In one such embodiment of the invention, a cell is created in which one copy of a given gene has been mutated by the physicochemical mutagen and the other copy of the same gene has been mutated by the insertional mutagen, thereby creating cells that carry homozygous mutations in that gene. Such mutations can produce desired phenotypes. The mutant cell can thus be screened for the production of desired phenotypes and the tag can be used to identify the gene responsible for the phenotype.

Using the two mutational approaches, cells are also provided that contain mutations in more than one gene which cumulatively act to produce a desired phenotype. At least one of the mutated genes that contribute to causing the phenotype is tagged by an insertional mutagen. Taking a simple case in which two genes are required to be mutated, the invention includes the following scenarios (1) Gene #1 is mutated by physicochemical mutagenesis and Gene #2 is mutated by insertional mutagenesis in one cell. (2) Gene #1 is mutated by insertional mutagenesis and Gene #2 is mutated by physicochemical in a second cell. Both cells exhibit the desired phenotype, which is caused by the mutation of two genes cumulatively. In the first cell, only Gene #2 can be identified by the tag. In the second cell, only Gene #1 can be identified by the tag. These two cells, however, provide complete information about the identity of the genes that must be mutated to achieve the desired phenotype.

The two types of mutational events described herein can be carried out in either order, or simultaneously. The mutational events can also be repeated, such that a given cell, population of cells or organism can be subjected to physicochemical mutagenesis and/or insertional mutagenesis one or more (e.g., two, three, four, five, six, seven, eight, nine, ten, fifteen, twenty, etc.) times, in any order or simultaneously. At any point(s) in this process the cells or organism can be screened for a desired phenotype, or for insertion of an insertional mutagen both having a desired phenotype or containing the insertion may be isolated and cloned. In a preferred embodiment, physical chemical mutagenisis proceeds insertional mutagenisis, cells are selected for insertional mutagenisis. The insertional mutagen is a 5' gene trap with signals for site specific recombination and transposition.

The invention also provides polynucleotides that act as insertional mutagens for use in the insertional mutagenesis methods of the invention. Such polynucleotides can have any nucleotide sequence and any geometry (e.g., linear, circular, coiled, supercoiled, etc.), and can be double-stranded or single-stranded. Preferred insertional mutagens are described in the Figures and Examples herein. The only limitation is that they be mutagenic and provide the tagging function.

In a preferred embodiment, the insertional mutagen comprises a splice acceptor sequence that is not operably-linked to a promoter sequence. In other preferred embodiments, the insertional mutagen comprises one or more of the following elements: stop codons in all three frames found 3' to the splice acceptor, an internal ribosome entry site, a selectable marker, and a polyA trap. PolyA traps are described in detail in U.S. application Ser. No. 09/276,820 herein incorporated by reference for the teaching of polyA traps. In the above embodiment, the selectable marker preferably is operably-linked to a polyadenylation signal. In other preferred embodiments, the insertional mutagen contains retrovirus sequences that allow the retrovirus replication and infection cycle. In other preferred embodiments, the insertional mutagen contains sequences necessary for transposition. In a highly preferred embodiment, the insertional mutagen contains a splice acceptor that is not operably-linked to a promoter, the splice acceptor having an optimal branch point, stop codons in all three frames, an internal ribosome entry site that includes an exonic splicing enhancer, a selectable marker with a polyadenylation signal, a polyA trap, and wherein these elements are contained in a retrovirus vector or contain transposition signal sequences. In a further preferred embodiment, the insertional mutagen contains a splice acceptor not operably-linked to a promoter, the splice acceptor containing an optimal branch point, stop codons in all three frames, an internal ribosome entry site, a selectable marker with a polyadenylation signal operably-linked to it, and wherein the insertional mutagen is a retrovirus vector or contains transposition signals. Furthermore, in any of the embodiments herein and especially in the preferred embodiments of above, preferred insertional mutagens also contain recombination sites for site specific recombination as described herein.

The invention also encompasses cells created by the methods of the invention, which preferably are eukaryotic cells (e.g., plant cells, fungal cells (including yeast cells), animal cells (including insect cells, avian cells, worm cells, mammalian cells (including human cells, non-human primate or simian cells, rodent (rat, mouse, etc.) cells, rabbit cells, bovine cells, ovine cells, porcine cells, canine cells, feline cells), and the like). These cells can be isolated and cloned, using methods that are well-known in the art to those of ordinary skill. Primary or established cells can be used in the methods of the invention to prepare the mutated cells.

In another aspect, the invention also provides libraries of cells created by the present invention. A physicochemical/insertional mutation library is created when both mutational processes are carried out on more than one cell, preferably $10^6$-$10^8$ cells (for cells with large genomes such as mammalian cells) or as needed to ensure mutational saturation with the combined mutagenesis. The population of cells can all be the same (as in a cell line), or can comprise different subpopulations (as, for example, in cell populations prepared from tissues). Each clone in such libraries may contain a set of mutated genes that is distinct from the set of mutated genes in other clones within the library. Alternatively, the same genes may be mutated in different clones but the type of mutation of each gene could be different. For example, all three genes, Genes #1, #2, and #3, could be mutated in three different clones but the type of mutation (insertional vs physicochemical) could differ. (See schematic) Such libraries of cells therefore, are useful to rapidly screen for desired phenotypes (e.g., changes from the wildtype or nonmutant phenotype) that result from various single mutations or various combinations of mutations.

A library can also encompass a population (two or more, preferably $10^2$-$10^5$ of cells that has been subjected to either insertional mutagenesis or physicochemical mutagenesis but not both. These libraries serve as a population of cells that form a substrate for further mutation by the second mutagenic process of the invention. The efficiency of physicochemical mutagenesis permits the creation of smaller libraries that contain mutation in all genes than are obtained using the less efficient insertional mutagenesis.

Accordingly, the invention encompasses a method for making a library of mutagenized cells by insertionally mutagenizing at least one physicochemically mutagenized cell from among two or more physicochemically mutagenized cells. The invention is also directed to a method for making a library of mutagenized cells by physicochemically mutagenizing at least one insertionally mutagenized cell from among two or more insertionally mutagenized cells. The invention also encompasses methods for making a library of mutagenized cells by simultaneously mutagenizing two or more cells with one or more physicochemical mutagens and one or more insertional mutagens. The invention also encompasses methods for making a library of mutagenized cells by subjecting two or more cells containing a physicochemical mutagen to insertional mutagenisis. The invention is also directed to a method for making a library of mutagenized cells by administering a physicochemical mutagen to two or more cells containing an insertional mutagen. One or more cells can be screened for mutation of a specific desired gene or other desired phenotype at any stage of the process, such as after any physicochemical mutagenesis event, after any insertional mutagenesis event, or after both or all mutagenesis events. Cells having a desired phenotype can be isolated and cloned. Cells can also be screened for the possession of an insertional mutagen at any stage of the process, such as after any physicochemical mutagenesis event, after any insertional mutagenesis event, or after both or all mutagenesis events. These cells can be subjected to further insertional mutagenesis or physicochemical mutagenesis. These cells can be isolated and/or cloned at any stage of the process, such as after selection for possession of an insertional mutagen. Such clones can accordingly form the substrate for further mutagenesis events. In one embodiment, physicochemical mutagenesis is performed on a plurality of cells. The cells are then expanded to form clonal populations and these populations are subjected to insertional mutagenesis so that a heterogeneous population of insertionally mutagenized cells is formed. These cells may or may not be expanded but can be screened for mutation of a specific desired gene or for a desired phenotype. In another exemplary embodiment, a plurality of cells is physicochemical mutated, the cells expanded, and then insertionally mutagenized. This first insertion may or may not be the insertion that causes the phenotype. An insertion that causes the phenotype may be produced from further insertions of the original insertional mutagen. For example, after the original insertional mutagenesis event, the cells could be expanded and, after expansion, a component could be introduced into the cell or induced in the cell that will cause further insertional mutagenesis, such as a transposase. In a related exemplary embodiment, cells can be both physicochemically mutagenized and insertionally mutagenized (simultaneously) expanded, and a factor to cause insertional mutagens can be introduced either into the cells or can be induced in the cells. In a related exemplary embodiment, cells can be insertionally mutagenized with the introduction of a first insertional mutagen, expanded, and then a factor causing further insertion from the endogenous insertional mutagen can be activated in the cells which can then be physicochemically mutated. As mentioned, cells may or may not be expanded following each treatment.

At any stage after a phenotype is produced by mutation, the presence of site-specific recombination sequences on the insertional mutagen can be used to ascertain whether the insertion caused the phenotype. If the excision of the insertional mutagen reverts the phenotype, this indicates that mutation causing the phenotype was caused by an insertion.

The invention also provides methods of using the cells and libraries to screen for phenotypes that are created by the mutagenesis methods of the invention and to identify one or more mutations responsible for the phenotype.

The methods of the invention provide a way to establish the function of a gene. With the methods it is possible to determine the function of any specific desired gene. Cells can be mutated and screened for a mutation in a specific desired gene with any assay that can be used to specifically detect a mutation in that gene. The effect of the mutation on the cell or animal can then be ascertained. In this case, the tagged insertional mutagen is useful for identification of cells containing mutation of the gene of interest.

Alternatively, mutated cells can be screened at random for a desired phenotype, or for production of a desired phenotype in a multi-cellular organism made from the cell, and the phenotype can be then correlated with mutation in one or more genes by means of the tag. Alternatively, a cell that is mutated can be selected on the basis of the phenotype it has or confers on an organism made from the cell, and that phenotype can then be correlated with mutation in one or more genes by means of the tag. Thus, any change in phenotype of the cell (or of multicellular organism derived from the cell) from that of the non-mutated cell (or cellular organism) can be ascribed to the mutated gene. Mutated genes that give rise to desired phenotypes can be selected, identified, and characterized e.g., cloned, sequenced, mapped, etc. According to this aspect of the invention, the function of any gene can be identified and assessed. Thus, a phenotype can be correlated with a gene that is known in the art (previously identified, e.g., mapped, cloned, sequenced, or otherwise characterized) or with a gene that is not known in the art.

Although the methods of the invention identify a mutated gene, the invention provides a way to correlate the gene with a function and thus provides a way to ascribe a function to the wildtype gene and to use that wildtype gene and gene product. The invention, therefore, provides for use of the wildtype gene or other natural variant of the gene that is identified as described above. This includes, but is not limited to, allelic variants, homologs, orthologs, pseudogenes, and the like. The wildtype gene, that has been identified by means of the mutated version, as well as other variants, can be isolated, for example, from non-mutated cells, using standard recombinant DNA or molecular biological techniques, such as cDNA library screening or PCR. The wildtype gene/protein or other variant can be used, for example, as a therapeutic protein, antibody target. Naturally-occurring mutants are also useful as therapeutic or diagnostic targets, for example, with antibodies or other detectable and/or inhibiting binding reagent.

In a diseased tissue or cell, a naturally mutant gene gives rise to the disease. Further mutation by the present method can revert the cell or organism to a normal phenotype allowing identification of the mutated disease gene.

The invention also encompasses use of the mutated cells to produce transgenic animals. Transgenic animals can be created from mutant somatic or germ cells, or from mutant stem cells (e.g., embryonic or adult stem cells), that have been produced by methods of the invention. Donor cells (which may be a somatic cell, an adult stem cell, a germ cell or an embryonic stem cell from a donor animal) are subjected to insertional mutagenesis and physicochemical mutagenesis in vitro so as to produce a mutated donor cell with a single homozygous mutation that produces a desired phenotype in the cell or organism or a mutated donor cell with mutations in multiple genes (that cumulatively will achieve a desired phenotype in the cell or organism). The animal can be made by transferring the nucleus from the donor cell to a recipient cell (which may be, for example, a fertilized oocyte that has been enucleated), and producing a transgenic organism from the recipient cell. Alternatively, the mutant stem cell could be implanted into a blastocyst or the mutant germ cell used to create a mutant zygote through in vitro fertilization or artificial insemination and the resulting mutant zygotes put into a pseudo-pregnant female to produce the transgenic organism.

Genetically modified animals can be created by transplantation of nuclei from cells that have been mutagenized by the techniques of the present invention. Nuclei extracted from mutant cells are then implanted into enucleated fertilized eggs, and the resultant zygote is implanted into a pseudopregnant female to develop into an animal carrying the mutations that were generated in the original mutagenized cell.

Zygotes can also be formed from mutant embryonic or other pluripotent stem cell following the blastocyst fusion protocols that have been developed for the creation of genetically modified mice.

Briefly, the modified stem cells are combined with cells of a diploid or tetraploid morula or the modified cells are injected directly into the blastocoel of a developing blastocyst. The chimeric zygote that results is implanted into a pseudopregnant female to develop into an animal carrying the mutations generated in the stem cell. Genetically modified germ cells can be created by in vitro retroviral-mediated or other gene delivery into spermatogonial stem cells of both adult and immature animals and can result in stable integration of the insertional mutagen in 2-20% of stem cells. After transplantation of the transduced stem cells into the testes of infertile recipient animals, approximately 4.5% of progeny from these males contain the insertional mutagen, and this mutagenic vector is transmitted to and functions in subsequent generations. 1: Chesne P, Adenot P G, Viglietta C, Baratte M, Boulanger L, Renard J P. Nat Biotechnol. 2002 April;20(4):366-9; 2: Hosaka K, Ohi S, Ando A, Kobayashi M, Sato K. Hum Cell. 2000 December;13(4):237-42; 3: Wolf E, Zakhartchenko V, Brem G. Biotechnol. 1998 Oct. 27;65 (2-3):99-110.; In Hogan B, Beddington R, Costantini F, Lacy E. Manipulating the Mouse Embryo; a Laboratory Manual Cold Spring Harbor Laboratory Press. 1994; 1: Cecconi F, Gruss P. Methods Mol Biol. 2002; 185:335-46. Review; 1: Brinster R L. Science. 2002 Jun. 21;296(5576):2174-6; 2: Nagano M, Brinster C J, Orwig K E, Ryu B Y, Avarbock M R, Brinster R L. Proc Natl Acad Sci USA. 2001 Nov. 6;98(23): 13090-5; 1: Cecconi F, Gruss P. Methods Mol Biol. 2002; 185:335-46.

In another embodiment, transgenic organisms can be created from cells chosen because they display a desired phenotype in vitro after being subjected to insertional and physicochemical mutagenesis according to the methods of the invention. The identity of the gene or genes responsible for the phenotype may or may not be known at this stage for the preparation of transgenic animals. In another embodiment transgenic organisms can be created from a cell with a mutation in a specific desired gene. In another embodiment, mutated cells can be selected at random, used to make the transgenic organism, and the transgenic organism can be screened for a desired phenotype.

The invention also encompasses methods for making transgenic animals and transgenic animals produced by the present methods. Transgenic animals that can be produced by the methods of the invention include, for example, insects (including Drosophila, Spodoptera and Trichoplusa species), birds, worms (including *C elegans*), fish (including zebrafish), mammals (including humans, and non-human mammals such as simians and other non-human primates, mice, rats, pigs, cows, sheep, dogs, cats, and the like). The transgenic animals can be used, for example, as models for human disease, to study gene function, to screen for phenotypes of interest, for agricultural applications, or for drug testing.

In one aspect of the invention, transgenic animals are produced from cells that have been physicochemically mutated in vitro. The cells of the recipient animal may then be mutated by insertional mutagenesis. The insertional mutagen can be introduced exogenously into the animal or can be induced or activated from an endogenous incorporated insertional mutagen. In one embodiment, the insertional mutagenesis is achieved by crossing the transgenic animal produced from a physicochemically mutated cell with another animal containing an insertional mutagen in its germ line, such as a transposon, such as those described herein. The animal can be screened for mutation of a specific desired gene or for expression of another desired phenotype after the physicochemically mutated cell has been used to form the animal and/or after the insertional mutagenesis.

The invention also provides methods of producing transgenic plants, and transgenic plants produced by such methods. Transgenic plants that can advantageously be produced according to such methods include dicotyledenous and monocotyledenous plants.

The invention also encompasses the use of the mutant cells for drug screening. In this embodiment, mutant cells are exposed to test compounds or compositions which may have therapeutic potential, to determine the effect of the compound or composition on a desired phenotype induced by one or more mutations in the mutant cells, including the level of expression or activity of the mutated gene or protein. Furthermore, the wildtype genes or other variants that correspond to the mutated gene or genes, also can be used to identify drugs that affect a phenotype caused by the gene or genes, including the level of expression or activity of the wildtype or variant gene or protein of interest.

Other preferred embodiments of the present invention will be apparent to one of ordinary skill in light of what is known in the art, in light of the following drawings and description of the invention, and in light of the claims.

BRIEF DESCRIPTION OF THE DRAWINGS/FIGURES

FIGS. 1A-1J: Non-limiting examples of 5' gene trap insertional mutagens vectors useful in the present invention. Each insertional mutagen is illustrated schematically in its linear form; however, insertional mutagens of the invention can have any geometry (linear, circular, coiled, supercoiled, etc.). Horizontal lines and boxes indicate polynucleotides, such as DNA or RNA. Stop codons can be present in any reading frame, or nested such that they are present in all reading frames. S/A represents a splice acceptor site. S/D represents a splice donor site. pA represents a polyadenylation signal. ET represents an epitope tag.

FIGS. 2A-2H: Non-limiting examples of 5' gene trap insertional mutagens useful in the present invention. Each insertional mutagen is illustrated schematically in its linear form. Horizontal lines and boxes indicate polynucleotides such as DNA or RNA. SM and RG represent selectable marker and reporter gene, respectively. S/A represents a splice acceptor site. S/D represents a splice donor site. pA represents a polyadenylation signal. IRES represents internal ribosomal entry site.

Figure 3A:
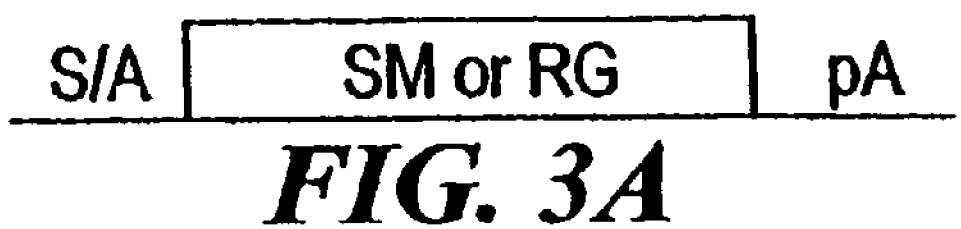
Figure 3B:
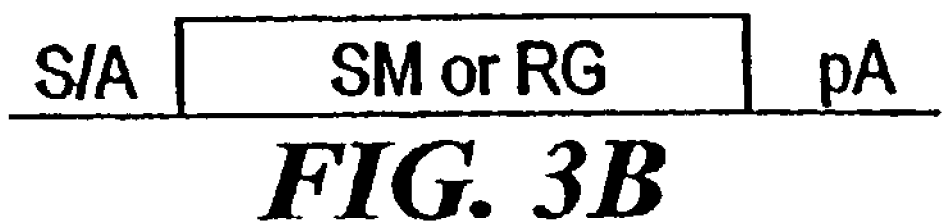

FIGS. 3A-3B: Non-limiting examples of 5' gene trap insertional mutagens useful in the present invention. Each insertional mutagen is illustrated schematically in its linear form. Horizontal lines and boxes indicate polynucleotides such as DNA or RNA. SM and RG represent selectable marker and reporter gene, respectively. S/A represents a splice acceptor site. pA represents a polyadenylation signal. IRES represents internal ribosomal entry site.

Figure 4A:
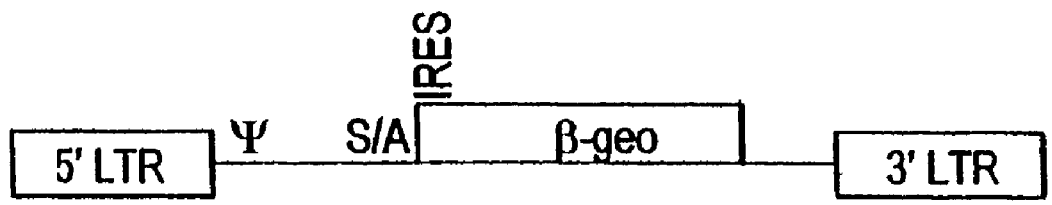
Figure 4B:
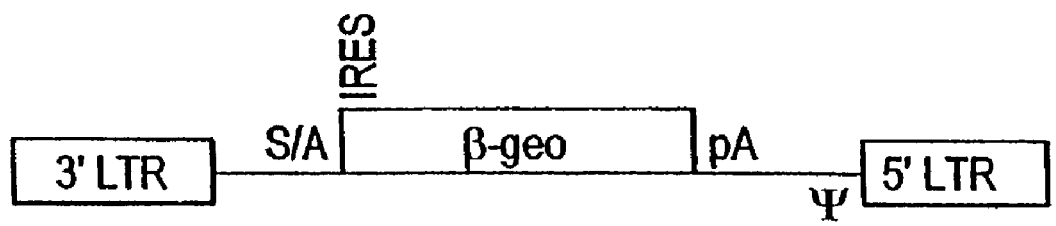
Figure 4C:
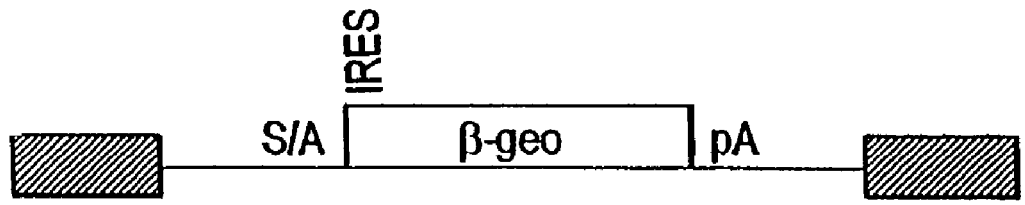

FIGS. 4A-4C: Non-limiting examples of 5' gene trap insertional mutagens useful in the present invention. Each insertional mutagen is illustrated schematically in its linear form. Horizontal lines and boxes indicate polynucleotides such as DNA or RNA. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In FIG. 4B, the 5' LTR, 3' LTR, and ψ are shown upside down to indicate that the retroviral sequence is in reverse orientation relative to the splice acceptor site and β-geo gene. In FIG. 4C, the solid boxes represent transposon signals.

Figure 5A:
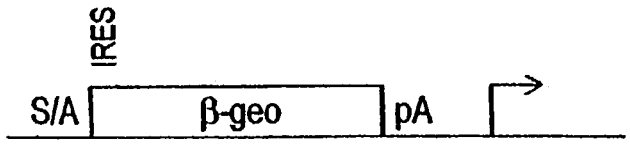
Figure 5B:
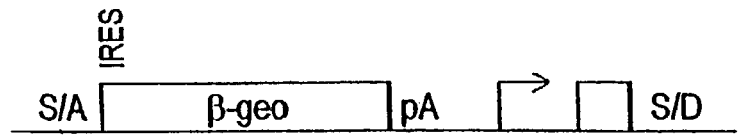
Figure 5C:
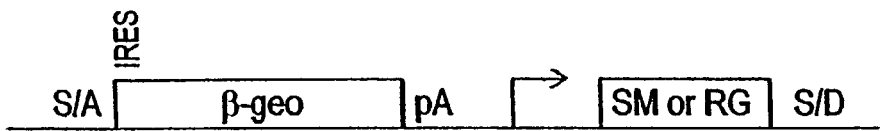
Figure 5D:
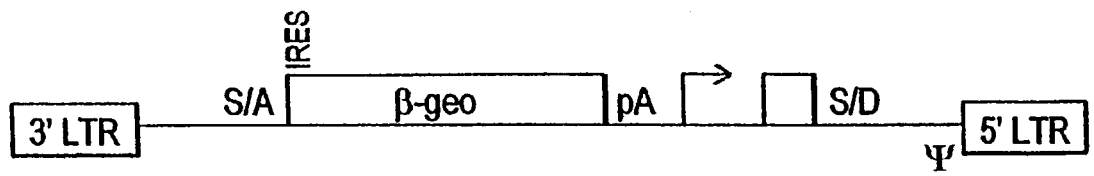
Figure 5E:
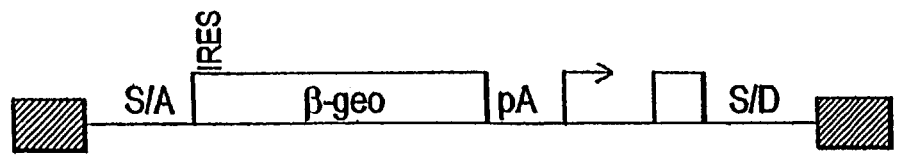

FIGS. 5A-5E: Non-limiting examples of 5' gene trap insertional mutagens containing a 3' gene trap component. Each insertional mutagen is illustrated schematically in its linear form. Horizontal lines and boxes indicate polynucleotides such as DNA or RNA. Arrows represent promoters. SM and RG represent selectable marker and reporter gene, respectively. β-geo is a fusion of the neomycin resistance gene and β-galactosidase gene. S/A represents a splice acceptor site. S/D represents a splice donor site. pA represents a polyadenylation signal. IRES represents internal ribosomal entry site. 5' LTR and 3' LTR represent retroviral long terminal repeats. ψ represents retroviral packaging signal. In FIG. 5D, the 5' LTR, 3' LTR, and ψ are shown upside down to indicate that the retroviral sequence is in reverse orientation relative to the splice acceptor site and β-geo gene. In FIG. 5E, the solid boxes represent transposon signals.

Figure 6A:
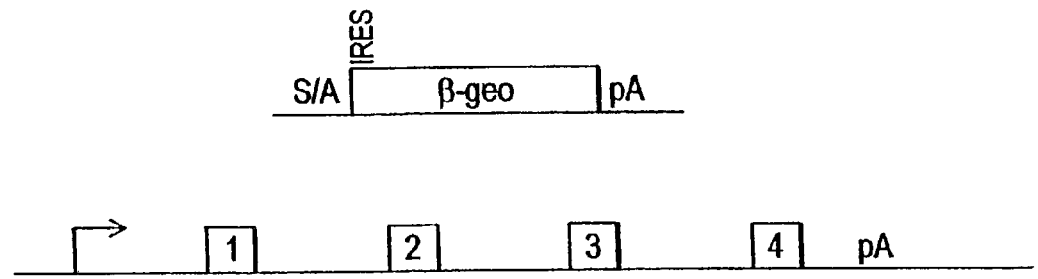
Figure 6B:
Figure 6B:
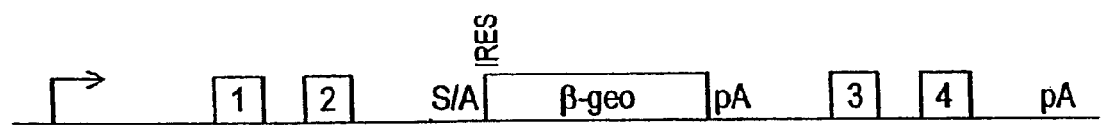
Figure 6C:
Figure 6C:
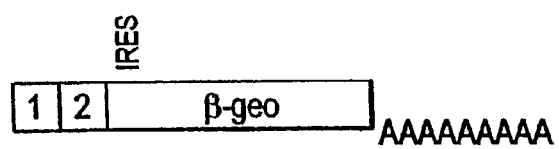

FIGS. 6A-6C: Proposed mechanism of gene mutation using a 5' gene trap. Vector is illustrated schematically in its linear form. Horizontal lines and boxes indicate polynucleotides such as DNA or RNA. Arrows represent promoters. β-geo is a fusion of the neomycin resistance gene and β-galactosidase gene. S/A represents a splice acceptor site. pA represents a polyadenylation signal. IRES represents internal ribosomal entry site. FIG. 6A shows the insertional mutagen and the endogenous gene prior to vector insertion. FIG. 6B shows the endogenous gene following insertion of the insertional mutagen. FIG. 6C shows the fusion mRNA produced from the endogenous gene.

Figure 7A:
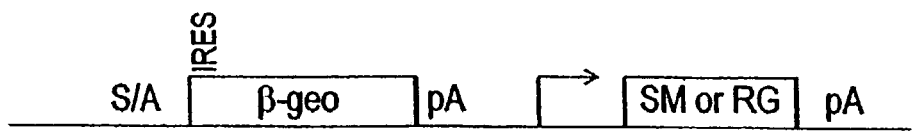
Figure 7B:
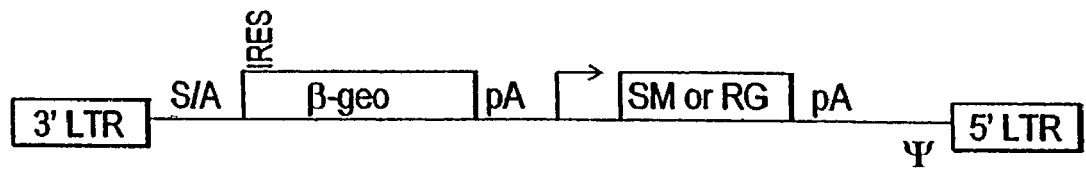

FIGS. 7A-7B: Non-limiting examples of 5' gene trap insertional mutagens containing a promoter linked to a selectable marker or reporter gene followed by a polyadenylation signal. Each insertional mutagen is illustrated schematically in its linear form. Horizontal lines and boxes indicate polynucleotides, such as DNA or RNA. Arrows represent promoters. SM and RG represent selectable marker and reporter gene, respectively. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In FIG. 7B, the 5' LTR, 3' LTR, and v are shown upside down to indicate that the retroviral sequence is in reverse orientation relative to the splice acceptor site and β-geo gene. The presence of the promoter operably linked to a selectable marker/reporter gene and polyadenylation signal allows selection of integrated insertional mutagens independent of whether or not integration has occurred in a transcriptionally active region of the genome. The figure is illustrative of several insertional mutagen types containing selectable markers; however, the promoter/selectable marker/polyadenylation signal unit can be used on any of the insertional mutagens described herein.

Figure 8A:
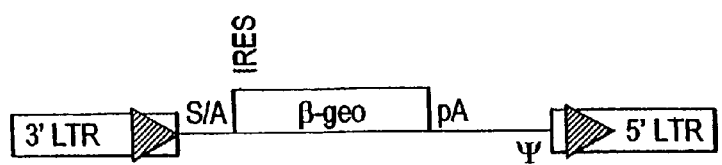
Figure 8B:
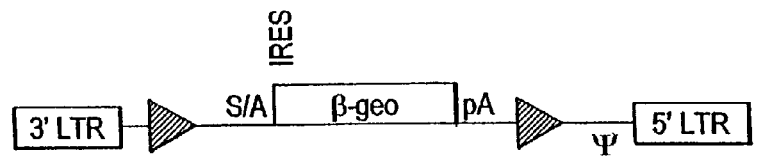
Figure 8C:
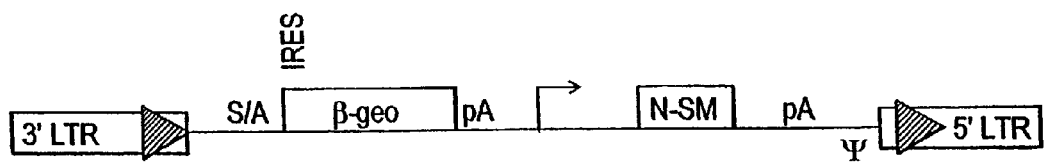

FIGS. 8A-8C: Non-limiting examples of 5' gene trap insertion insertional mutagens containing site-specific recombination signals. Each insertional mutagen is illustrated schematically in its linear form. Horizontal lines and boxes indicate polynucleotides such as DNA or RNA. Arrows represent promoters. Filled triangles represent site-specific recombination signals. The site-specific recombination signals can be in any orientation relative to one another. The figure depicts an orientation that promotes excision of the insertional mutagen from the genome. If the signals are placed on the insertional mutagen in the opposite direction relative to each other, the insertional mutagen would be inverted in the genome following site specific recombination. N-SM represents a negative selectable marker gene. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In each example, the 5' LTR, 3' LTR, and ψ are shown upside down to indicate that the retroviral sequence is a reverse orientation relative to the splice acceptor site and β-geo gene. The position of the site-specific recombination signals in FIGS. 8A and 8C is shown in the viral LTRs such that most of the viral insertional mutagen can be excised (see, e.g., Ishida, *Nucl. Acids Res.* 27: e35 (1999)). The presence of the promoter operably linked to a negative selectable marker and polyadenylation signal allows selection for cells in which the integrated insertional mutagen has been excised. The present figure is illustrative of several insertional mutagen types containing site-specific recombination signals; however, the site-specific recombination signals can be used on any of the insertional mutagens described herein, including the non-viral insertional mutagens.

FIGS. 9A-9H: Non-limiting examples of 5' gene trap insertional mutagens containing site-specific recombination signals (also equivalently referred to herein as recombination sites). Each insertional mutagen is illustrated schematically in its linear form (although insertional mutagens can exist in any conformation, including linear, circular, coiled, supercoiled, branched, etc.). Horizontal lines and boxes indicate polynucleotides such as DNA or RNA. Arrows represent promoters. Filled triangles represent site-specific recombination signals. The site-specific recombination signals can be in any orientation relative to one another. Recombination sites shown in opposite orientation relative to one another (e.g., FIGS. 9D-9F and 9H) produce an inversion following recombination, whereas recombination sites shown in the same orientation relative to one other (e.g., FIGS. 9A-9C and 9G) produce a deletion upon recombination. N-SM represents a negative selectable marker gene, while P-SM represents a positive selectable marker gene. Neo represents a neomycin resistance gene. TK represents a herpesvirus thymidine kinase (HSV-TK) gene. S/A represents a splice acceptor site. pA represents a polyadenylation signal. IRES represents an internal ribosome entry site. The presence of the promoter operably linked to a negative selectable marker and polyadenylation signal allows selection for cells in which the integrated insertional mutagen has been excised. Where the positive selectable marker and/or the negative selectable marker lack a promoter on the insertional mutagen, the marker can be expressed from an endogenous promoter upon integration of the insertional mutagen into the genome of the host cell. The present figure is illustrative of several insertional mutagen types containing site-specific recombination signals; however, the recombination sites can be used on any of the insertional mutagens described herein, including the non-viral insertional mutagens. In addition, any of the insertional mutagens shown in this figure can optionally contain no (or only one) site-specific recombination signal(s). The insertional mutagens depicted in FIGS. 9A-9F can optionally lack the S/A, IRES and/or pA signal. Each of the insertional mutagens shown optionally can be configured as a viral insertional mutagen and therefore can contain 5' and 3' LTRs and packaging signals. As one of ordinary skill will readily appreciate, other insertional mutagen elements described herein and/or recognized in the art can be included in the insertional mutagens in addition to the elements illustrated in the figures.

Figure 9A:
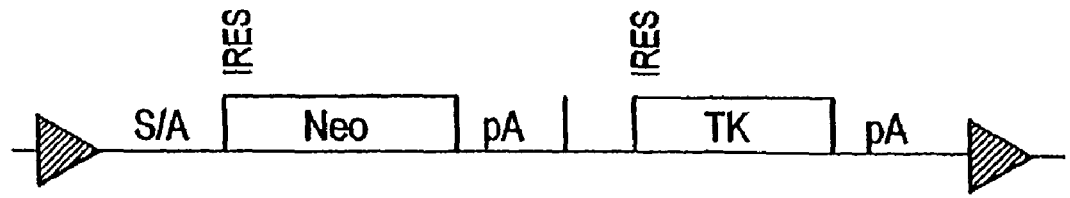
Figure 9B:
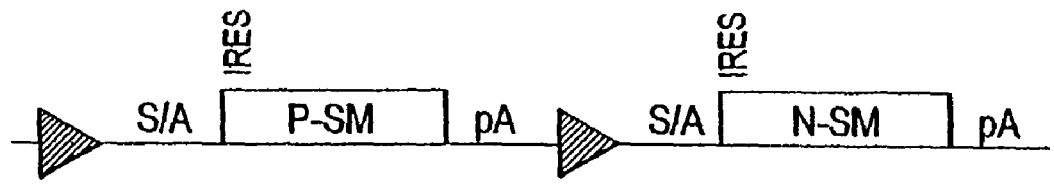
Figure 9C:
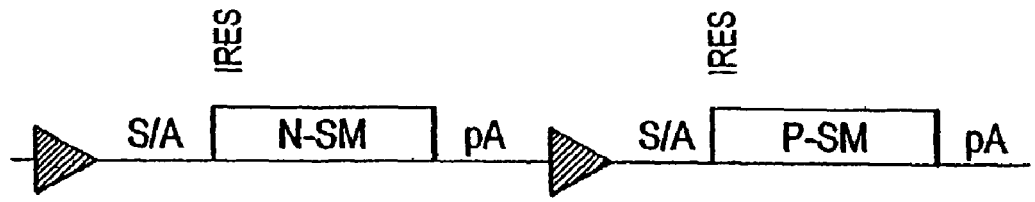
Figure 9D:
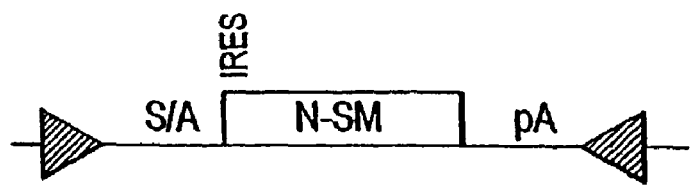
Figure 9E:
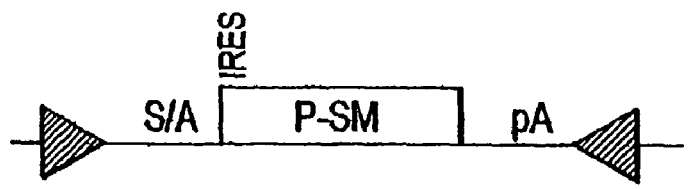
Figure 9F:
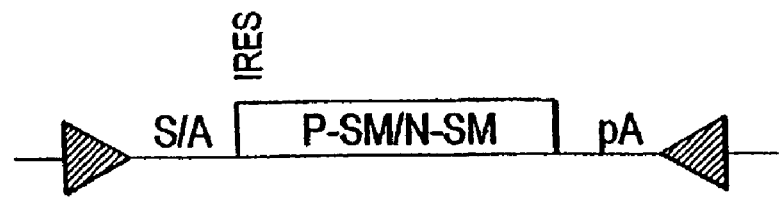
Figure 9G:
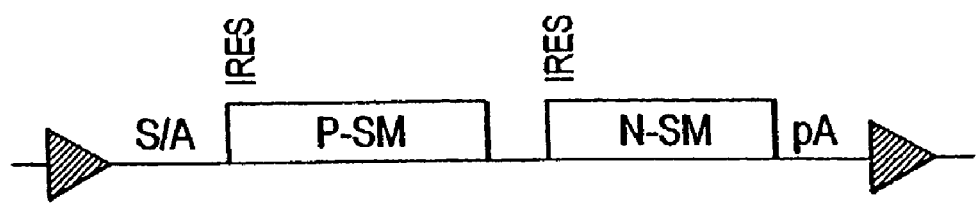
Figure 9H:
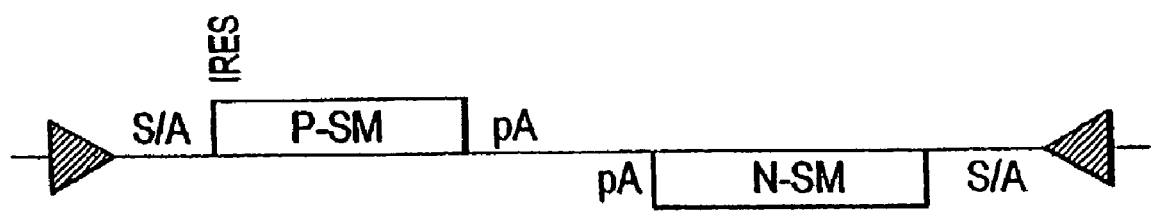
Figure 10A:
Figure 10B:
Figure 10C:
Figure 10D:
Figure 10E:
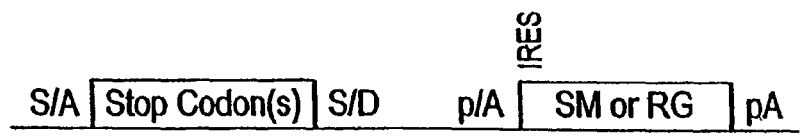
Figure 10F:
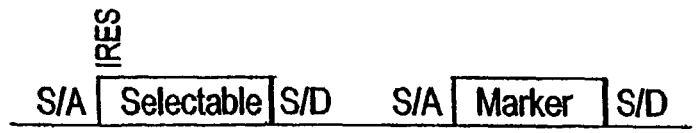
Figure 10G:

FIGS. 10A-10G: Non-limiting examples of 5' gene trap insertional mutagens containing multiple exons. Each insertional mutagen is illustrated schematically in its linear form (although vectors can exist in any conformation, including linear, circular, coiled, supercoiled, branched, etc.). Horizontal lines and boxes indicate polynucleotides such as DNA or RNA. Arrows represent promoters. S/A represents a splice acceptor site, and S/D represents a splice donor site. pA represents a polyadenylation signal. IRES represents an internal ribosome entry site. SM indicates a positive or negative selectable marker. A reporter gene can be substituted for the SM on any of the insertional mutagens shown in this figure. In FIGS. 10F and 10G, the selectable marker open reading frame has been separated onto different exons. Upon transcription from an endogenous gene, followed by splicing, the open reading frame will be reconstituted to produce a functional SM. It will be recognized by the ordinarily skilled artisan that each of the insertional mutagens depicted in this figure can optionally contain one or more site-specific recombination signals (see FIG. 9). Optionally, the insertional mutagens depicted in this figure can lack the S/A, IRES, S/D and/or pA signal. Each of the insertional mutagens shown optionally can be configured as a viral insertional mutagen and therefore can contain 5' and 3' LTRs and packaging signals. As one of ordinary skill will readily appreciate, other elements described herein and/or recognized in the art can be included in the insertional mutagens in addition to the elements illustrated in the figures.

Figure 11:
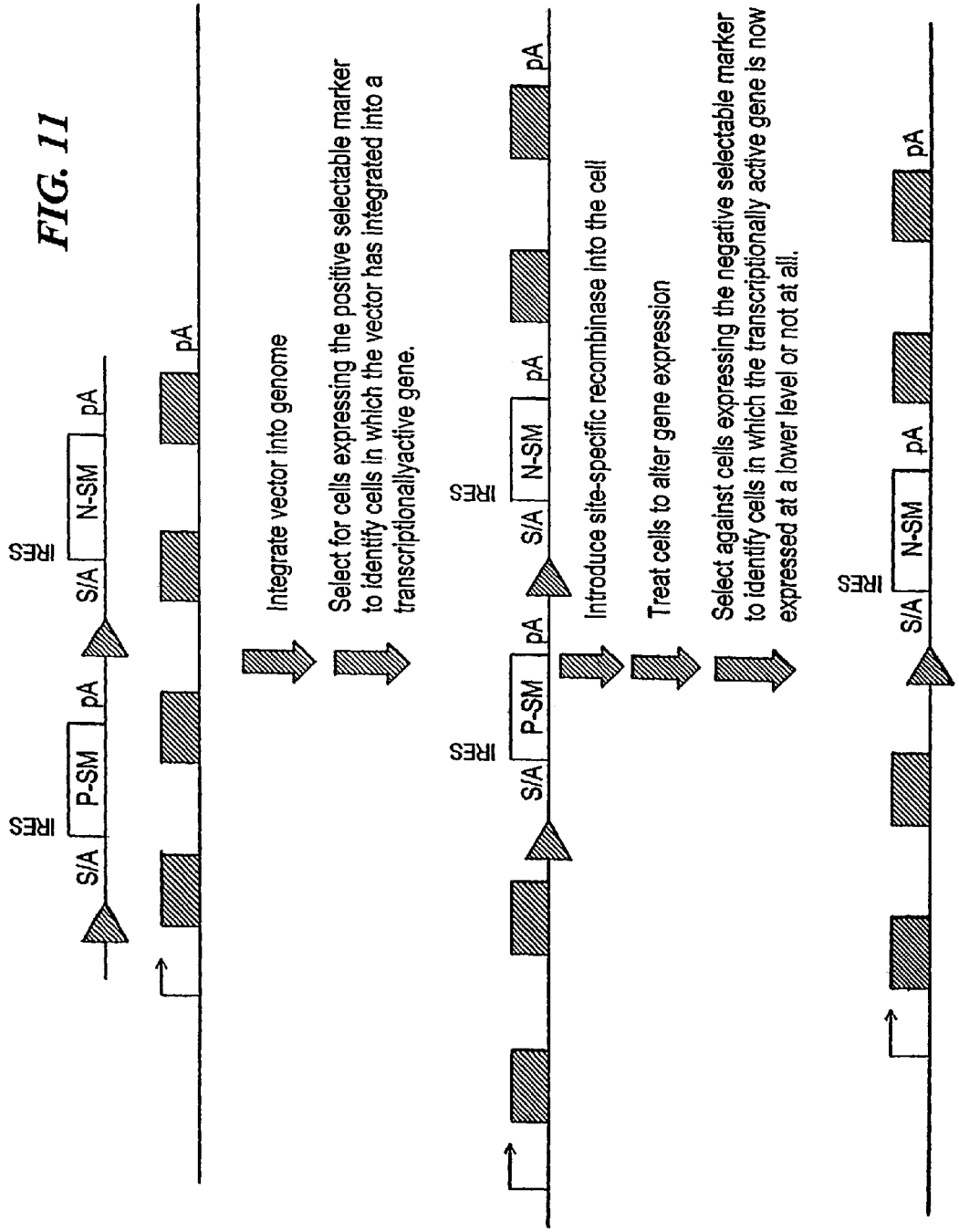

FIG. 11: Method for detecting gene trap insertions that occur in developmentally regulated genes. In this example, cells are identified in which a transcriptionally active gene became down regulated or silenced in response to specific treatments or environmental stimuli to the cells. DNA is illustrated schematically in its linear form. Horizontal lines and boxes indicate polynucleotides such as DNA or RNA. Arrows represent promoters. Filled triangles represent site-specific recombination signals. The site-specific recombination signals are depicted in an orientation that promotes excision of the positive selectable marker from the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 12:
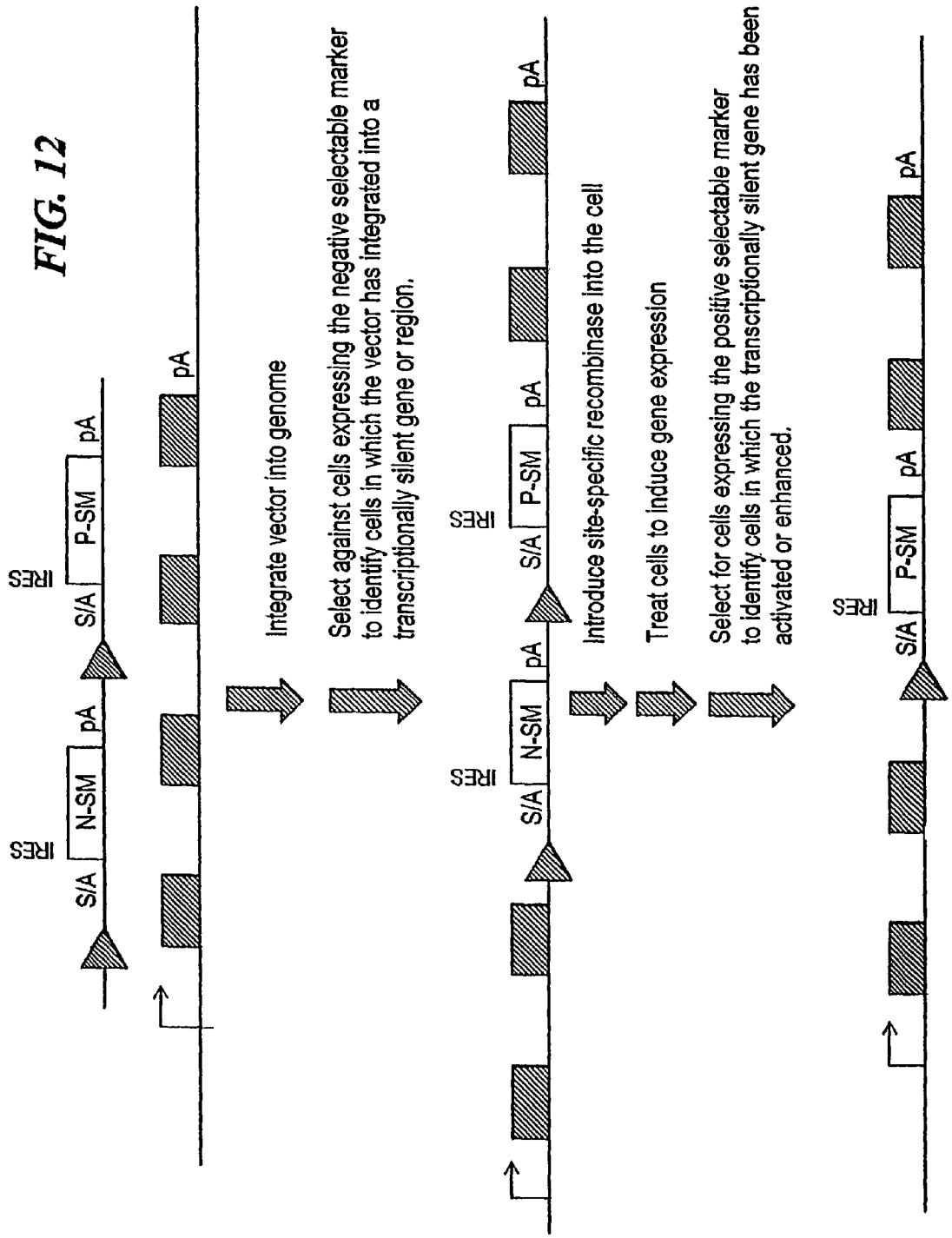

FIG. 12: Method for detecting gene trap insertions that occur in developmentally regulated genes. In this example, cells are identified in which a transcriptionally silent gene (or minimally expressed gene) became turned on or enhanced in response to specific treatments or environmental stimuli to the cells. DNA is illustrated schematically in its linear form. Horizontal lines and boxes indicate polynucleotides such as DNA or RNA. Arrows represent promoters. Filled triangles represent site-specific recombination signals. The site-specific recombination signals are depicted in an orientation that promotes excision of the negative selectable marker from the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 13:
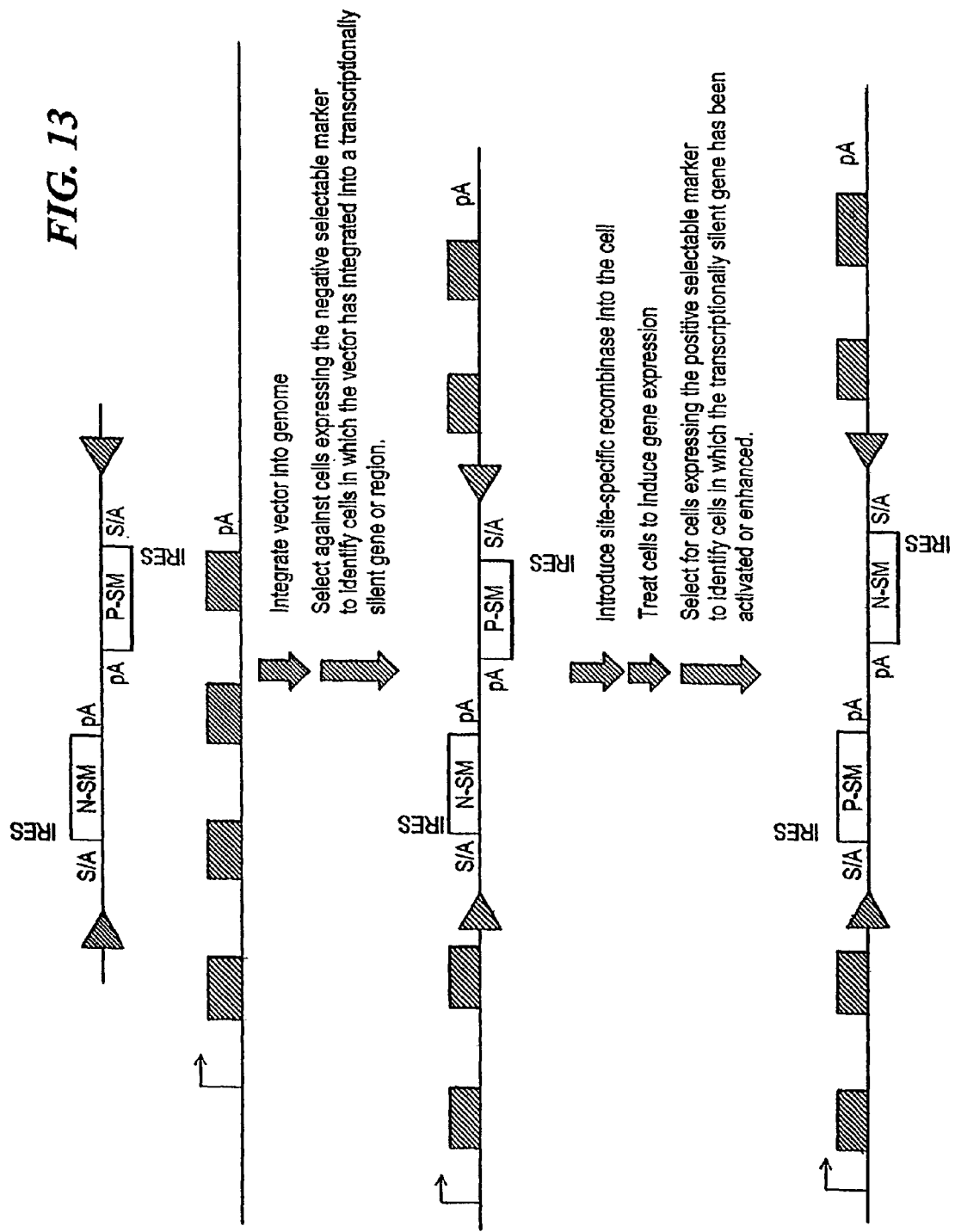

FIG. 13: Method for detecting gene trap insertions that occur in developmentally regulated genes. In this example, cells are identified in which a transcriptionally silent gene (or minimally expressed gene) became turned on or enhanced in response to specific treatments or environmental stimuli to the cells. In other examples, it is possible to identify cells in which a transcriptionally active gene became down regulated or silenced in response to specific treatments or environmental stimuli to the cells. This is accomplished using the vector shown in this figure in combination with the selection scheme shown in FIG. 11 (i.e. selection for the positive selectable marker, then treatment of cells with an agent capable of altering its expression pattern, and selecting against cells expressing the negative selectable marker). DNA is illustrated schematically in its linear form. Horizontal lines and boxes indicate polynucleotides such as DNA or RNA. Arrows represent promoters. Filled triangles represent site-specific recombination signals. The site-specific recombination signals are depicted in an orientation that promotes inversion of the positive and negative selectable markers within the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 14:
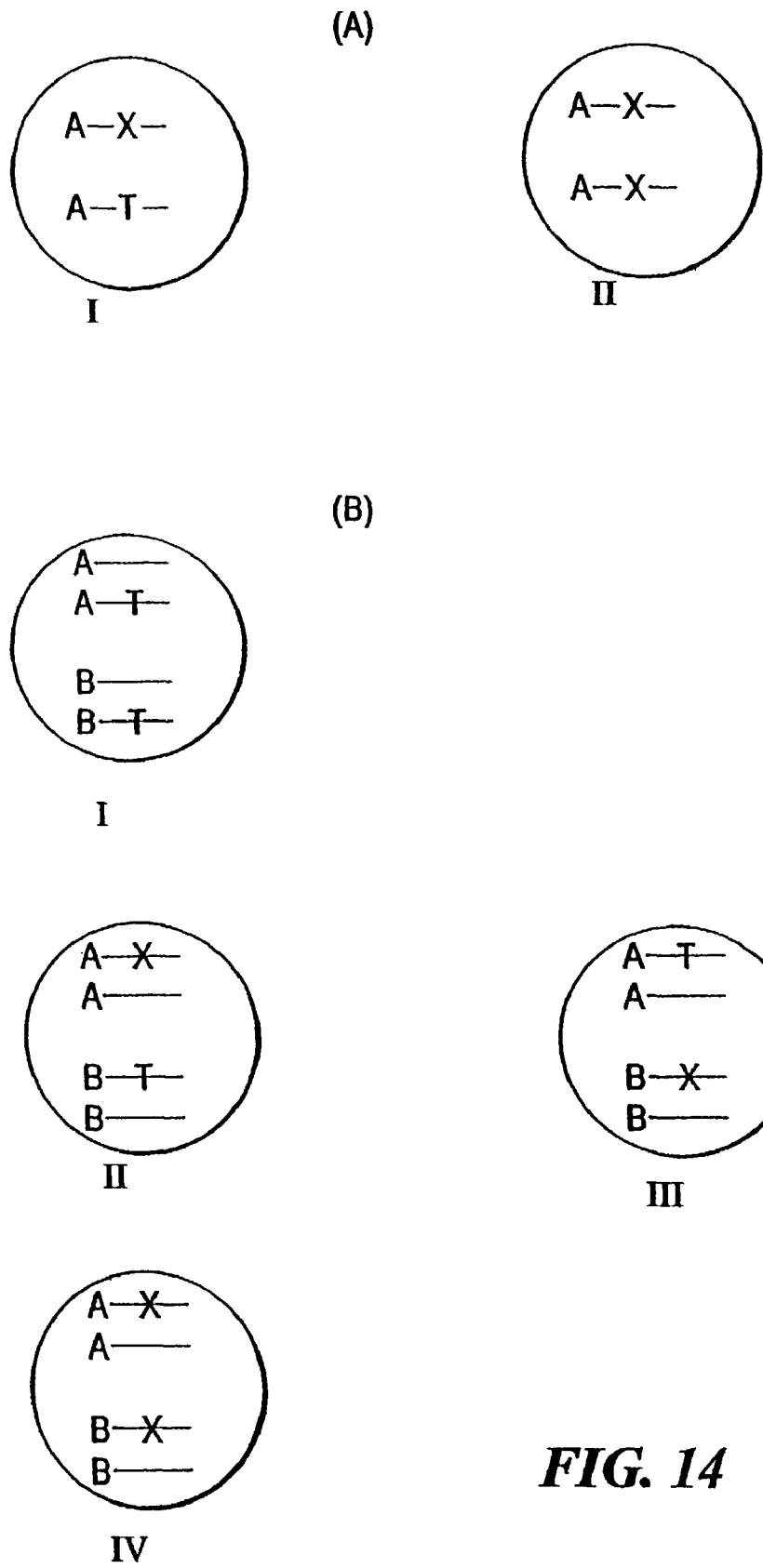
Figure 14:
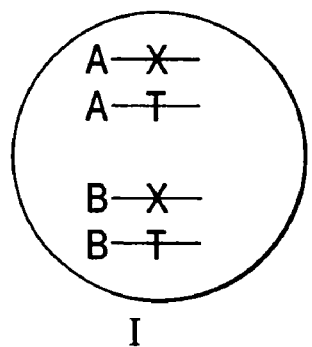
Figure 14:
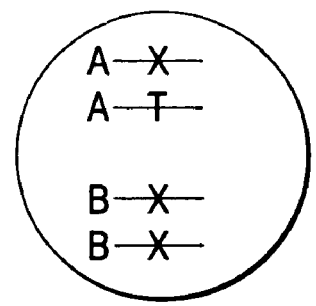
Figure 14:
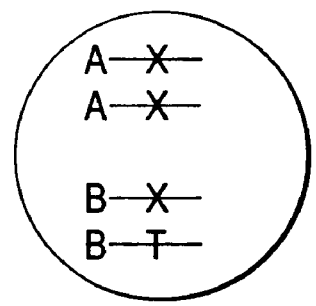
Figure 14:
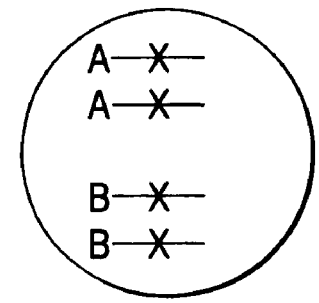

FIG. 14: The Figure schematically shows non-limiting examples of cells that result from mutagenesis according to the present invention and examples of how genes could be tagged for detection. "X" denotes a physicochemical event. "T" denotes a tag introduced by insertional mutagenesis event.

(A) Phenotype results from homozygous mutation of single gene. Both copies of gene A contain a mutation. The gene can be identified by the tag on one copy. Only one cell is required to identify the gene responsible for the phenotype (I). Cell II can be discarded.

(B) Phenotype results from heterozygous mutation of two different genes. Cell I allows identification, in the same cell, of the two genes responsible for the phenotype. Cells II and III are used in combination to identify both genes responsible for the phenotype or separately to identify one of the genes responsible for phenotype. Cell IV can be discarded.

(C) Phenotype results from homozygous mutation of two different genes. Cell I allows identification, in the same cell, of the two genes responsible for the phenotype. Cells II and III are used in combination to identify both genes responsible for the phenotype or separately to identify one of the genes responsible for phenotype. Cell IV can be discarded.

Figure 15:
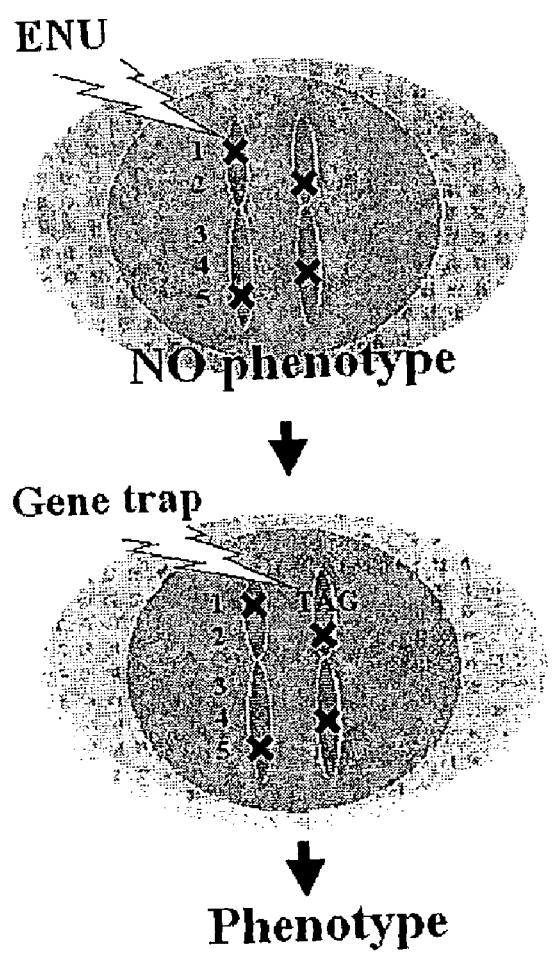

FIG. 15: A schematic representation of a specific example of the combined mutagenesis procedure for efficient mutation and tagging of genes involved in creating a desired phenotype. In Step 1, N-ethyl-N-nitrosourea ENU) creates many mutations per cell. In Step 2, gene trap mutagen knocks out and tags additional alleles in ENU clones to create phenotype and permit identification of the mutated genes.

Figure 16:
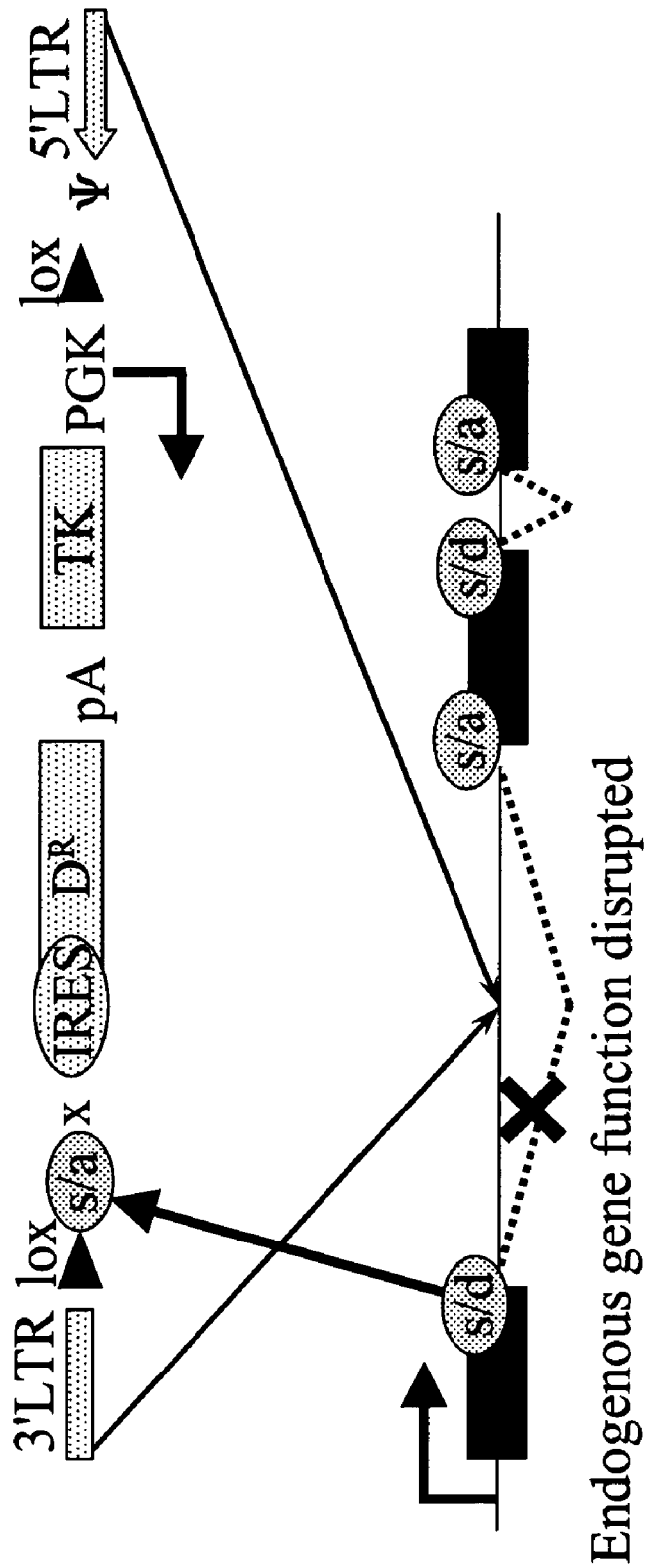

FIG. 16: pDKO2 gene trap knockout vector design and function. Integration of pDKO2 retrovirus traps upstream exons of endogenous gene. The following abbreviations are used in the figure: S/A: branch site and splice acceptor from the intron of an immunoglobulin gene heavy chain variable region obtained by PCR from pCI vector (Promega); x: stop codons in all 3 reading frames; IRES: wild type internal ribosomal entry site from EMCV; obtained by PCR from pE5LVP0 (ATCC#67525); D$^R$: neomycin resistance gene, (pDKO vectors containing other selection markers, such as those conferring resistance to puromycin, hygromycin, or zeocin, have been created in pDKO2 derivatives.); bGHpA: bovine growth hormone polyA sequence; PCR from pcDNA3.1 (Invitrogen); lox: lox71/lox66 sequences, cre recombinase recognition sites; TK: thymidine kinase ORF; PGK: promoter; and ψ: retrovirus packaging signal.

Figure 17:
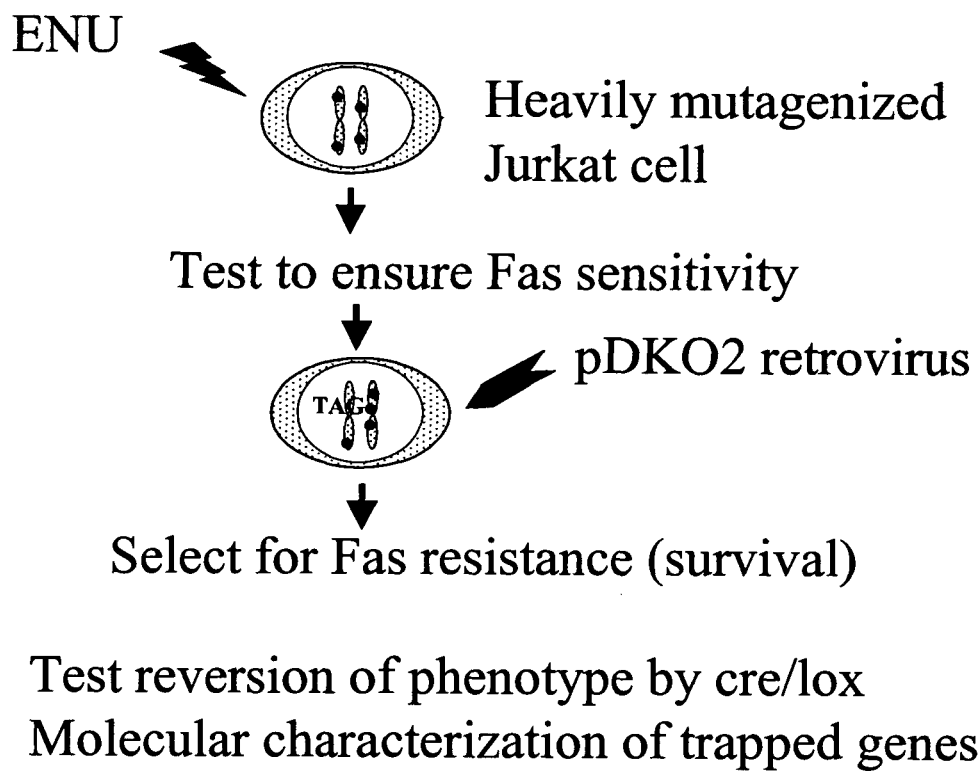

FIG. 17: A schematic representation of a combined mutagenesis screen to identify genes needed for FasL induced apoptosis.

Figure 18:
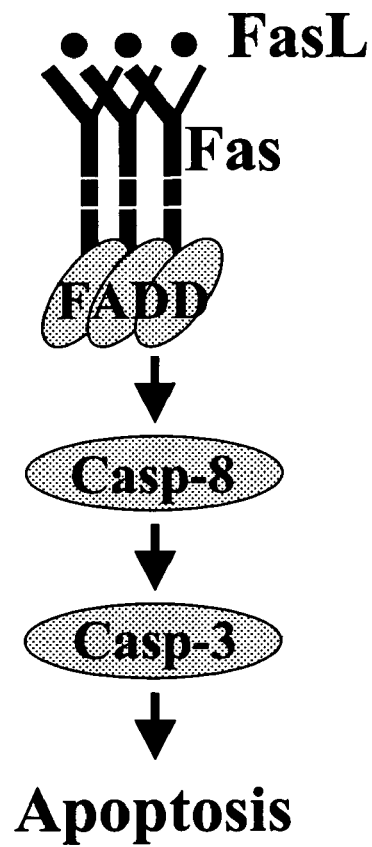
Figure 19:
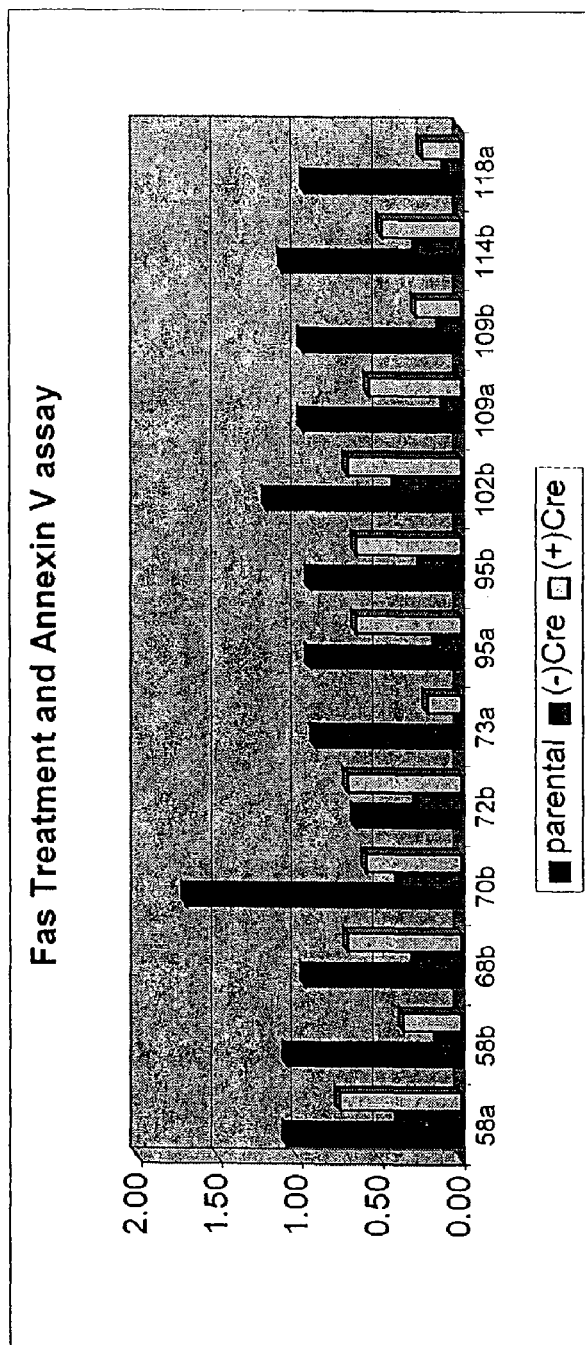

FIG. 18: A schematic representation of the Fas induced apoptosis pathway. To identify gene traps that affect sensitivity to FasL, the doubly mutagenized combined mutagenesis library was selected for clones that exhibited resistance to Fas-induced apoptosis. Under the FasL selection conditions, there is a low spontaneous background FIG. 19: Cre mediated excision of combined mutagenesis gene trap reversion of Fas-resistant phenotype. Clones showing FasL resistance caused by the pDKO2 gene trap were analyzed using RT-PCR, 5'-RACE and inverse PCR to identify the biologically active trapped genes.

DETAILED DESCRIPTION OF THE INVENTION

Definitions

In the description that follows, a number of terms used in recombinant DNA technology are utilized extensively. In order to provide a clear and consistent understanding of the specification and claims, including the scope to be given such terms, the following definitions are provided.

As used herein, the term "physicochemical mutagenesis" means any method of mutating genes that is not insertional mutagenesis (i.e., by insertional mutagen as defined below), such as ionizing radiation and/or chemical approaches to induce one or more mutations in a cell or organism. Physicochemical mutagenesis, therefore, encompasses use of chemical mutagens, radiation (e.g., UV, α radiation, β radiation, γ radiation, x-rays), error prone replication proteins (for example, without limitation, mutant DNA polymerases, such as those that lack a proofreading function), restriction enzymes (used to create DNA breaks and deletions upon introduction into a host cell), and DNA repair mutants and inhibitors (used to enhance mutation from spontaneous and induced mutation). Examples include, but are not limited to, mutant cell lines defective for the genetic complementation groups of xeroderma pigmentosum (XP) known as XP-G and XP-A, the DNA repair protein Ku, and the DNA-dependent protein kinase DNA-PK. An example of a DNA repair inhibitor is $O^6$-BG, an inhibitor of $O^6$-alkylguanine-alkyltransferase. Any physicochemical mutagen can be used alone or in combination with one or more other physicochemical mutagens.

"Insertional mutagenesis", as it relates to the invention, means a process in which a polynucleotide is inserted into the genome of a cell in such a way so as to mutate an endogenous gene. As used herein the terms "incorporation" or "integration" or "insertion" into an endogenous gene are used synonymously.

Insertional mutagenesis can occur when an insertional mutagen is introduced into a cell exogenously and as a result of the exogenous introduction becomes incorporated into the genome so as to mutate one or more endogenous genes. The invention, however, is also directed to mutagenesis events that occur when an endogenous insertional mutagen is caused to insert into locations that are different from the original location. Such is the case when an endogenous transposable element which is induced to further transposition by the action of a transposase. Accordingly, in one embodiment of the invention, insertional mutation of an allele or a gene results from transposition of an endogenous insertional mutagen. This endogenous insertional mutagen may be naturally-occurring in the cell or may have been introduced into the cellular genome or the genome of a precursor cell such as a precursor cell in vitro or precursor cell in vivo.

In one aspect of simultaneous introduction of different mutagens to a cell, one or more of the mutagens is produced endogenously. One or more mutagens is present in the genome of the cell and can provide for further insertion into the genome at one or more new locations. Thus, simultaneous mutagenesis can occur by causing the new insertions of one or more different mutagens from within the cell and can also occur when this endogenous introduction is concurrent in time with the introduction of an exogenous mutagen.

The term "gene disruption" as used herein refers to a gene knock-out or knock-down in which an insertional mutagen is integrated into an endogenous gene thereby resulting expression of a fusion transcript between endogenous exons and sequences in the insertional mutagen.

The mutation can result in a change in the expression level of a gene or level of activity of a gene product. "Activity" encompasses all functions of a gene product, e.g. structural, enzymatic, catalytic, allosteric, and signaling. In one embodiment, mutation results in a decrease or elimination of gene expression levels (RNA and/or protein) or a decrease or elimination of gene product activity (RNA and/or protein). Most mutations will decrease the activity of mutated genes. However, both the insertional and physicochemical mutagens can also act to increase or to qualitatively change (e.g. altered substrate on binding specificity, or regulation of protein activity) the activity of the product of the mutated gene. Although mutations will often generate phenotypes that maybe difficult to detect, most phenotypically detectable mutations change the level or activity of mutated genes in ways that are deleterious to the cell or organism.

The insertional mutagens can also be used to "tag" the mutated gene at least at the DNA level, and in one embodiment, at the RNA or protein level, depending on the insertional mutagen. The mutagenic sequence may by itself be detectable so as to "tag" the insertionally mutated gene or product of the gene.

Thus, as used herein, the term "tag" refers to a structural or functional feature (typically, a nucleotide sequence) contained on an insertional mutagen of the invention, which permits the location of the insertional mutagen to be determined once it has been inserted into a target nucleic acid molecule via recombination (e.g., into the genome of a target cell). The tag, accordingly, not only enables location of the insertional mutagen. It enables the locus into which the vector has inserted to be identified. Examples of tags include, but are not limited to, nucleotide sequences encoding a reporter gene (e.g., β-lactamase, β-galactosidase, luciferase, chloramphenicol acetyl transferase, green fluorescent protein and its derivatives, yellow fluorescent protein and its derivatives, blue fluorescent protein and its derivatives, cyan fluorescent protein and its derivatives, red fluorescent protein and its derivatives, and the like), and nucleotide sequences encoding a selectable marker (which may be a positive selectable marker or a negative selectable marker). It should be recognized however that a tag, for purposes of the invention need not encode a protein. It simply provides a sequence that allows detection of either the tag itself or of a nucleotide sequence adjacent to or otherwise linked to the tagged sequence.

The "tag" can also provide the property that the insertional mutagen can be detected such that a cell containing the insertional mutagen can be detected (and isolated, if desired, or otherwise specifically manipulated).

"5' gene traps" are insertional mutagens that are designed to prevent or reduce functional expression of a given endogenous gene upon insertion of the mutagen into the gene. 5' gene traps alter gene expression by interrupting the normal splicing or exon structure of the primary transcripts of mutated genes. Splicing interruption is accomplished by splicing of upstream exons of the mutated gene onto splice acceptor sequences within the insertional mutagen. This change in splicing often disrupts the protein coding of transcripts of the mutated gene. Alternatively, the insertional mutagen can insert directly into and disrupt the coding potential of exons of the mutated gene.

"3' gene traps" are insertional mutagens that are designed to activate or otherwise enhance transcription of, and optionally translation of, endogenous exons of the gene in which the mutagenic vector is inserted. 3' gene traps function by initiating transcription of mutated genes at promoter sequences located within the insertional mutagen. Transcripts initiated in the mutagenic vector continue 3' of the insertion site to include downstream exons of the mutated gene in chimeric primary transcripts. Exons containing vector sequence can splice onto exons of the mutated gene to generate chimeric transcripts that encode proteins including all or C-terminal fragments of the normal protein product of the mutated gene.

As used herein, "decrease" means that a given gene has been mutated such that the level of gene expression or level of activity of a gene product in a cell or organism is reduced from that observed in the wildtype or non-mutated cell or organism. This is often accomplished by reducing the amount of mRNA produced from transcription of a gene, or by mutating the mRNA or protein produced from the gene such that the expression product is less abundant or less active.

As used herein, and unless otherwise indicated, "a" means one or more.

As used herein, the term "mutated clone" refers to one or more progeny cells arising from a mutated parent cell created with one or both mutagenesis methods of the invention.

As used herein, "homozygous mutant" refers to a cell in which all copies (typically two in most eukaryotic cells, although certain filamentous yeasts, and some higher eukaryotic cell lines, may have more than two copies) of a given gene are mutated.

As used herein, "copies" of genes are also known in the art as "alleles". This latter term signifies the naturally-occurring copy of a given gene in a cell. Usually there are two copies of a gene in a diploid cell. In some situations (e.g., trisomy 21) there are three copies, but four or more copies of one or more entire chromosomes, or extra copies of genes or chromosomal fragments are also encountered naturally. Cells may also be experimentally altered to change the number or expression of specific genes.

The methods and the compositions of the invention may involve insertional mutagens that contain target nucleotide sequences for homologous recombination. As used herein a "target sequence" allows homologous recombination of an insertional mutagenic nucleotide with cellular DNA at a predetermined site on the cellular DNA, the site having homology for sequences in the insertional mutagen, the homologous recombination at the predetermined site resulting in the introduction of the insertional mutagen into the genome and subsequent mutation. A target sequence may have homology where the sequence or sequences within the gene to be mutated or upstream or downstream of the gene to be mutated. The use of targeting sequences has been disclosed in many U.S. patent applications, including U.S. Pat. Nos. 5,641,670, 6,270,989, and 5,733,761, all incorporated by reference for teaching a target sequence.

As used herein, "non-homologous recombination" (which may also be referred to equivalently as "illegitimate recombination") means the joining (exchange or redistribution) of genetic material through a mechanism that does not involve homologous recombination (e.g., recombination directed by sequence homology) and that does not involve site-specific recombination (e.g., recombination directed by site-specific recombination signals and a corresponding site-specific recombinase). Examples of non-homologous recombination include integration of exogenous DNA into chromosomes at non-homologous sites, chromosomal translocations and deletions, DNA end joining, double strand break repair, bridge-break-fusion, concatemerization of transfected polynucleotides, retroviral insertion, and transposition. In most cases, non-homologous recombination is thought to occur through the joining of "free DNA ends." Free ends are DNA molecules that contain an end capable of being joined to a second DNA end either directly, or following repair or processing. The DNA end may consist of a 5' overhang, 3' overhang, or blunt end.

Retroviral vectors integrate into eukaryotic genomes by a distinct mechanism of non-homologous recombination that is catalyzed by the action of the virally encoded integrase enzyme, and the mechanism of viral integration, replication and infection has been well described (reference 0). The mutagenic ability of retroviruses and retroviral vectors and their ability to enable the rapid identification of mutated genes through the linkage of retroviral tag sequences within the transcripts of mutagenized genes are well known in the art (reference 2-5).

General reference for mechanisms of retroviral infection, replication, and integration: 0: In: Retroviruses. Coffin, J M.; Hughes, S H.; Varmus, H E. Plainview (NY): Cold Spring Harbor Laboratory Press; c1997; Use of wildtype retroviruses as mutagens: 1: Varmus H E, Quintrell N, Ortiz S. Cell. 1981 July;25(1):23-36; Use of retrovirus promoter traps as mutagens and to isolate trapped genes: 2: Friedrich G, Soriano P. Methods Enzymol. 1993; 225:681-701; 3: Gossler A, Joyner A L, Rossant J, Skarnes W C. Science. 1989 Apr. 28;244(4903):463-5; 4: Friedrich G, Soriano P. Genes Dev. 1991 September;5(9):1513-23; 5: von Melchner H, DeGregori J V, Rayburn H, Reddy S, Friedel C, Ruley H E. Genes Dev. 1992 June ;6(6):919-27; Randomness of retroviral insertion: 6: King W, Patel M D, Lobel L I, Goff S P, Nguyen-Huu M C. Science. 1985 May 3;228(4699):554-8; 7: Hubbard S C, Walls L, Ruley H E, Muchmore E A. J Biol Chem. 1994 Feb. 4;269(5):3717-24.

Like retroviruses, transposons and transposon vectors can also be used to integrate sequences that an act as insertional mutagens. Also like retroviruses, transposons integrate by enzymatically catalyzed non-homologous recombination in which transposase enzymes catalyze the genomic integration and transposition of transposon DNA (reference 1, 2, 12, 13). Numerous transposons have been characterized that function in insects (reference 13-15), plants (reference 16-20) and vertebrates (including mammals, reference 3-12). In particular, the TC1/mariner derivative transposon, Sleeping Beauty, has been demonstrated to integrate efficiently in mammals. Transposons have been shown to function as efficient insertional mutagens in numerous systems (reference 5, 15, 17, 24-26), and to exhibit broad target specificity (reference 21-23). Transposase catalyzes SB transposition and integration: 1: Cui Z, Geurts A M, Liu G, Kaufman C D, Hackett P B. J Mol Biol. 2002 May 17;318(5):1221-35; 2: Izsvak Z, Khare D, Behlke J, Heinemann U, Plasterk R H, Ivics Z. J Biol Chem. 2002 Jun. 24, SB transposon can transpose and act as an insertional mutagen in mammals: 3: Dupuy A J, Clark K, Carlson C M, Fritz S, Davidson A E, Markley K M, Finley K, Fletcher C F, Ekker S C, Hackett P B, Horn S, Largaespada D A. Proc Natl Acad Sci USA. Apr. 2002 2;99(7):4495-9; 4: Horie K, Kuroiwa A, Ikawa M, Okabe M, Kondoh G, Matsuda Y, Takeda J. Proc Natl Acad Sci USA. 2001 Jul. 31;98(16):9191-6; 5: Dupuy A J, Fritz S, Largaespada D A. Genesis. 2001 June;30(2):82-8; 6: Fischer S E, Wienholds E, Plasterk R H. Proc Natl Acad Sci USA. 2001 Jun. 5;98(12):6759-64; 7: Ivics Z, Hackett P B, Plasterk R H, Izsvak Z. Cell. 1997 Nov. 14;91(4):501-10. Other transposons also function in mammals: 8: Zagoraiou L, Drabek D, Alexaki S, Guy J A, Klinakis A G, Langeveld A, Skavdis G, Mamalaki C, Grosveld F, Savakis C. Proc Natl Acad Sci USA. 2001 Sep. 25;98(20):11474-8; 9: Sherman A, Dawson A, Mather C, Gilhooley H, Li Y, Mitchell R, Finnegan D, Sang H. Nat Biotechnol. 1998 November;16(11):1050-3; 10: Kawakami K, Shima A, Kawakami N. Proc Natl Acad Sci USA. 200 Oct. 10;97(21):11403-8; 11: Fadool J M, Hartl D L, Dowling J E. Proc Natl Acad Sci USA. Apr. 1998 28;95(9):5182-6; 12: Plasterk R H. Cell. 1993 Sep. 10;74(5):781-6. P elements developed as insertional mutagen in invertebrates: 13: Kaufman P D, Rio D C. Nucleic Acids Res. 1991 Nov. 25;19(22):6336; 14: Rubin G M, Spradling A C. Nucleic Acids Res. 1983 Sep. 24;11(18):6341-51; 15: Spradling A C, Rubin G M. Science. 1982 Oct. 22;218(4570):341-7. Ac and Ds and other plant transposons transpose, integrate and are used as insertional mutagens in plants: 16: Grevelding C, Becker D, Kunze R, von Menges A, Fantes V, Schell J, Masterson R. Proc Natl Acad Sci USA. 1992 Jul. 1;89(13):6085-9; 17: Walbot V. Curr Opin Plant Biol. 2000 April;3(2):103-7; 18: Pereira A, Aarts M G. Methods Mol Biol. 1998;82:329-38; 19: Cooley M B, Goldsbrough A P, Still D W, Yoder J I. Mol Gen Genet. 1996 Aug. 27;252(1-2):184-94; 20: Bhatt A M, Page T, Lawson E J, Lister C, Dean C. Plant J. 1996 June;9(6):935-45. P element transposon can integrate broadly throughout genomes: 21: Kassis J A, Noll E, Van-Sickle E P, Odenwald W F, Perrimon N. Proc Natl Acad Sci USA. 1992 Mar. 1;89(5):1919-23; 22: Berg C A, Spradling A C. Genetics. 1991 March;127(3):515-24; 23: Tower J, Karpen G H, Craig N, Spradling A C. Genetics. 1993 February;133(2):347-59; 24: Cooley L, Berg C, Kelley R, McKearin D, Spradling A. Prog Nucleic Acid Res Mol Biol. 1989; 36:99-109; 25: Cooley L, Kelley R, Spradling A. Science. 1998 Mar. 4;239(4844):1121-8; 26: Spradling A C, Stern D M, Kiss I, Roote J, Laverty T, Rubin G M. Proc Natl Acad Sci USA. 1995 Nov. 21;92(24):10824-30.

As used herein, the term "phenotype" means any property of a cell or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), profile of secreted or cell surface proteins, (e.g., bacterial or viral) infection, post-translational modifications, protein localization within the cell (e.g. translocation of a protein from the cytoplasm to the nucleus), profile of secreted or cell surface proteins, cell proliferation, signal transduction, metabolic defects or enhancements, transcriptional activity, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wild-type or (non-mutated) cell or organism (e.g., a cell or organism that in which the gene(s) have not been mutated).

As used herein, the term "multiploid" means any ploidy greater than haploid. Multiploid encompasses diploid, triploid, tetraploid, and aneuploid.

As used herein "library" means more than one cell. A library may be cells subjected to one or both mutagenesis methods, singly or more than one time. Thus a library includes, but is not limited to, one or more clones of mutated cells or mutated cells where each cell has a different set of mutations. Libraries provide a source of cells to subject to mutagenesis and a source of cells to screen for desired phenotypes following mutagenesis.

A "known" gene is directed to the level of characterization of a gene. The invention allows expression of genes that have been characterized, as well as expression of genes that have not been characterized. Different levels of characterization are possible. These include detailed characterization, such as cloning, DNA, RNA, and/or protein sequencing, and relating the regulation and function of the gene to the cloned sequence (e.g., recognition of promoter and enhancer sequences, functions of the open reading frames, introns, and the like). Characterization can be less detailed, such as having mapped a gene and related function, or having a partial amino acid or nucleotide sequence, or having purified a protein and ascertained a function. Characterization may be minimal, as when a nucleotide or amino acid sequence is known or a protein has been isolated but the function is unknown. Alternatively, a function may be known but the associated protein or nucleotide sequence is not known or is known but has not been correlated to the function. Finally, there may be no characterization in that both the existence of the gene and its function are not known. The invention allows expression of any gene at any of these or other specific degrees of characterization.

The invention could also be practiced with a combination of physicochemical or insertional mutation with epigenetic techniques for modifying genome function, such as modification of methylation, is RNA antisense RNA, ribozymes, transcription factors designed to activate or inactivate multiple transcriptional regulatory sequences, modifiers of chromosomal proteins, such as histones, that modify the transcriptional availability of multiple genes.

Overview

The ability to create tagged mutations in multiple genes in multiploid cells and multicellular organisms would have utility in many areas, including correlating a phenotype with the genes responsible for it by gene identification, gene discovery, determining gene function, creating phenotypes, discovering drug targets, and making human disease models in cells and in multicellular organisms.

The ability to create tagged homozygous mutations in a cell or multicellular organism enables alteration of the genetic make up of a cell and has numerous uses, such as those above as well as correcting genetic defects. The in vitro, ex vivo, and in vivo potential uses of this technology are enormous and will be readily apparent to the skilled artisan.

The present invention, therefore, is directed to methods for mutating a single gene or multiple genes (e.g., two or more) in eukaryotic cells and multicellular organisms. The invention also is directed to insertional mutagens for making the mutant cells and organisms, and which also can be used to analyze the mutations that are made in the cells and organisms. The invention also is directed to methods in which one or more mutated genes is tagged by a tag provided by the insertional mutagen to allow the detection, selection, isolation, and manipulation of a cell with a genome tagged by the insertional mutagen and allows the identification and isolation of the mutated gene(s).

The invention provides methods for making multiple mutations (i.e., mutations in two or more genes that produce a phenotype cumulatively) in cells and organisms and tagging at least one of the mutated genes such that it can be rapidly recovered and identified. Creation of multiple mutations in a cell where at least one of the mutations is tagged is useful in studying gene function. One reason for this is that many phenotypes require multiple gene mutations in order to be manifested. Current methods do not allow for creation of multiple mutations in a cell in a manner that allows easy identification of the mutated genes. The present invention enables multiple mutations to be created in the same cell and allows at least one of the mutations to be tagged.

Libraries that contain the cells mutagenized by a combination of insertional mutagenesis and physicochemical mutagenesis can be screened for a phenotype of interest. In cells that have the phenotype of interest, one or more tagged genes can be identified and validated as being responsible for the particular phenotype of interest.

The invention also provides methods for making homozygous mutations in eukaryotic cells and organisms. The homozygously mutated gene is tagged by an insertional mutagen so that it can be identified and, if desired, recovered. Homozygous mutations are useful for discovering functions associated with the mutated gene.

The methods of the present invention can be used to mutate any eukaryotic cell, including, but not limited to, haploid (in the case of multiple gene mutations), diploid, triploid, tetraploid, or aneuploid. In one embodiment, the cell is diploid. Cells in which the methods of the present invention can be advantageously used include, but are not limited to, primary cells (e.g., cells that have been explanted directly from a donor organism) or secondary cells (e.g., primary cells that have been grown and that have divided for some period of time in vitro, e.g., for 10-100 generations). Such primary or secondary cells can be derived from multi-cellular organisms, or single-celled organisms. The cells used in accordance with the invention include normal cells, terminally differentiated cells, or immortalized cells. (including cell lines, which can be normal, established or transformed), and can be differentiated (e.g., somatic cells or germ cells) or undifferentiated (e.g., multipotent, pluripotent or totipotent stem cells).

Examples of tissues from which cells can be isolated for use in the present invention include, without limitation, neuronal tissue (including tissue from the central and peripheral nervous systems), hematopoietic tissue, lymphatic tissue, immune tissue, bone tissue, stromal tissue (including, e.g., bone marrow tissue), mesenchymal tissue, mesothelial tissue, connective tissue (including e.g., cartilage, dermal tissue, subcutaneous tissue, adipose tissue, etc.), endothelial tissue, epithelial tissue, lung tissue, skin tissue, kidney tissue, gastrointestinal tissue (including esophagus, stomach, intestine, etc.), brain tissue, heart tissue, pancreatic tissue, muscle tissue, liver tissue, gonadal tissue, embryonic tissue including embryonic stem cells and embryonic germ cells), zygote tissue, embryonic, and other cells and tissue known in the art.

A variety of cells isolated from the above-referenced tissues, or obtained from other sources (e.g., commercial sources or cell banks), can be used in accordance with the invention. Non-limiting examples of such cells include somatic cells such as blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes.

The eukaryotic cells used in the methods of the present invention can be animal cells, plant cells (monocot or dicot plants) or fungal cells, such as yeast. Animal cells include those of vertebrate or invertebrate origin. Vertebrate cells are of particular use in the present invention, especially mammalian cells (including, but not limited to, cells obtained or derived from human, simian or other non-human primate, mouse, rat, avian, bovine, porcine, ovine, canine, feline and the like), avian cells, fish cells (including zebrafish cells), insect cells (including, but not limited to, cells obtained or derived from Drosophila species, from Spodoptera species (e.g., Sf9 obtained or derived from *S. frugiperida*, or HIGH FIVE™ cells) or from Trichoplusa species (e.g., MG1, derived from *T. ni*)), worm cells (e.g., those obtained or derived from *C. elegans*), and the like. It will be appreciated by the ordinarily skilled artisan, however, that cells from any species besides those specifically disclosed herein can be advantageously used in accordance with the methods of the present invention, using art-known methods in conjunction with those described herein and without the need for undue experimentation.

Cell lines are also useful in the present invention. Examples of useful cell lines include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (see Van der Blick, A. M. et al., *Cancer Res.* 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) can also be used. Other mammalian cells and cell lines can be used in accordance with the present invention, including but not limited to CHO cells, COS cells, VERO cells, 293 cells, PER-C6 cells, M1 cells, NS-1 cells, COS-7 cells, MDBK cells, MDCK cells, MRC-5 cells, WI-38 cells, WEHI cells, SP2/0 cells, BHK cells (including BHK-21 cells); these and other cells and cell lines are available commercially, for example from the American Type Culture Collection (P.O. Box 1549, Manassas, Va. 20108 USA). Many other cell lines are known in the art and will be familiar to the ordinarily skilled artisan; such cell lines therefore can be used equally well in the methods of the present invention.

The present invention can be practiced using plant cells. Methods for culturing plant cells, insertionally mutating plant cells, and producing transgenic plants are known in the art (see, e.g., Hall, Robert D., *Plant Cell Culture Protocols*, Humana Press, New Jersey (1999); Gartland and Davey, *Agrobacterium Protocols*, Humana Press, New Jersey (1995); each incorporated herein by reference for teaching methods of culturing, transfecting, mutating, and producing transgenic plants and plant cells).

In certain embodiments of the invention, cells can be mutated within the organism or within the native environment as in tissue explants (e.g., in vivo or in situ). Alternatively, tissues or cells isolated from the organism using art-known methods and genes can be mutated according to the present methods. The tissues or cells are either maintained in culture (e.g., in vitro), or re-implanted into a tissue or organism (e.g., ex vivo).

Methods of Making Mutant Cells

The invention involves two types of mutagenesis events—physicochemical and insertional. In one aspect, multiple genes are mutated which cumulatively produce a desired phenotype. The mutations can be homozygous, heterozygous, or a combination of the two. One or more of these genes is tagged by means of an insertional mutagen. A single cell can contain all of the tagged genes or less than all of the tagged genes, for example, one tagged gene. Accordingly, in a non-limiting example two mutated genes in the same cell are required to produce the desired phenotype. Cells are mutated to produce the phenotype, screened for the desired phenotype and two cells are selected that have the phenotype because both genes are mutated in each cell. One gene is tagged in one cell and the other gene is tagged in the second cell. This process allows the identification of both genes that cumulatively produce the desired phenotype even though only one gene was tagged in each cell.

Furthermore, the present invention is useful even if only one gene responsible for a phenotype is identified. Such a gene could form a target for modulating the phenotype. This is useful, for example, in drug discovery and in production of useful gene products. Accordingly, one or more of multiple genes required to produce a desired phenotype can be identified using the mutagenic methods of the invention.

The invention also involves using the mutagenic methods to produce a desired phenotype that results from the homozygous mutation of a single gene. At least one of the mutated alleles is tagged.

The mutation process involves at least one physicochemical mutagenic event, and at least one insertional mutagenic event, which can be carried out in any order or simultaneously.

Physicochemical Mutagenesis

One phase of the mutational methods of the present invention involves physicochemical mutagenesis of a cell or organism by one or more physicochemical mutagens. In one embodiment, physicochemical mutagenesis is the initial event in the mutagenic process. In another embodiment, it can be performed simultaneously with an insertional mutagenesis event. In another embodiment it follows an initial insertional mutagenesis event. In any of these embodiments one or more further physiochemical and/or insertional mutagenesis events can be carried out in any order and simultaneously.

Physicochemical mutagenesis can be achieved by a variety of mutagenic agents. Examples of mutagenic agents known in the art include, but are not limited to, chemical mutagens (e.g., DNA-intercalating or DNA-binding chemicals which affect (e.g., increase or decrease) the activity, protein coding potential or expression of a gene contained on a DNA molecule to which the chemical has bound), physical mutagens (e.g., UV light, ionizing radiation, (gamma, beta and alpha radiation, x-rays), biochemical mutagens (e.g., restriction enzymes, DNA repair mutagens, DNA repair inhibitors, and error-prone DNA polymerases and replication proteins), and the like. The mutagenic changes in DNA sequence can occur as a direct consequence of the mutagen/DNA interaction. Alternatively DNA repair mechanisms induced in response to damage inflicted by the mutagen may participate in implementing mutations.

In certain embodiments, chemical mutagenesis is used to induce mutation in one or more genes in the target cell or organism. An example of a chemical mutagen commonly used to mutate cells and organisms is N-ethyl-N-nitrosourea (ENU). Other examples of chemical mutagens useful in the present invention include, but are not limited to, ethylmethanesulphonate (EMS) and ICR191. Many other chemical mutagens are known in the art and are useful in the present invention (see, e.g., E. C. Friedberg, G. C. Walker, W. Siede, *DNA Repair and Mutagenesis*, ASM Press, Washington D.C. (1995); 1: Justice M J, Zheng B, Woychik R P, Bradley A. Methods. 1997 December;13(4):423-36; 2: Gasparro F P, Felli A, Schmitt I M. Recent Results Cancer Res. 1997; 143: 101-27; 3: Vogel E W, Natarajan A T. Mutat Res. 1995 August;330(1-2):183-208; 4: Anderson P. Methods Cell Biol. 1995; 48:31-58; 5: Russell L B. Environ Mol Mutagen. 1994; 23 Suppl 24:23-9; 6: DeMarini D M, Brockman H E, de Serres F J, Evans H H, Stankowski L F Jr, Hsie A W. Mutat Res. 1989 January;220(1):11-29; 7: Wood R D, Sedgwick S G. Mutagenesis. 1986 November;1(6):399-405; 8: Loprieno N, Barale R, Von Halle E S, von Borstel R C. Mutat Res. 1983 June;115(2):215-23; 9: Bradley M O, Bhuyan B, Francis M C, Langenbach R, Peterson A, Huberman E. Mutat Res. 1981 September;87(2):81-142; 10: Hoffmann G R. Mutat Res. 1980 January;75(1):63-129; 1: Flessel C P. Adv Exp Med Biol. 1977; 91:117-28; 12: McCann J, Ames B N. Proc Natl Acad Sci USA. March 1976; 73(3):950-4; 13: Orias E, et. al. Methods Cell Biol. 1976; 13:247-82; 14: Kilbey B J. Methods Cell Biol. 1975; 12:209-31 incorporated herein by reference for teaching chemical mutagens and their use in inducing gene mutation in various cells and organisms).

Preferred doses of chemical mutagens for inducing mutations in cells and organisms are described elsewhere herein, are known in the art, or can be readily determined by the ordinarily skilled artisan using assays of mutagenesis described herein or known in the art. Chemical mutagenesis of cells in vitro can be achieved by treating the cells with various doses of the mutagenic agent and/or controlling the time of exposure to the agent. By titrating the mutagenic agent exposure and/or dose, it is possible to carry out the optimal degree of mutagenesis for the intended purpose, thereby mutating a desired number of genes in each cell. Examples of useful doses of ENU are 0.1-0.4 mg/ml for 1-2 hours. Examples of useful doses of EMS are 0.1-1 mg/ml for 10-30 hours. While the treatment conditions described herein are known to be useful in accordance with the present invention, lower and higher doses and exposure times can be used to achieve the desired mutation frequency. In addition, optimal doses and exposure times will vary from cell type to cell type and can be readily determined using the methods of the invention, knowledge that is readily available in the art, and routine experimentation. Other chemical mutagens and mutagenic agents are used at doses known in the art or determined through routine experimentation.

Physicochemical mutagenesis can be carried out using a single mutagenic agent. Alternatively, physicochemical mutagenesis can be carried out using multiple (more than one) mutagenic agents. When multiple mutagenic agents are used, mutagenesis can be carried out by exposing the cells to the agents at the same time or sequentially. Physicochemical mutagenesis of a given cell or organism can also be carried out in a single exposure or in multiple sequential exposures, in any order.

If physicochemical mutagenesis of a cell or organism is performed prior to another mutagenic event (e.g., insertional mutagenesis or another round of physicochemical mutagenesis) carried out on the same cell or organism, the mutation frequency in the physicochemically mutated cell or organism optionally can be determined prior to or following the additional mutagenic event (e.g., prior to or following insertional mutagenesis or the next round of physicochemical mutagenesis). This approach allows the artisan to select the mutagenic agent and conditions that achieve the desired mutation frequency.

Mutation frequency obtained with a particular mutagen can be assessed using a number of methods described herein and known in the art. One such method is to test for gene function of a selectable or screenable marker within the cell. Typically, the marker used in this approach exists in the cell as a single copy gene; however, multi-copy genes could be useful in such methods, particularly to assess high mutation frequencies. The marker gene can be a cellular gene, such as HPRT, or could be an exogenously introduced gene, such as HSV-thymidine kinase, green fluorescent protein, luciferase, β-galactosidase, a cell surface protein suitable for FACS sorting, and the like. Following mutagenesis, the artisan can assay for the absence of, or reduction in, marker gene expression or activity. For example, mutation frequency can be assessed in mutagenized cells by selecting against HPRT (endogenous HPRT is X-linked and therefore, there is normally only one functional copy in a given cell) or HSV-TK (in cells transfected with a single copy of the HSV-TK gene) using selection with 6-thioguanine (6-TG) and 1,2'-deoxy-2'-fluoro-o-D-arabinofuranosyl-5-iodouracil (FAIU), respectively. The number of surviving clones divided by the total number of clones plated then defines the mutation frequency for single copy genes. Thus, a desired mutation frequency can be obtained in any cell or organism by mutagenizing cells under several conditions, assaying for marker activity, and determining mutation frequency. With respect to the other marker examples described above, and those known in the art, any suitable assay can be used to test for loss of marker function (or gain of function) including enzyme assays, ELISA, and FACS. Once a desired level of mutation in a cell population is obtained, one or more cells from that population can be used in the second phase of the process, as described below.

Another method for assessing mutation frequency is to amplify (e.g., via PCR) a genomic locus or cDNA from one cell (or a population of cells) and clone the amplification product(s), and sequence the cloned nucleotides. By comparing the sequence from the mutagenized cell to the sequence from the wild-type (non-mutagenized) cell, it is possible to determine the number of mutations per unit length, (e.g., one mutation per 1000 bp). A variety of permutations of this method, and similar methods, will be readily apparent to a person of skill in the art. Thus, this assay can be used to select mutagenesis conditions that give rise to a desired mutation frequency.

The present invention involves mutagenizing cells with physicochemical mutagens, such as those mutagens that are well-known in the art and that therefore will be familiar to the ordinarily skilled artisan, such that one or more genes are mutagenized in each cell.

Any number of genes can be mutagenized in each cell. To select a mutation frequency and library coverage, it is useful to consider that there is a relationship between the total number of genes contained in the genome of the cell, the number of mutated genes produced in each cell, the number of mutated cells generated, and the complexity of the library. In general, as the number of genes in a cell increases (e.g. yeast versus mammalian cells), the number of mutations per cell or the number of mutated cells (or both) must increase in order to produce the same library coverage.

As a general guideline, creation of a larger number of mutations per cell reduces the number of cells required to produce a library of cells in which every gene in the genome has been mutated, on average, at least one time. Likewise, as the mutation frequency increases, the size of the library can decrease without affecting its coverage. For example, if one copy of a given gene is mutated at a frequency of approximately 1 cell out of 100 surviving mutagenized cells, then 100 mutant cell clones will be necessary to produce a library in which one copy of each gene has been mutated, on average, one time. However, if one copy of a gene is mutated at a frequency of 1 cell in 30 cells, then only 30 mutant clones are necessary to produce the same 1×library. A library of this size can be referred as a 1×library to indicate that one copy of each gene has been mutated one time, on average.

In preferred embodiments, at least 50-10,000 (one mutated copy of 0.05-10% of the total number of alleles in the diploid genome) genes are mutated in each cell. In highly preferred embodiments, at least 250-5,000(one mutated copy of 0.25-5% of the total number of alleles in the diploid genome) genes are mutated in each cell. In other embodiments, it is useful to mutate 10-100 genes in each cell. In still other embodiments, it is useful to mutate 10,000-50,000 genes, or more. As the number of mutations per cell increases it becomes increasingly likely that both alleles of some genes will be mutated as well as becoming increasingly likely that multiple genes that are needed for a particular biological function will be mutated in a single cell. Thus mutagenizing a cell can sensitize this cell or libraries of similarly mutagenized cells to the induction of phenotypes as a consequence of further mutation (e.g. insertional mutagenesis) on this sensitized genetic background.

It should be noted that a 1×library is only an estimate of library complexity. Statistically, assuming a random mutation frequency, a 1×library will contain about 66% of the genes with a single mutation. Some genes may be mutated twice (where the genome in the cell is diploid) and others will not be mutated. To increase the probability that most or all genes in a given library are mutated at least once, a library of increased complexity can be used (e.g., a 5×or 10×library can be used). In other embodiments that do not require mutation of every gene in a genome, libraries of less complexity can be created (e.g., a 0.1×(or less) library).

It is also possible to estimate library size and coverage by assessing the mutation frequency of individual genes in the library. For example, if HPRT and HSV-TK are both mutated at a frequency of 1 in 500 cells under a specific mutation condition, then a 1×library could be estimated to contain 500 cells. Such libraries of increased or decreased complexity can be created by manipulating the conditions of physicochemical mutagenesis to which the cells are exposed, e.g., by increasing the dose and/or exposure time of the physicochemical mutagen(s) to make libraries of increased complexity, or by decreasing the dose and/or exposure time of the physicochemical mutagen(s) for preparation of libraries of decreased complexity.

If physicochemical mutagenesis is carried out prior to insertional mutagenesis, the physicochemically mutated cells or organism optionally can be screened at this time for a desired phenotype. This screening can be done whether or not the mutation frequency in the physicochemically mutated cells is determined. Mutant cells that display the desired phenotype prior to insertional mutagenesis can then be discarded; it is desirable to remove cells displaying the desired phenotype at this stage since they would interfere with subsequent screening by displaying the desired phenotype independent of insertional mutagenesis. As disclosed herein, insertional mutagenesis provides a way to tag a gene that is involved in the induction of a desired phenotype. If the phenotype is already produced by the physicochemical mutagenesis of a gene, then an insertional tag cannot be used to correlate the tagged gene with the phenotype since the phenotype is not induced by the insertion event. Thus, in one embodiment of the present invention, cells are assayed for desired phenotypes prior to insertional mutation to identify and remove cells that have acquired the phenotype without insertional mutagenesis.

In another embodiment of the invention where physicochemical mutagenesis is carried out prior to insertional mutagenesis, phenotypes are not assessed prior to insertional mutation because it is unlikely that the desired phenotype will be produced. In this embodiment, it is preferable to mutate cells under conditions that yield a low number of mutations per cell because it is unlikely that the desired phenotype will be produced. The reason for this is that when a large number of mutations are made in each cell, for example 10,000 mutated genes per cell, the probability of mutating two genes or alleles to create a phenotype is relatively high. Conversely, when a small number of mutations is made in each cell, for example 100 mutated genes per cell, the probability of mutating two or more required genes or alleles in the same cell to create a phenotype is low. Furthermore, the number of physicochemically mutated cells selected for insertional mutagenesis also impacts the probability that a cell will be selected that has the phenotype prior to insertional mutagenesis. For example, if 1,000 mutations are created in each cell by physicochemical mutagenesis, but only one cell is selected for insertional mutagenesis, the probability that this one cell possesses the desired phenotype can be relatively low. On the other hand, if 10 gene mutations are created in each cell by physicochemical mutagenesis, but $10^6$ physicochemically mutated clones are selected for insertional mutagenesis, then the probability that one or more cells possess the desired phenotype prior to insertional mutagenesis can be relatively high. Thus, there is a correlation between the number of physicochemical mutations per cell, the number of physicochemically mutated cells selected for insertional mutagenesis, and the probability of selecting one or more cells displaying a phenotype prior to insertional mutagenesis. One method for empirically assessing this relationship for a given phenotype is to physicochemically mutate cells under several conditions and then test for the phenotype frequency prior to insertional mutagenesis. If, for example, the phenotype frequency for a particular physicochemical mutation is found to be 1 mutant phenotype observed per 1000 cells, by selecting 50 cells there is only approximately a 5% probability of selecting a cell displaying the phenotype of interest. Another approach for assessing the likelihood of selecting a physicochemically mutated cell displaying the desired phenotype is to determine the mutation frequency in a given population of mutated cells using one of the assays described above (e.g., using HPRT or HSV-TK selection assays). If, for example, the mutation frequency for a single copy gene is 1 mutation in 400 clones, then the probability of mutating both alleles of a gene in a diploid cell is roughly 1 in 160,000 ($\frac{1}{400} \times \frac{1}{400}$). By selecting 4000 cells for insertional mutagenesis, the probability of cells displaying a phenotype caused by a homozygous gene mutation is, therefore, relatively low.

The foregoing assays for determining mutation frequency are intended as non-limiting examples provided solely to impart guidelines to the artisan for selecting cells for insertional mutagenesis. As the ordinarily skilled artisan will be aware, there are a number of other assays of mutation frequency that can be employed in conjunction with the present invention; the exemplary assays described herein therefore should not be construed as limiting the scope of the invention in any way.

Insertional Mutagenesis

The other mutational method of the present invention is insertional mutagenesis of a cell or organism by one or more insertional mutagens (which can be the same or different). In one embodiment, insertional mutagenesis is the initial mutagenic event and precedes a physicochemical mutagenic event. In another embodiment, insertional mutagenesis is carried out simultaneously with physicochemical mutagenesis. In another embodiment, an insertional mutagenesis event follows a physicochemical mutagenesis event. In any of these embodiments, the cells can subsequently be subjected to one or more additional physicochemical mutagenesis events, one or more additional insertional mutagenesis events, or a combination of any number of these events in any order or simultaneously. The coupling of insertional mutagenesis with one or more additional mutational events provides the ability to create mutations, in cells or organisms, that have previously been difficult or impossible to produce or to detect.

According to the invention, insertional mutagenesis involves the integration of one or more polynucleotide sequences into the genome of a cell or organism to mutate one or more endogenous genes in the cell or organism. Thus, the insertional mutagenic polynucleotides of the present invention are designed to mutate one or more endogenous genes when the polynucleotides integrate into the genome of the cell.

Insertional Mutagens

Accordingly, the insertional mutagens used in the present invention can comprise any nucleotide sequence capable of altering gene expression levels or activity of a gene product upon insertion into DNA that contains the gene. The insertional mutagens can be any polynucleotide, including DNA and RNA, or hybrids of DNA and RNA, and can be single-stranded or double-stranded, naturally occurring or non-naturally occurring (e.g., phosphorothioate, peptide-nucleic acids, etc.). The insertional mutagens can be of any geometry, including but not limited to linear, circular, coiled, supercoiled, branched, hairpin, and the like, and can be any length capable of facilitating mutation, and tagging of an endogenous gene. Typically, the insertional mutagens are at least 5 nucleotides in length, at least 10 nucleotides in length, at least 15 nucleotides in length, at least 20 nucleotides in length, at least 25 nucleotides in length, at least 50 nucleotides in length, at least 100 nucleotides in length, at least 200 nucleotides in length, at least 250 nucleotides in length, at least 500 nucleotides in length, at least 1000 nucleotides (e.g., at least 1 kb) in length, etc. In some embodiments of the invention, the insertional mutagens can be at least 1 kb in length, at least 2 kb in length, at least 2.5 kb in length, at least 5 kb in length, at least 7.5 kb in length, at least 10 kb in length, or larger. Preferably, the insertional mutagens at least 10-15 nucleotides in length. This length allows the artisan to use nucleotide primers complementary to the inserted polynucleotide to be used to make primer extension products of the insertionally mutated gene to detect or characterize (e.g., sequence) the gene.

In certain embodiments of the invention, the insertional mutagens can comprise one or more nucleotide sequences that provide a desired function. Such nucleotides sequences include, but are not limited to, one or more multiple cloning sites, one or more transcription termination sites, one or more transcriptional regulatory sequences (e.g., one or more promoters, enhancers, or repressors), one or more sequences that encode translational signals, one or more open reading frames (ORFs), one or more sequences mutating ORFs, one or more stop codons, one or more sequences mutating or eliminating stop codons, one or more mRNA destabilizing elements, one or more RNA stabilizing elements, one or more sequences that result in the formation of hairpin loops, one or more sequences that disrupt or eliminate hairpin loops, one or more reporter genes, one or more splice acceptor sequences, one or more splice donor sequences, one or more internal ribosome entry sites (IRES), one or more transposon sequences, one or more site-specific recombination site sequences, one or more restriction enzyme sequences, one or more nucleotide sequences encoding a fusion partner protein or peptide (e.g., glutathione-S-transferase (GST), hexahistidine ($His_6$) or thioredoxin), one or more selectable markers or selection modules, one or more bacterial sequences useful for propagating the insertional mutagenic polynucleotide molecules in a host cell, one or more 3' gene trap cassettes, one or more nucleotide sequences encoding localization signals such as nuclear localization signals or secretion signals, one or more nucleotide sequences encoding one or more transmembrane regions (e.g., one or more amino acids, and typically one or more hydrophobic amino acids, capable of anchoring a polypeptide into a cellular membrane), one or more origins of replication, one or more protease cleavage sites, one or more desired proteins or peptides encoded by a gene or a portion of a gene, a 5' gene traps on an insertional mutagen, a 3' gene trap on an insertional mutagen, one or more selectable markers, one or more sequences encoding one or more 5' or 3' polynucleotide tails (particularly a poly (A) tail), and the like. As the ordinarily skilled artisan will readily understand, the insertional mutagens of the invention can comprise one or more of these or other nucleotide sequences, in any order and combination, and can comprise more than one of a given nucleotide sequence.

Preferably, the insertional mutagens comprises a selectable marker, a 5' gene trap, a splice acceptor with no operatively linked promoter, stop codons in all three reading frames, an IRES, a transposon sequence, or a site specific recombination site.

In one specific embodiment, the insertional mutagen comprises a splice acceptor sequence that does not contain an operably-linked promoter 5' to the splice acceptor. This polynucleotide can serve as an essential 5' gene trap. In certain other specific embodiments, the insertional mutagen is found on a retroviral vector. The retrovirus can be infectious or non-infectious but in a preferred embodiment the retrovirus vector can form infectious retrovirus particles. In another specific embodiment, the insertional mutagen contains sequences required for transposition and accordingly forms a transposable element. In a further specific embodiment, the insertional mutagen comprises a polynucleotide having a splice acceptor with no operably-linked promoter, the splice acceptor having an optimal branch point, the mutagen also containing three stop codons in all three reading frames, an IRES that includes an exonic splicing enhancer, the mutagen further comprising a selectable marker with a polyadenylation site operably-linked, and a polyA trap component. The polyA trap component can optionally be constructed as described herein and as generally known in the art. PolyA traps are also discussed in U.S. Pat. No. 6,410,266, incorporated herein by reference for disclosing polyA traps. In another embodiment, the insertional mutagen contains a splice acceptor without an operably-linked promoter 5', the splice acceptor containing an optimal branch point, the vector further containing three stop codons in all three reading frames, an IRES that does not contain the enhancer, a selectable marker with an operably-linked polyadenylation site, and wherein the vector does not contain the polyA trap.

In certain embodiments, the insertional mutagens comprise one or more nucleotide sequences capable of mutating an open reading frame (ORF). For example, the insertional mutagen can contain a number of nucleotides that is not divisible by 3, and which, therefore, would result in a frameshift upon insertion of the polynucleotide into an ORF.

In another embodiment, the insertional mutagen comprises one or more primer recognition sites, thereby facilitating the detection of the mutated gene using primer-based amplification or sequencing methods such as PCR.

In certain other embodiments of the invention, the insertional mutagens can additionally or alternatively comprise one or more stop codons. Stop codons are useful for terminating translation of genes, thereby facilitating mutation of a functional protein. The stop codons can be located on one or both strands of a double stranded insertional mutagen and can be nested to terminate translation in all three reading frames.

In certain other embodiments of the invention, the insertional mutagens can additionally or alternatively comprise one or more mRNA destabilizing elements. Upon integration into a gene and incorporation into an mRNA produced by the gene, the RNA instability element will decrease the amount of mRNA from the gene. A number of mRNA instability elements are known in the art and useful in the present invention (see, for example, Shaw et al., *Cell* 46:659-667 (1986); Ishida et al., *Nucleic Acids Research* 27:e35 (1999) each incorporated herein by reference for teaching RNA instability elements and methods of using such elements).

In certain other embodiments of the invention, the insertional mutagens can additionally or alternatively comprise one or more selectable markers. A selectable marker is a gene that encodes an expression product that can be selected for or against. Examples of selectable markers include but are not limited to: (1) polynucleotide segments that encode products which provide resistance against otherwise toxic compounds (e.g., antibiotics or other drugs); (2) polynucleotide segments that encode products which are otherwise lacking in the recipient cell (e.g., tRNA genes, auxotrophic markers); (3) polynucleotide segments that encode products which suppress the activity of a gene product; (4) polynucleotide segments that encode products which can be readily identified (e.g., phenotypic markers such as β-galactosidase, green fluorescent protein (GFP), and cell surface proteins); (5)

polynucleotide segments that bind products that are otherwise detrimental to cell survival and/or function; (6) polynucleotide segments that otherwise inhibit the activity of any of the polynucleotide segments described in (1)-(5) above (e.g., antisense oligonucleotides); (7) polynucleotide segments that bind products that modify a substrate (e.g., methylases and restriction endonucleases); (8) polynucleotide segments that can be used to isolate or identify a desired molecule (e.g. specific protein binding sites); (9) polynucleotide segments that encode one or more screenable markers; (10) polynucleotide segments, which when absent, directly or indirectly confer resistance or sensitivity of the cell to particular compounds; (11) polynucleotide segments that encode products which are toxic in recipient cells; (12) polynicleotide segments that inhibit replication, partition or heritability of nucleic acid molecules that contain them; and (13) polynucleotide segments that encode conditional replication functions, e.g., replication in certain hosts or host cell strains or under certain environmental conditions (e.g., temperature, nutritional conditions, etc.). In the present invention, selectable markers allow the detection of integration of the insertional mutagens into the host cell genome. In addition, selectable markers can be positioned on the insertional mutagens to allow selection for insertion events that occur in transcriptionally active or silent regions of the genome (see FIGS. 2-6 for non-limiting examples). The selectable marker can be expressed from a promoter on the insertional mutagen that is inserted or from a promoter located in the polynucleotide to be mutated (see FIG. 7 for non-limiting examples). Selectable markers suitable for use in accordance with this aspect of the invention include positive selectable markers and negative selectable markers.

A positive selectable marker allows cells expressing the selectable marker to survive selection, whereas cells not expressing the selectable marker die during selection. Examples of positive selectable markers include, but are not limited to, neomycin resistance gene (neo), puromycin resistance gene (puro), zeomycin resistance gene (zeo), hygromycin resistance gene (hyg), histidine D (his D), dihydroorotase, glutamine synthetase (gs), aspartate transcarbamylase, xanthine guanine phosphoribosyl transferase (gpt), carbamyl phosphate synthase (cad), multidrug resistance 1 (mdr1), thymidine kinase (tk), and hypoxanthine phosphoribosyl transferase (HPRT). Other suitable positive selectable markers are known in the art and will be familiar to the ordinarily skilled artisan. In accordance with the invention, the selectable marker can be expressed from a promoter on the insertional mutagen that is inserted, or from a promoter located in the DNA to be mutated. Accordingly, in the present invention, a positive selectable marker can be used, for example, to select for cells that have integrated the insertional mutagen (regardless of location in the genome) (FIG. 7, selection for SM) or for cells in which the insertion is into a transcriptionally active gene (for examples, see FIGS. 2-6).

A negative selectable marker causes cells expressing the selectable marker to die during selection, whereas those cells not expressing the selectable marker survive selection. Examples of negative selectable markers include but are not limited to HPRT, thymidine kinase, cholera toxin, pertussis toxin, tetanus toxin, and diphtheria toxin. Other negative selectable markers are known in the art and will be familiar to the ordinarily skilled artisan. The negative selectable marker used in accordance with the invention can be advantageously expressed from a promoter on the insertional mutagen, or from a promoter located in the DNA to be mutated. In the present invention, a negative selectable marker can be used, for example, to select against cells where insertion is into a transcriptionally active gene. The presence of a negative selectable marker in combination with site-specific recombination signals can also be used to select against cells that have failed to delete the sequences between the recombination signals (see, e.g., FIGS. 8C, 9A-9D and 9F for non-limiting examples of insertional mutagens useful in accordance with this embodiment of the invention).

In certain such embodiments, the insertional mutagen can contain one or more positive selectable markers and one or more negative selectable markers. In such embodiments in which the insertional mutagen contains both a positive and a negative selectable marker, the markers can be present as separate open reading frames or as a single fusion open reading frame (see FIG. 9F for a non-limiting example of such a polynucleotide). When the selectable markers are present in the polynucleotides as separate open reading frames, the positive selectable marker and negative selectable marker can be expressed as a single polycistronic transcript (see FIG. 9G for a non-limiting example of such a insertional mutagen) or as separate transcripts (see FIGS. 8C and 9A-9C for non-limiting examples of such insertional mutagens). The presence of both a positive selectable marker and a negative selectable marker in the same insertional mutagen can be used, for example, to select against actively expressed genes and for developmentally regulated genes, and vice versa. Alternatively, the presence of both a positive selectable marker and a negative selectable marker can be used to select for actively expressed genes that are down-regulated in response to developmental or environmental cues. Vectors and methods for trapping and selecting for developmentally regulated genes are well-known in the art (see, e.g., Gogos et al., *J. Virol.* 71:1644-1650 (1997); Wempe et al., *Genome Biol.* 2:research 23.1-23.10 (2001); and Medico et al., *Nature Biotech.* 19:579-582 (2001); the disclosures of all of which are incorporated herein by reference in their entireties for these vectors and methods).

In certain other embodiments of the invention, the insertional mutagens can additionally or alternatively comprise one or more recombination sites, for example one or more site-specific recombination sites or signals (see FIGS. 8 and 9). These recombination sites are discrete segments on the nucleic acid molecules that are recognized and bound by certain recombination proteins during the initial stages of integration or recombination between two nucleic acid molecules that each comprise such a recombination site. As discussed in detail above, such site-specific recombination sites or signals are useful for deleting (or inverting) the inserted insertional mutagen or a portion thereof from the DNA into which the insertional mutagen as inserted. This is useful, for example, for reverting the cellular phenotype(s) caused by the inserted insertional mutagen, which can be useful for confirming that a particular change in cellular phenotype is caused by a mutation induced by the insertion of the insertional mutagen. This approach is also useful for removing certain sequences from the inserted insertional mutagens, such as selectable markers, while leaving other sequences in the insertional mutagen, such as sequences that disrupt one or more genes in the DNA in which the insertional mutagen has inserted. Any site-specific recombination system can be used that is capable of deleting or inverting an inserted insertional mutagen. Examples of useful recombination signals include loxP, FRT, and att which are useful in conjunction with Cre, FLP (or FLPe) and PhiC31 recombinases, respectively (see, e.g., Hoess and Abremski, in: *Nucleic Acids and Molecular Biology*, vol. 4. Eds.: Eckstein and Lilley, Berlin-Heidelberg: Springer-Verlag; pp. 90-109 (1990); Broach, et al., *Cell* 29:227-234 (1982); Ishida et al., *Nucl. Acids Res.* 27:e35

(1999); O'Gorman et al., *Science* 251:1351-1355 (1991); Bergemann et al., *Nucl. Acids Res.* 23:4451-4456 (1995); Sauer, B., *Curr. Opin. Biotech.* 5:521-527 (1994); Schwenk et al., Nucleic Acids Res. 2002 Jun. 1;30(11):2299-306; Schaft et al.; Genesis. 2001 September;31(1):6-10; Farley et al.; Genesis, 2000 November-December;28(3-4):106-10; Rodriguez et al.; Nat Genet. 2000 June;25(2):139-40; Buchholz et al.; Nat Biotechnol. 1998 July;16(7):657-62; Olivares et al.; Gene. 2001 Oct. 31;278(1-2:167-76; Lee L, Sadowski P D, J Biol Chem. 2001 Aug. 17;276(33):31092-8; Kolb A F, Anal Biochem. 2001 Mar. 15;290(2):260-71; Araki et al., Nucleic Acids Res. Feb. 1997 15;25(4):868-72; Albert et al., Plant J. 1995 April;7(4):649-59; Santoro et al., Proc Natl Acad Sci USA Apr. 2, 2002; 99(7):4185-90; Trinh et al., J Immunol Methods, 2000 Oct. 20;244(1-2):185-93; Soukharev et al., Nucleic Acids Res. 1997 Sep. 15;27(18):e21 and U.S. Pat. Nos. 4,959,317, 5,434,066, 5,888,732, 6,080,576 and 6,136,566; each incorporated herein by reference for teaching vectors and methods of site specific recombination in mammalian cells). Other examples of suitable recombination sites for use in the insertional mutagens of the present invention include the attB, attP, attL, and attR sequences which are recognized by the recombination protein β Int, and by the auxiliary proteins integration host factor (IHF), FIS and excisionase (Xis). See Landy, *Curr. Opin. Biotech.* 3:699-707 (1993); see also U.S. Pat. Nos. 5,888,732, 6,143,557, 6,171,969 and 6,277,608, each of which is incorporated by reference herein in its entirety. Additional examples of recombination systems include Hin, Gin, Pin, Cin, and VDJ recombination, all of which are well-known in the art and which will be familiar to the ordinarily skilled artisan. Other site-specific recombination systems known in the art would also be recognized as useful by the ordinarily skilled artisan, and therefore can be used in accordance with the methods and compositions of the present invention. The site specific recombination signals may be wildtype or mutant. Mutant signals can be used, for example, to control the reversibility of the recombination reaction (reference Araki et al., Nucleic Acids Res. 1997 Feb. 15;25(4):868-72; Dale et al., Plant J. 1995 April;7(4):649-59; Trinh et al., J Immunol Methods, 2000 Oct. 20;244(1-2):185-93; Soukharev et al. Nucleic Acids Res. 1999 Sep. 15;27(18):e21 incorporated in its entirety). The site-specific recombinases used in accordance with this aspect of the invention may be wildtype, mutant, or fusion proteins. Examples of modified recombinases useful in this aspect of the invention include, but are not limited to, cell-permeable CRE and CRE-ER (Jo et al., *Nature Biotech.* 19:929-933 (2001); Vallier et al., *Proc. Natl. Acad. Sci. USA* 98:2467-2472 (2001); each of which is incorporated by reference herein in its entirety). The recombinases used in the invention can be delivered to cells by infection or transfection of an expression vector encoding the recombinase (Westerman et al., *Proc. Natl. Acad. Sci. USA* 93:8971-8976 (1996), which is incorporated by reference herein in its entirety), transfection of the protein (e.g., via electroporation; Ager et al., *Radiat. Res.* 128:150-156 (1991); Chung et al., *Radiat. Res.* 125:107-113 (1991); each of which is incorporated by reference herein in its entirety), or through the use of a cell-permeable recombinase (Jo et al., *Nature Biotech.* 19:929-933 (2001); Vallier et al., *Proc. Natl. Acad. Sci. USA* 98:2467-2472 (2001); each of which is incorporated by reference herein in its entirety). Alternatively, the recombinase gene may itself be present on the insertional mutagen. The site-specific recombinase gene and/or recombination site from any of these systems can be included on the insertional mutagens of the invention, or can be introduced into the host cell separately to achieve the desired recombination event.

Using insertional mutagens containing one or more recombination sites, mutated cells or organisms (e.g., cells or organisms containing one or more mutated genes) produced by the methods of the invention can optionally be analyzed to confirm that any change in phenotype observed in the mutated cell or organism is the result of at least one insertionally mutated gene. One such method involves the use of site-specific recombination to reverse the phenotypic change, typically by inducing a reversion of the mutation to the wild-type by deleting or inverting the inserted insertional mutagen. In one such embodiment, site-specific recombination signals recognized by specific recombinase enzymes (e.g., the att/Int system from bacteriophage □, the lox/Cre system from bacteriophage P1, and the frt/FLP system from the Saccharomyces cerevisiae 2µ circle plasmid) can be included on the insertional mutagen (see FIGS. 9A-9H for non-limiting examples of such insertional mutagens containing site-specific recombination signals). Generally, such recombination sites are positioned on the insertional mutagen to allow the entire insertional mutagen, or a portion of the insertional mutagen responsible for mutating the gene, to be removed from or inverted within the DNA into which the insertional mutagen has inserted by introducing the appropriate recombinase enzyme into the cell. Optionally, as discussed below, use of a negative selectable marker or a reporter gene can facilitate identification or isolation of cells in which the mutagenic portion of the insertional mutagen has been deleted or inverted, and any change in cellular phenotype as a result of such deletion or inversion can be assessed so as to determine the phenotypic effects of the insertional mutagenesis (e.g., reversal or alteration of the cellular phenotype that is obtained upon insertional mutagenesis indicates that at least one insertional mutation is likely responsible for the observed change in phenotype from the wildtype).

The invention can also be used to identify developmentally regulated genes. In one embodiment, the presence of both a positive selectable marker and a negative selectable marker in the same insertional mutagen can be used, for example, to select against actively expressed genes and for developmentally regulated genes. Alternatively, the presence of both a positive selectable marker and a negative selectable marker can be used to select for actively expressed genes that are down-regulated in response to developmental or environmental cues. Vectors and methods for trapping and selecting for developmentally regulated genes are well-known in the art (see, e.g., Gogos et al., *J. Virol.* 71:1644-1650 (1997); Wempe et al., *Genome Biol.* 2:research 23.1-23.10 (2001); and Medico et al., *Nature Biotech.* 19:579-582 (2001); the disclosures of all of which are incorporated herein by reference in their entireties for these vectors and methods). Other methods for identifying trapped developmentally regulated genes in accordance with the invention involve the use of insertional mutagens that function as gene trap vectors such as those depicted in FIGS. 9B, 9C and 9H. These will comprise, for example, at least two site-specific recombination signals (e.g., at least two lox sites (e.g., loxP), at least two att sites (e.g., attP, attB, attL and/or attR), at least two FRT sites, or the like), which flank the positive selectable marker (as in FIG. 9B), the negative selectable marker (as in FIG. 9C), or both the positive and negative selectable markers (as in FIGS. 9G and 9H).

In a first such embodiment, the insertional mutagens depicted in FIGS. 9B, 9H, 11, and 13, can be integrated using standard methods of introduction of nucleic acid molecules into host cells that are well-known in the art and that therefore will be familiar to the ordinarily skilled artisan. Once the insertional mutagen has been integrated, cells can be selected based on the positive selectable marker carried by the insertional mutagen (and therefore integrated into DNA in the host cell). Surviving clones will contain the insertional mutagen integrated into a transcriptionally active gene, since it is only in such cells that the positive selectable marker will also be expressed. Cells can then be treated to delete the positive selectable marker (FIG. 11) or invert the positive marker (FIG. 13 legend) and create an operable linkage between the trapped gene and the negative selectable marker. In certain such aspects of the invention, this result is obtained through a site-specific recombination reaction: cells are treated with a site-specific recombinase, the identity of which will depend upon the specific recombination site used in construction of the insertional mutagen (e.g., Cre recombinase is used with lox recombination sites; Int recombinase is used with att recombination sites; FLP recombinase is used with frt recombination sites; etc.). Such treatment results in recombination between opposing recombination sites (see, e.g., FIG. 9B), thereby deleting or inverting the positive selectable marker from (and operably linking the negative selectable marker and the trapped gene) the genome of the cell. Cells can then be cultured under new conditions and/or treated with selection agents, and cells can be selected for lack of expression of the negative selectable marker to identify cells in which transcription of the trapped gene has been reduced or eliminated (e.g., cells that survive the negative selection). This process is illustrated schematically in FIG. 11 and described in FIG. 13 legend.

In another such embodiment, the insertional mutagens depicted in FIGS. 9C and 9H can be integrated using standard methods of introduction of nucleic acid molecules into host cells that are well-known in the art and that therefore will be familiar to the ordinarily skilled artisan. Once the insertional mutagens have been integrated, cells can be selected based on the negative selectable marker carried by the insertional mutagen (and therefore integrated). Cells in which the insertional mutagen has integrated into (e.g., that have trapped) a transcriptionally active gene will die during selection since it is only in such cells that the negative selectable marker will also be expressed, whereas cells in which the insertional mutagen has integrated into a transcriptionally silent region of the genome will survive. Cells can then be treated to delete the negative selectable marker and create an operable linkage between the trapped gene and the positive selectable marker, for example using site-specific recombination as outlined above. Such treatment results in recombination between opposing recombination sites (see, e.g., FIG. 9C), thereby deleting (FIG. 12) or inverting (FIG. 13) the negative selectable marker such that the positive selectable marker becomes operably linked to the trapped gene. Cells can then be cultured under new conditions or treated with agents capable of inducing gene expression, and cells can be selected for expression of the positive selectable marker to identify cells in which transcription of the trapped gene is increased (e.g., cells that survive the positive selection). This process is illustrated schematically in FIGS. 12 and 13.

In certain other embodiments of the invention, the insertional mutagens can additionally or alternatively comprise one or more reporter genes, also known as screenable markers. A reporter gene is a gene that encodes an expression product that can be detected in the cell. In accordance with the invention, the reporter gene may be expressed from a promoter on the insertional mutagen, or from a promoter in the DNA into which the insertional mutagen is inserted. Detection of the reporter gene allows the artisan to screen for cells that are or are not expressing the reporter gene. In the present invention, reporter genes allow insertions to be detected. In addition, reporter genes can be positioned on the insertional mutagen to allow screening for insertion events that occur in transcriptionally active or silent regions of the genome (see FIGS. 2-6). Reporter genes suitable for use in accordance with the invention can be any gene that encodes an expression product for which an assay exists. Examples of such suitable reporter genes include, but are not limited to, enzymes, structural proteins, cell surface proteins, and fluorescent proteins. Specific reporter genes known in the art include β-lactamase, β-galactosidase, luciferase, chloramphenicol acetyl transferase, green fluorescent protein and its derivatives, yellow fluorescent protein and its derivatives, blue fluorescent protein and its derivatives, cyan fluorescent protein and its derivatives, and red fluorescent protein and its derivatives. Many other reporter genes are known in the art and would be recognized by the artisan as being useful in the present invention.

Assays for detecting reporter genes include, but are not limited to, enzyme activity assays, cell microfluorimetry or fluorescence-activated cell sorting (FACS®), magnetic bead cell sorting, ELISA, ELISA Spot, transcriptional reporter assays, and cellular phenotypic assays such as proliferation, transformation, morphology, and the like.

Reporter genes can be used optionally in place of or in addition to the site specific recombination sequences to identify developmentally regulated genes and to revert phenotypes.

In certain other embodiments of the invention, the insertional mutagens can additionally or alternatively comprise one or more selectable markers and one or more reporter genes. The one or more selectable markers and one or more reporter genes can be present as a fusion gene or as two discrete open reading frames. Any combination of selectable markers and reporter genes can be used, including those detailed above. An example of a useful selectable reporter gene fusion is β-geo, a fusion of the neomycin resistance gene and the β-galactosidase gene. Other fusion genes known in the art, and which therefore are familiar to the ordinarily skilled artisan, can also be used in the present invention.

In certain other embodiments of the invention, the insertional mutagens can additionally or alternatively comprise one or more splice acceptor sequences. Upon introduction into the target DNA, the one or more splice acceptor sequences can become paired with one or more splice donor sequences in the target DNA, thereby directing splicing from the gene in the DNA to the inserted insertional mutagen. This splicing, in turn, facilitates mutation of a gene in the target DNA through the creation of a fusion mRNA molecule. Any sequence capable of functioning as a splice acceptor site can be used in accordance with this aspect of the present invention. The splice acceptor site can be naturally occurring or non-naturally occurring. Splice acceptor sites and methods for testing the splicing activity of candidate or putative splice acceptors are known in the art, and therefore will be familiar to the ordinarily skilled artisan. In human cells, splice acceptor sites have a characteristic sequence represented as: YYYYYYYYYYNYAG (SEQ ID NO:1), wherein Y denotes any pyrimidine and N denotes any nucleotide (see *Nucleic Acids Research* 19:3715-3799 (1991)).

In other embodiments of the invention, the insertional mutagens can additionally or alternatively comprise one or more splice donor sequences. Upon introduction into the target DNA, the one or more splice donor sequences can become paired with one or more splice acceptor sequences in the target DNA, thereby directing splicing from the polynucleotide to a gene in the target DNA. This splicing, in turn facilitates mutation of the gene through the creation of a fusion mRNA molecule. The splice donor site may optionally be paired with a splice acceptor site on the insertional mutagen. Typically, in such a configuration, the order of these elements will be the splice acceptor followed by the splice donor (see FIGS. 1H-1J, 2D and 2H for non-limiting examples). The splice donor site may optionally be operably linked to a promoter on the insertional mutagen to produce a promoter-splice donor 3' gene trap (see FIGS. 5B-5E for non-limiting examples of such vectors). Any sequence capable of functioning as a splice donor site can be used. The splice donor site can be naturally occurring or non-naturally occurring. Splice donor sites and methods for testing splicing activity of candidate or putative splice donor sites are known in the art, and therefore will be familiar to the ordinarily skilled artisan. In human cells, splice acceptor sites have a characteristic sequence represented as: (A/C)AG GURAGU (SEQ ID NO:2), wherein R denotes a purine nucleotide (see *Nucleic Acids Research* 19:3715-3798 (1991)). The insertional mutagen may contain one or more exon sequences. These can be naturally occurring or non-naturally made, as by recombinant DNA or synthetic methods. The exons may be derived from eukaryotic genes. Further, the one or more exons can be in tandem.

In other embodiments, the insertional mutagens can additionally or alternatively comprise one or more sequences that direct the addition of 5' or 3' polynucleotide tails on mRNA molecules transcribed from the DNA into which the insertional mutagen integrates. Such sequence can encode any polynucleotide tail, such as poly (A) tails, poly (G) tails, poly (U) tails, poly (C) tails, poly (I) tails, and the like. In one embodiment, the insertional mutagen comprises one or more polyadenylation signals that direct the addition of poly (A) tails on mRNA molecules transcribed from the DNA into which the insertional mutagen integrates. Polyadenylation signals can be derived from naturally occurring or non-naturally occurring sequences. Examples of useful polyadenylation signals include, but are not limited to, those derived from SV40 genes, growth hormone genes (e.g., bovine growth hormone), β-globin genes, actin genes, serum albumin genes, and retrovirus genes. Other polyadenylation signals are known in the art and will therefore be familiar to the ordinarily skilled artisan.

In certain other embodiments of the invention, the insertional mutagens can additionally or alternatively comprise one or more internal ribosomal entry sites (IRES). The IRES allows translation of internal open reading frames and are useful for expressing open reading frames located on the insertional mutagens upon integration into transcriptionally active genes. In certain embodiments, the ORF on the insertional mutagen is a selectable marker and/or reporter gene. Any IRES can be used to express an ORF located on the insertional mutagen. Examples of useful IRESs and methods of measuring IRES activity are known in the art (see, for example, Zhou et al., *PNAS* 98:1531-1536 (2001), Owens et al., *PNAS* 99:1471-1476 (2001); Venkatesan et al., *Mol Cell Biol.* 8: 2826-2837 (2001); Jackson et al., *Trends Biochem. Sci.* 15: 477-483 (1990); and Jang et al., *J. Viroi.* 62:2636-2643 (1988); each incorporated herein by reference for teaching IRES sequences and methods for measuring IRES activity).

In certain other embodiments of the invention, the insertional mutagens can additionally or alternatively comprise one or more transposon signals. 1. Cui et al., J Mol Biol. 2002 May 17;318(5):1221-35; 2. Izsvak et al., J Biol Chem. 2002 Jun. 24;3. Dupuy et al., Proc Natl Acad Sci USA. 2002 Apr. 2;99(7):4495-9; 4. Horie et al., Proc Natl Acad Sci USA. 2001 Jul. 31;98(16):9191-6; 5. Dupuy et al., Genesis. 2001 June; 30(2):82-8; 6. Fischer et al., Proc Natl Acad Sci USA. 2001 Jun. 5;98(12):6759-64; 7. Ivics et al., Cell. 1997 Nov. 14;91 (4):501-10. Other transposons also function in mammals: 8. Zagoraiou et al., Proc Natl Acad Sci USA. 2001 Sep. 25;98 (20):11474-8; 9. Sherman et al., Nat Biotechnol. 1998 November;16(11):1050-3; 10. Kawakami et al., Proc Natl Acad Sci USA. 2000 Oct. 10;97(21):11403-8; 11. Fadool et al., Proc Natl Acad Sci USA. 1998 Apr. 28;95(9):5182-6; 12. Plasterk R H, Cell. 1993 Sep. 10;74(5):781-6; 13: Kaufman et al., Nucleic Acids Res. 1991 Nov. 25;19(22):6336; 14. Rubin et al., Nucleic Acids Res. 1983 Sep. 24;11(18):6341-51; 15. Spradling et al., Science. 1982 Oct. 22;218(4570):341-7; Ac and Ds and other plant transposons transpose, integrate and are used as insertional mutagens in plants: 16. Grevelding et al, Proc Natl Acad Sci USA. 1992 Jul. 1;89(13):6085-9; 17. Walbot V., Curr Opin Plant Biol. 2000 April;3(2):103-7; 18. Pereira et al, Methods Mol Biol. 1998; 82:329-38; 19. Cooley et al., Mol Gen Genet. 1996 Aug. 27;252(1-2):184-94; 20. Bhatt et al, Plant J. 1996 June;9(6):935-45. P element transposon can integrate broadly throughout genomes: 21. Kassis et al., Proc Natl Acad Sci USA. 1992 Mar. 1;89(5):1919-23; 22. Berg et al., Genetics. 1991 March;127(3):515-24; 23. Tower et al., Genetics. 1993 February;133(2):347-59; 24. Cooley et al., Prog Nucleic Acid Res Mol Biol. 1989; 36:99-109; 25. Cooley et al., Science. 1998 Mar. 4;239(4844):1121-8; 26. Spradling et al., Proc Natl Acad Sci USA. 1995 Nov. 21;92(24):10824-30.

Transposon signals allow the insertional mutagens to insert into the DNA by expressing or otherwise introducing transposase in the cell with the insertional mutagen. In a preferred embodiment, the insertional mutagen is first introduced into DNA in a cell, and subsequently transposed, or "hopped," in order to insertionally mutate one or more genes. This can be done in vitro, in vivo, and in situ. Methods for transposing vectors in situ are well known in the art (see, for example, Lucklow et al., *J. Virol.* 67:4566-4579 (1993); Ivics et al., *Cell* 91:501-510 (1997); and Luo et al., *PNAS* 95:10769-10773 (1998); each incorporated herein by reference for teaching vectors and methods of transposition thereof).

There are many transposon systems and transposon signals known in the art that are useful in the present invention. These include TY from yeast (e.g., TY1; see Devine and Boeke *Nucl. Acids Res.* 22:3765-3772 (1994), which is incorporated by reference herein in its entirety), P-elements, Hobo, Minos, and Manner from Drosophila, Tn5, Tn7, T0, Tn10, and Mu from bacteria, En/Spm from maize, and TCl/Mariner (and its derivatives, such as Sleeping Beauty) and Minos from mouse and *C. elegans*. Many other transposon systems are known in the art and would be recognized by the artisan as useful in the present invention. In addition, modified transposon signals and mutant transposases with enhanced efficiency have been described and would be useful in the present invention.

Any of the insertional mutagens described herein for insertion can be produced as viral vectors, such as retroviral vectors (including lentivirus), Herpesviruses vectors (such as Epstein-Barr virus, cytomegalovirus (CMV), Herpes zoster, and Herpes simplex), papillomavirus, picomavirus, papovavirus (such as polyoma vectors and SV40), adenovirus, adeno-associated virus, and hepatitis virus. Particularly preferred vectors are retroviral. Viruses have the advantage of efficiently introducing the insertional mutagens into a cell, and, in the case of some viruses, facilitating efficient delivery of the insertional mutagen to the cell, and integration of the insertional mutagen into DNA in a cell.

Retroviral vectors of the invention and of use in the methods of the invention can contain retroviral LTRs, packaging signals, and any other sequences that facilitate creation of infectious retroviral vectors. Retroviral LTRs and packaging signals allow the insertional mutagens of the invention to be packaged into infectious particles and delivered to the cell by viral infection. Methods for making recombinant retroviral vectors are well known in the art (see for example, Brenner et al., PNAS 86:5517-5512 (1989); Xiong et al., Developmental Dynamics 212:181-197 (1998) and references therein; each incorporated herein by reference). In preferred embodiments, the retroviral vectors used in the invention are reverse orientation vectors, meaning that the gene mutation element in the insertional mutagen is in the opposite direction of viral transcription. The retroviral vectors can also be Self Inactivating viruses (SIN viruses). SIN viruses are not transcriptionally active upon insertion. Methods for making SIN viruses are known in the art (see for example, Hawley et al., PNAS 84:2406-2410 (1987); Brenner et al, PNAS 86:5517-5512 (1989); and Lih et al., Gene 164:289-294 (1995); each incorporated herein by reference for teaching vectors). Retroviral LTRs and packaging signals can be selected according to the intended host cell to be infected. Examples of retroviral sequences useful in the present invention include those derived from Murine Moloney Leukemia Virus (MMLV), Avian Leukemia Virus (ALV), Avian Sarcoma Leukosis Virus (ASLV), Feline Leukemia Virus (FLV), and Human Immunodeficiency Virus (HIV). Other viruses known in the art are also useful in the present invention and therefore will be familiar to the ordinarily skilled artisan.

In certain other embodiments, the insertional mutagens can additionally or alternatively comprise one or more bacterial sequences useful for propagating the insertional mutagens in prokaryotic or eukaryotic cells. Thus, the insertional mutagens of the invention can contain, for example, one or more antibiotic resistance markers, and/or one or more other art known sequences useful for propagating and analyzing the insertional mutagens.

Any of the insertional mutagens described herein can further or alternatively comprise one or more 3' gene trap. A number of 3' gene traps have been described and are useful in the present invention (see e.g., Harrington et al., WO 99/15650; Zambrowicz et al., U.S. Pat. No. 6,080,576; Sands et al., U.S. Pat. No. 6,136,566; Niwa et al., J. Biochem. 113: 343-349 (1993); Yoshida et al., Transgenic Research 4:277-287 (1995); all incorporated herein by reference in its entirety for teaching 3' gene traps). The 3' gene trap can be used to recover exons in the target DNA that are downstream of the insertional mutagen insertion site. Optionally, it can also be used to activate RNA or protein expression from genes in the target DNA. When a 3' gene trap cassette is contained in a insertional mutagen of the present invention, it can be located upstream or downstream of a mutagenic portion of the insertional mutagen. In preferred embodiments, the 3' gene trap is located 3' of the mutagenic portion of the insertional mutagen.

Further, any of the insertional mutagens described herein can further or alternatively comprise one or more 5' gene trap cassettes. A number of 5' gene traps have been described and are useful in the present invention (see e.g., Zambrowicz et al., U.S. Pat. No. 6,080,576; Sands et al., U.S. Pat. No. 6,136, 566; Niwa et al., J. Biochem. 113:343-349 (1993); Yoshida et al., Transgenic Research 4:277-287 (1995); all incorporated herein by reference in its entirety for teaching 3' gene traps). The 5' gene trap can be used to recover exons in the target DNA that are downstream of the insertional mutagen insertion site. Optionally, it can also be used to activate RNA or protein expression from genes in the target DNA. When a 5' gene trap cassette is contained in a insertional mutagen of the present invention, it can be located upstream or downstream of a mutagenic portion of the insertional mutagen. In preferred embodiments, the 5' gene trap is located 5' of the mutagenic portion of the insertional mutagen.

Integration of the Insertional Mutagens

The insertional mutagens of the invention can be introduced into a cell and integrated into DNA by any method known in the art. In a preferred embodiment, they are introduced by transfection. Methods of transfection include, but are not limited to, electroporation, particle bombardment, calcium phosphate precipitation, lipid-mediated transfection (e.g., using cationic lipids), micro-injection, DEAE-mediated transfection, polybrene mediated transfection, naked DNA uptake, and receptor mediated endocytosis.

In another preferred embodiment, the insertional mutagens are introduced by viral transduction or infection. Suitable viral vectors useful in the present invention include, but are not limited to, adeno-associated virus, adenovirus vectors, alpha-herpesvirus vectors, pseudorabies virus vectors, herpes simplex virus vectors and retroviral vectors (including lentiviral vectors). Methods for making and using viral vectors are described above and elsewhere herein, and are well-known in the art and therefore familiar to the ordinarily skilled artisan (see, for example, Viral Vectors: Gene Therapy and Neuroscience Applications E. Caplitt and Loewy, Academic Press, San Diego (1995); incorporated herein by reference for teaching viral vectors and methods of using such vectors for introducing and expressing polynucleotides of interest).

In a preferred such embodiment, the vectors are retroviral vectors (including lentiviral vectors) and are introduced into the cell by infection. Vectors containing viral LTRs and packaging signals are described above. Methods for packaging retroviral vectors are also known in the art and can be used in the present invention (see, for example, U.S. Pat. No. 5,449, 614, the disclosure of which is incorporated herein by reference in its entirety for teaching vectors, packaging cell lines, and methods of making and packaging viral vectors).

Following induction of an endogenous insertional mutagen or its introduction into a cell by transfection or infection, the insertional mutagens of the invention integrate into the genome of the cell. The insertional mutagen can integrate into the target DNA by any method including, but not limited to, non-homologous recombination including retroviral insertion and transposition, site-specific recombination, homologous recombination and the like. In certain preferred embodiments, the insertional mutagen integrates by non-homologous recombination (e.g., integration by DNA end-joining, retroviral insertion, or transposition).

In certain preferred embodiments of the invention, the cell can be treated with one or more DNA-breaking agents prior to, during, or following induction or introduction of the insertional mutagen into the cell. DNA-breaking agents increase the efficiency of integration. Examples of DNA-breaking agents suitable for use in accordance with this aspect of the invention include, but are not limited to, γ-radiation, X-ray irradiation, UV irradiation, bleomycin, peroxides, and restriction enzymes. Other agents known to break DNA in living cells can also be used. Methods of using DNA breaking agents to enhance insertional mutagen insertion have been described (see, e.g., Harrington et al., WO 99/15650, incorporated herein by reference for teaching methods of enhancing nonhomologous recombination).

In one embodiment, the initial integration is not the mutagenic event. Where the insertional mutagen contains a transposition signal, after the initial integration, the methods of the invention can be carried out by inducing an endogenous insertional mutagen to transpose ("hop") to a new location, where the mutagenic event(s) can occur. Methods for transposing vectors in situ are well known in the art and therefore will be familiar to the ordinarily skilled artisan (see, for example, Ivics et al., Cell 91:501-510 (1997); and Luo et al., PNAS 95:10769-10773 (1998); each incorporated herein by reference for teaching transposition vectors and methods).

A variety of genes can be mutated using the methods of the invention. For example, known genes, including disease-causing genes (e.g., oncogenes, integrated viral genes (including HIV), genes causing genetic abnormalities such as cancers, multiple sclerosis, Alzheimer's disease, diabetes, muscular dystrophy, ALS, Gaucher's Disease, Tay-Sachs disease, hemophilia, β-thalassemia, cystic fibrosis, sickle cell trait, and the like) and normal genes (imparting any phenotype to a cell or organism) can also be mutated using the methods of the invention. In another embodiment, genes which have been previously unknown or incompletely characterized can be mutated using the methods of the invention. In another embodiment, genes can be mutated that are known or characterized but which were not known to be correlated to a desired phenotype produced by the mutagenesis methods of the invention. The invention thus provides a way to identify, isolate and characterize previously unknown or incompletely characterized genes in a variety of eukaryotic cells, and to examine the phenotypic importance of such genes by examining the effects on cellular phenotype when the genes are mutated.

It is also possible to have multiple (more than one per cell) insertional mutagens in each target cell to increase the probability that at least one gene will be mutated in the cell. Thus, cells created by the present methods can contain one or more integrated insertional mutagen. In certain embodiments, each of the target cells will contain 1-10 insertional mutagens, or 10 or more insertional mutagens. Two or more insertional mutagens in a single cell has the advantage of reducing the total number of cells that must be screened to identify a cell with a mutation of a desired gene or of a gene(s) that causes a desired phenotype.

The number of insertional mutations that would be useful depends on the size of the genome of the host cell, its ploidy, gene structure, the average insertion window associated with gene mutation (e.g., size of the gene), the amount of genome coverage that is desired (e.g., the percentage of genes that are to be insertionally mutated), the propensity for integration of the insertional mutagen into genes, and the number of genes capable of producing a desired phenotype when mutated. In higher eukaryotic organisms, the genome is typically large. In mouse and human cells, for example, the haploid genome is estimated to be $3 \times 10^9$ base pairs (6 billion basepairs for the diploid genome). Therefore, $10^6$ insertions will result in an insertional mutagenic event frequency of 1 insertion per 3,000 base pairs. Assuming that an average human gene is approximately 25,000 base pairs, and assuming random insertion, $10^6$ insertions at a frequency of 1 in 3,000 base pairs will, on average, result in the mutation of one copy of each gene at least once. In practice, it can be necessary to create a larger or smaller number of insertions if integration is found not to be random. For example, it can be necessary to produce $10^7$ or more random insertions to insertionally mutate the majority of genes at least once. It is also useful in certain situations or for certain applications to create fewer insertions. In preferred embodiments, an insertion library containing at least 10,000 insertions is created. In highly preferred embodiments, an insertion library containing at least 100,000 insertions is created. In the situation where the desire is to focus mutagenesis on those genes that can be transcriptionally active in the cell under study, then use of insertional mutagens that show a bias for insertion into active genes (e.g., retroviruses or transposons) can enable the creation of libraries of $10^4$-$10^5$ members that contain knockouts of all active genes.

Since genome sizes vary, it is possible to rely on general guidelines for determining the number of insertions necessary to create a library of a given complexity. As a general guideline it is useful to create 1 insertion per 1000 to 10,000 base pairs of the host cell genome. In one embodiment, 1 insertion is created per 30,000 base pairs of host cell genome. In highly preferred embodiments, the insertion frequency is adjusted to create at least one mutation per gene in the library. It should be understood that these are general guidelines and that other insertion frequencies are possible and recognized by those skilled in the art.

In embodiments where the insertional mutagen contains a selectable marker or reporter gene, cells can be selected for integration by selecting for expression of the selectable marker. If the selectable marker is expressed from a promoter on the insertional mutation (see, for example, FIG. 14), than any cell containing an integrated insertional mutagen should be recovered. If the selectable marker is not expressed from a promoter on the insertional mutagen, but is expressed from an upstream promoter on the target DNA (see FIGS. 2-6 for examples), then any cell containing the insertional mutagen integrated into a transcriptionally active gene can be selected for or against depending on whether a positive or negative selectable marker, respectively, is being used. Integration into transcriptionally active genes is desirable because in instances where the cells are going to be screened for a phenotype, mutation of a transcriptionally active gene is more likely to give a phenotype than mutation of a transcriptionally inactive gene. Alternatively, selection against a transcriptionally active gene can be useful for removing cells that have insertionally mutated a transcriptionally active gene so that other genes can be studied. For example, after removing cells containing mutated transcriptionally active genes, cells can be treated with agents that cause a change in gene expression within the cell and the artisan can now screen for phenotypes that result from mutation of genes that were previously silent but became active. Reporter genes can also optionally be used to screen for integration into transcriptionally active or silent genes.

Library Construction

The two mutagenesis methods can be carried out on one cell. The cell can then be screened for mutation of a specific desired gene or for a desired phenotype that results from mutation of one or more genes.

In one embodiment, insertional mutagenesis is carried out on a single physicochemically mutated clone of cells. For example, a single physicochemically mutated cell can be expanded and used for insertional mutagenesis. This creates a library of cells that are mutagenized by both methods. Typically, for mammalian cells, between 1 and $10^7$ or more gene trap insertions are created for each physicochemically mutated clone. A gene trap insertion is an instance where genomic integration of the insertional mutagen has become operably linked to a constitutively or conditionally active endogenous gene such that exonic sequences in the insertional mutagen are incorporated into the transcripts of the endogenous gene. Many of these gene trap insertions will disrupt the normal function of the insertionally mutagenized genes. In some embodiments this range would be to $10^2$ to $10^4$ insertions per mutated clone. In certain preferred embodiments, the number of insertion mutants created for each physicochemically mutated clone ranges between $10^4$ and $10^6$, and often between $10^4$ and $10^5$. In one embodiment, after the insertional mutagenesis, the resulting library can be screened for integration of one or more of the insertional mutagens. In another embodiment, the resulting library is screened for mutation of a specific gene of interest or for a phenotype that results from mutation of a gene of interest, or for a phenotype that results from mutation of a gene that has not been previously identified or not previously known to be correlated with the phenotype. The mutant cells produced by these methods of the invention also can be cloned. The mutant cells that exhibit the phenotype derived from the combined mutagenesis can be cloned, for example to generate a purified population for further manipulation or use.

In another embodiment, insertional mutagenesis is carried out on more than one physicochemically mutated clone of cells. For example, more than one physicochemically mutated cell can be expanded for insertional mutagenesis. The number of physicochemically mutated clones can range from 1 to $10^6$ or more. In preferred embodiments, the number of physicochemically mutated clones used to create the insertion mutants is between 1 and 100,000 and more preferably between 1 and 10,000. In highly preferred embodiments, the number of physicochemically mutated clones used to create the insertion mutants is between 1 and 1000. Useful ranges include approximately 2, 5, 10, 25, 50, 100, 200, 400, 600, and 800 clones. Guidelines for assessing physicochemical mutation frequency and selecting appropriate numbers of mutated cells are discussed above in the section describing physicochemical mutagenesis. The selected number of physicochemically mutated cells can be expanded and used to create a library of cells that are mutagenized by the two methods. Typically, for mammalian cells, between 1 and $10^8$ or more insertions are created for each physicochemically mutated clone present. In preferred embodiments, the number of insertion mutants created for each physicochemically mutated clone ranges between $10^4$ and $10^6$, and often between $10^4$ and $10^5$. For example, without limitation, if 100 physicochemically mutated clones are used to create a library, then a library with $10^4$ insertions per clone would result in the creation of a library with $10^6$ clones (100 physicochemically mutated clones×$10^4$ insertionally mutated clones). In one embodiment, the resulting library can be screened for integration of one or more insertional mutagens after the insertional mutagenesis. In another embodiment the resulting library can be screened for mutation of a gene of interest, for a phenotype that results from mutation of a gene of interest, or for a phenotype that results from a mutation of a gene not previously identified or not known to be correlated with the phenotype. The mutant cells produced by these methods of the invention also can be cloned.

It is also possible to make the library by insertional mutagenesis and then use that library for physicochemical mutagenesis. In one embodiment, one or more cells is mutated by integration of one or more insertional mutagens. Typically, in mammalian cells, the insertional mutagen is inserted into 1 to $10^7$ or more cells. In preferred embodiments, the insertional mutagen is inserted into between $10^4$ to $10^6$ cells, and often into between $10^4$ to $10^5$ cells. Cells containing the integrated insertional mutagens are then physicochemically mutated. With either procedure, in one embodiment, clones are expanded prior to physicochemical mutagenesis. Preferably, between 50 and 10,000 genes are mutated in each physicochemically mutated cell. In certain embodiments, approximately 1,000 genes are mutated in each target cell. Once created, the physicochemically/insertionally mutated library of cells can be screened for mutation of a gene of interest or for a phenotype that results from mutation of a gene of interest, or that results from mutation of a gene that has not been previously identified or known to be correlated to the phenotype. The mutant cells produced by these methods of the invention also can be cloned.

Library Screening

Libraries of mutant cells can be screened for mutation of a desired gene. Gene expression levels or gene product activity could be assayed or another phenotype that is associated specifically with the desired gene could be assayed. The assays can be used to identify cells with reduced or missing gene expression or function or with increased or restored gene expression or function. The tag is still useful in this embodiment. It can be used to verify that the mutation is in the desired gene or to ascertain if the desired gene is improperly expressed because of a mutation in a separate gene. The tag could also be useful as a way to isolate the mutated cell or clone of cells from a large number of cells when there is no assay that is sufficiently sensitive.

Examples of useful assays to detect a desired gene include, but are not limited to, ELISA, ELISA spot assays, PCR (e.g., rtPCR), transcription reporter assays, western blot, northern blots, Southern blots, electrophoretic mobility shift assays, transcriptional profiling (e.g., using gene chips), enzyme assays (e.g., protease, kinase, phosphatase, hydrolase, and other known assays), ligand binding assays, and Fluorescence Activated Cell Sorting (FACS®) and magnetic bead cell sorting.

Libraries of mutant cells produced by the present invention can also be screened for desired phenotypes. Cells displaying the desired phenotype can then be used to identify one or more mutant genes responsible for the phenotype where the mutagenic polynucleotide comprises a tag that tags the mutated gene. This approach can be used, for example, to identify mutant genes that play a role in a cellular or biochemical process. By such methods of the invention, changes in a variety of cellular phenotypes that may be associated with genetic mutations may be analyzed, including without limitation: cell proliferation, cell transformation, cell migration, cell differentiation, signal transduction, cell morphology, cell transport, protein degradation, apoptosis, chemoresistance, chemosensitivity, inflammatory response, nuclear translocation of proteins, protein secretion, cellular activation, gene activation, protein expression, receptor activation, and metastasis. See also the previous list above. Many other assays are known in the art that the ordinarily skilled artisan would recognize as useful in the present invention.

The methods of the present invention can also be used in screens for the presence of conditional mutations in cells or organisms. Conditional mutations allow a mutation in a given gene to remain silent until a phenotypic screen (often dependent upon expression of the gene) is performed. This approach is particularly advantageous in situations where, for example, a mutation is toxic to the host cell, creates a slow-growth or no-growth phenotype, kills the cell, induces terminal differentiation, or is otherwise deleterious to the cell. Examples of such conditional mutations that may be used in accordance with, or that may be detected by, the methods of the present invention include but are not limited to temperature sensitive mutations (heat- or cold-sensitive mutations), sensitivity to chemicals such as dimethylsulfoxide, site-specific recombination in vitro or in vivo, translation read-through, and the like.

Uses of Mutated Cells

Once a cell with a desired phenotype is identified, the mutated gene can be identified via the tag present on its protein or mRNA or by analyzing the genomic integration site of the insertional mutagen, as discussed below. Methods for isolating the tagged gene include, but are not limited to, 5' RACE, inverse PCR, and cDNA library construction and hybridization. Methods for cloning genes that have been mutated or activated are known in the art (see, for example, Harrington et al., U.S. patent application Ser. No. 09/276,820 filed Mar. 26, 1999; Zambrowicz et al., U.S. Pat. No. 6,080,576; Sands et al., U.S. Pat. No. 6,136,566; Niwa et al., *J. Biochem.* 113:343-349 (1993); Yoshida et al., *Transgenic Research* 4:277-287 (1995); Baker et al., *Dev. Biol.* 185:201-214 (1997); each incorporated herein by reference for teaching methods of identifying genes mutated by the mutagenic polynucleotides).

The present invention can also be used to discover novel drugs and drug targets for use in diagnosing, treating or preventing a variety of diseases and physical disorders. For example, cDNA molecules and genomic fragments containing mutated genes of interest can be used to produce a gene product in vitro or in a cell or animal, to screen drugs, develop new diagnostic methods or assays related to the genotype or phenotype of interest, or to express proteins for therapeutic use (e.g., the gene may encode a protein such as erythropoietin, that can be administered to patients to treat a condition). The mutant gene or gene product also can be used to identify the corresponding wild-type gene or gene product. The wild-type gene can be used to produce a wild-type gene product in vitro or in a cell or animal, to screen drugs, to develop new diagnostic methods or assays related to the genotype or phenotype of interest, or to express proteins for therapeutic use (e.g., the gene may encode a protein such as erythropoietin that can be administered to patients to treat a condition).

Mutated cells made using the present invention can be used in drug screening. For example, mutated cells displaying a therapeutically relevant genotype or phenotype can be isolated from a library of mutated cells. Once isolated, the mutated cells can be exposed to test compounds to identify compounds that inhibit, further stimulate, or otherwise modulate the genotype or phenotype of interest. By carrying out this process, drugs and/or drug leads can be identified. Examples of phenotypes relevant to drug screening include, but are not limited to, apoptosis, cell proliferation, chemosensitivity, chemotherapeutic resistance, cell migration, cell activation (e.g., T cell activation), cell transformation, metastasis, cellular differentiation, signal transduction, transcriptional activation, protein expression, protein degradation, protein secretion, and other phenotypes known in the art that will be readily apparent to the ordinarily skilled artisan.

Mutated cells prepared according to the present invention can also be used for manufacturing or other commercial purposes. For example, cells of the invention displaying high growth rates, high protein expression levels, high levels of protein secretion, optimized post-translational modification of expressed proteins, ability to grow in serum-free or other defined or inexpensive culture media, etc., offer an advantage in commercial applications such as in manufacturing proteins, foods, beverages, therapeutics, etc.

Mutated cells prepared according to the methods of the present invention can also be used to study gene function in vivo. In one embodiment, cells mutated by the present invention are introduced into an animal by adoptive transfer. Cells displaying a desired phenotype in the animal can then be recovered and isolated. Alternatively, mutated cells that display a desired phenotype in culture can be introduced into an animal by adoptive transfer to study the in vivo phenotype of the cell. Examples of in vivo assays include, but are not limited to, tumor formation, metastasis, graft versus host disease, autoimmune disease, transplant rejection, reconstitution of missing or non-functional cell types (e.g., bone marrow transplantation), cell differentiation, and other assays known in the art. Methods for introducing cells into an animal by adoptive transfer are well known in the art (see, for example, Roth et al., *J. Exp Biol.* 200:2057-2062 (1997); Mosier *Adv Immunol.* 50:303-325 (1991); Mule et al., *J. Immunother.* 12:196-198 (1992); each incorporated herein by reference for teaching methods and uses of adoptive transfer). Optionally, the mutated gene can be identified from the mutated cell.

In another embodiment, mutated cells (e.g., somatic or germ cells, embryonic stem cells or adult multipotential stem cells) can be used to create a transgenic animal. Methods for making transgenic animals from embryonic stem cells are well known in the art (see for example, Jackson and Abbott (2000) Mouse Genetics and Transgenics, Oxford University Press, pgs. 266-284; and Hogan, Beddington, Costantim, and Lacy (1994) Manipulating the Mouse Embryo, Cold Spring Harbor Press, all pages; Joyner, *Bioessays* 13:649-656 (1991); each reference incorporated herein by reference for teaching methods of producing transgenic animals from stem cells). Similarly, methods for making transgenic animals from somatic or germ cells are well known in the art (see, e.g., U.S. Pat. Nos. 5,322,775, 5,366,894, 5,476,995, 5,650,503 and 5,861,299, all of which are incorporated herein by reference in their entireties for teaching methods of producing transgenic animals from mutated or genetically manipulated somatic or germ cells). One such method is nuclear transfer cloning, in which the nucleus of a donor somatic cell is genetically modified (e.g., using the mutational methods of the present invention), and then the nucleus is removed from the donor cell and placed into a recipient cell (preferably, an oocyte) to produce a transgenic animal containing the genetic modifications from the donor nucleus. This process is well-known in the art and will be familiar to the ordinarily skilled artisan (see, e.g., Campbell et al., *Nature* 380:64-66 (1996); Cibelli et al., *Nature Biotech.* 16:620-621 (1998); McCreath et al., *Nature* 405:1066-1069 (2000); Hochedlinger et al., *Nature* 415:1035-1038 (2002); Schnieke et al., *Science* 278:2130-2133 (1997); Kasinathan et al., *Nature Biotech.* 19:1176-1178 (2001); Wolf et al., *Arch. Med. Res.* 32:609-613 (2001); the disclosures of all of which are incorporated herein by reference in their entireties).

In one embodiment, transgenic animals that contain an insertional mutagen that is associated with a specific mutated gene can be prepared by, for example, physicochemically or insertionally mutating sperm cells in vivo and physicochemically or insertionally mutating oocytes in vitro or in vivo (e.g., one or more lentiviral vectors), and then fertilizing the mutated oocytes with the mutated sperm cells to produce a homozygous mutant zygote. This zygote can then be implanted into a recipient female and carried to term, thereby producing a transgenic animal homozygous for one or more mutations. Other methods for producing transgenic animals are well-known in the art, and will be familiar to the ordinarily skilled artisan (see, e.g., WO 90/05188; Hammer, R. E., et al., *J. Animal Sci.* 63:269-278 (1986); Pursel, V. G., et al., *J. Reprod. Fert. Suppl.* 40:235-245 (1995); Houdebine, L. -M., *J. Biotechnol.* 34:269-287 (1994); Hammer, R. E., et al., *Nature* 315:680-683 (1985); Mortensen, R. M., et al., *Mol. Cell. Biol.* 13:2391-2395 (1992); Deng, C., et al., *Cell* 82:675-684 (1995); and Murakami, T., et al., *Devel. Gen.* 10:393-401 (1989), the disclosures of all of which are incorporated herein by reference in their entireties).

Transgenic animals can be created in any eukaryotic organism. In preferred embodiments, the transgenic organism is a fly, a worm, a fish, or a mammal. In highly preferred embodiments, the organism is a human, a non-human primate, a mouse, a rat, a pig, a cow, a sheep, a dog, a cat, a bird, a zebrafish, *C. elegans*, or *Drosophila*. The transgenic animal can be used to carry out genetic screens for phenotypes of interest or for studying the function of individual genes. Examples of phenotypes include, but are not limited to, weight, height/length, organ histology, organ function, immune competency, blood chemistry (e.g., cholesterol levels, etc.), bone density and structure, gross morphology, and behavior. Additional phenotypic screens are known in the art and useful in the present invention (see for example Nolan et al., *Nature Genetics* 25:440-443 (2000); incorporated herein by reference for teaching phenotypic screens).

In another embodiment, multicellular organisms can be mutated directly by in vivo mutagenesis. An animal can be produced from a cell that is mutated in vitro. Mutagenesis can be physicochemical or insertional. The cell can be a stem cell (embryonic or adult), somatic cell, or germ cell. The mutation that is introduced into the animal this way could be a heterozygous mutation in a gene where a homozygous mutation is necessary to produce a phenotype in an organism or in a cell in an organism. The organism can be mutagenized directly to produce the homozygous mutation. A gene responsible for the phenotype can be identified by a tag in the cell used to make the animal or in a cell insertionally mutagenized in the intact animal. The mutation that is introduced may be part of a set of mutations (i.e., mutation in two or more different genes) that are all required to produce a phenotype in an organism or in a cell in an organism. The organism can be mutagenized directly to produce the other required mutations.

Alternatively, transgenic plants can also be produced according to the methods of the present invention. In such methods, one or more, or suitably two or more, genes or alleles in a plant cell is mutated according to the methods of the invention. Transgenic plants may then be prepared using this mutated genomic DNA according to art-known plant genetic engineering techniques, such as nuclear transfer, transformation or protoplast fusion (see Hall, Robert D., *Plant Cell Culture Protocols*, Humana Press, New Jersey (1999); Gartland and Davey, *Agrobacterium Protocols*, Humana Press, New Jersey (1995); Kosuge et al., *Gen. Eng. of Plants* 26:5-25 (1983); Rogers et al., in: *Methods for Plant Molecular Biology*, A. Weissbach and H. Weissbach, eds., Academic Press, Inc., San Diego, Calif. (1988)). Such techniques are widely in use (see, e.g., Chaleff, R. S., *Genetics of Higher Plants: Applications of Cell Culture*, Cambridge: Cambridge University Press (1981)), and newly inserted foreign genes have been shown to be stably maintained during plant regeneration and are transmitted to progeny as typical Mendelian traits (Horsch et al., *Science* 223:496 (1984), and DeBlock et al., *EMBO* 3:1681 (1984)). These foreign genes retain their normal tissue specific and developmental expression patterns. The *Agrobacterium tumefaciens*-mediated transformation system has also proved to be efficient for transfer of genetic material, including many dicotyledonous plant species (Barton et al., *Cell* 32:1033(1983); Chang et al., *Planta* 5:551-558 (1994)) and monocotyledonous plants, e.g., in plants in the Liliaceae and Amaryllidaceae families (Hooykaas-Van Slogteren et al., *Nature* 311:763-764 (1984)) and in *Dioscorea bulbifera* (yam) (Schafer et al., *Nature* 327:529-532 (1987)).

Identification of Conditional Mutations

Conditional mutations that produce phenotypes only after imposing specific experimentally controlled conditions can also be generated using the procedures described in this application. These conditional mutations can be useful in enabling more detailed investigation of gene function and access to a wider range of phenotypes that become possible as a consequence of the inherent ability to precisely control the timing and degree of function of conditionally mutant gene products. Examples of conditional mutations include the creation of cold or heat sensitive mutant cells or organisms that exhibit the loss of mutant gene function and the consequent appearance of mutant phenotypes only under conditions of depressed or elevated temperature, respectively (references 1-6), or the creation of chemically destabilized alleles that depend upon, for example, DMSO exposure, to uncover the altered function of the mutant alleles (reference 7).

The examples described above identify alleles that are conditional upon changes in the environment of the cell or organism. Other alleles that are conditional upon changes that are intrinsic to the mutated cell can also be identified. In this embodiment, experimentally controlled changes in the activity of components of the cell or organism would alter the function of conditionally mutant gene products, and this regulation of mutant gene function would serve to also regulate the appearance of the mutant phenotype. For example, Hsp90 and other chaperonin proteins have been shown to be required to maintain the active conformation of many marginally stable proteins including proteins that contain destabilizing sequence changes as a result of mutation (reference 8-11). Engineering cells to express Hsp90 only under the regulation of an inducible promoter (for example by using tetracycline, ecdysone, or other inducible promoter systems to control Hsp90 gene expression), or treating cells with chemicals that abbrogate Hsp90 function would generate cells in which many mutant proteins could be destabilized and their loss of function phenotypes revealed by experimentally controlled manipulation of Hsp90 activity (references 8-11). Thus the expression of mutant phenotypes would become dependent upon the experimentally induced reduction in Hsp90 or other chaperonin activity. Hsp90 activity might also be manipulated, for example, by creating cells that express their only Hsp90 protein as a fusion protein consisting of a steroid hormone binding (or other regulatory) domain fused to Hsp90 protein. Such a regulatory domain-chaperonin fusion protein would only exhibit chaperone active when bound with the appropriate steroid hormone (or other regulatory ligand; references 12-15) and conditional mutations and phenotypes would depend upon the concentration of the regulatory ligand in these cells. 1: Tasaka S E, Suzuki D T. Genetics. 1997 July;74(3):509-20; 2: Suzuki D T. Science. 1970 Nov. 13;170 (959):695-706; 3: Suzuki D T, Piternick L K, Hayashi S, Tarasoff M, Baillie D, Erasmus U. Proc Natl Acad Sci USA. 1967 April;57(4):907-12; 4: Pringle J R. Methods Cell Biol. 1975;12:233-72; 5: Basilico C. Adv Cancer Res. 1977;24: 223-66; 6: Meiss H K, Talavera A, Nishimoto T. Somatic Cell Genet. 1978 January;4(l):125-30; 7: Poloni D, Simanis V. FEBS Lett. 2002 Jan. 30;511(1-3):85-9; 8: Morimoto R I, Kline M P, Bimston D N, Cotto J J. Biochem. 1997 32: 17-29; 9: Jakob U, Lilie H, Meyer I, Buchner J. J. Biol. Chem. 1995 270:7288-94; 10: Rutherford S L, Lindquist S. Nature. 1998 Nov. 26;396(6709):336-42; 11: Queitsch C, Sangster T A, Lindquist S. Nature. 2002 Jun. 6;417(6889):618-24; 12: Angrand P O, Woodroofe C P, Buchholz F, Stewart A F. Nucleic Acids Res. 1998 Jul. 1;26(13):3263-9; 13: Tada M, O'Reilly M A, Smith J C. Development. 1997 June;124(11): 2225-34; 14: Takebayashi H, Oida H, Fujisawa K, Yamaguchi M, Hikida T, Fukumoto M, Narumiya S, Kakizuka A. Cancer Res. 1996 Sep. 15;56(18):4164-70; 15: Metzger D, Clifford J, Chiba H, Chambon P. Proc Natl Acad Sci USA. 19995 Jul. 18;92(15):6991-5.

It will be understood by one of ordinary skill in the relevant arts that other suitable modifications and adaptations to the methods, compositions and applications described herein are readily apparent from the description of the invention contained herein in view of information known to the ordinarily skilled artisan, and can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Combined Mutagenesis of Embryonic Stem Cells

Embryonic stem cells (RI) (Nagy et al., *Proc. Natl. Acad. Sci. USA* 90:8424-8428 (1990)) are cultured on feeder cells or gelatin coated plates at 37EC in a humidified incubator with 7.5% $CO_2$. The cells are cultured in D-MEM/15% FBS/0.1 mM β-mercaptoethanol/Leukemia Inhibitory Factor (1000 U/ml)/non-essential amino acids. The cells are grown to 80% confluence. In 10 plates, each containing approximately $4 \times 10^6$ cells, $O^6$-benzylguanine ($O^6$-BG) is diluted in DMSO and added to the media to 10 µM final concentration. To a separate 10 plates, no $O^6$-BG is added. Following a 12-16 hour incubation, cells from each plates are trypsinized, diluted to $5 \times 10^6$ cells/ml, and incubated with various concentrations of ENU for 1 or 2 hours. ENU concentrations were 0.2 mg/ml, 0.3 mg/ml, 0.35 mg/ml, and 0.4 mg/ml. The cells that are pretreated with $O^6$-BG were incubated with $O^6$-BG during the ENU treatment. Following treatment, cells from each ENU treatment are washed, trypsinized to dissociate aggregates, counted, and plated in duplicate into gelatin coated tissue culture plates at between 100, 1000, 10,000, and 100,000, cells per plate and grown under standard conditions described above. The $O^6$-BG treated cells are grown in the presence of $O^6$-BG (10 µM) for 24 hours, followed by growth in standard media. Colonies are counted after 10 days. In the duplicate plates, 6-thioguanine (6-TG) is added at 48 hours post-plating to select for HPRT-null mutations in order to determine the mutation frequency produced by each treatment condition. The number of 6-TG resistant colonies divided by the number of colonies present on the duplicate (non-6TG selected) plate determines the mutation frequency for a single copy gene.

In an example of the methods of the invention, a plate containing approximately 1000 clones is selected from an ENU/$O^6$-BG treatment condition that give a mutation frequency of 1 in 1000. The cells are expanded to $5 \times 10^9$ cells (50% confluence) under standard culture conditions described above. The cells are then washed and incubated with pKO-1 retroviral vector at an MOI=1 for 24 hours. The structure of pKO-1 is shown in FIG. 3B. After 24 hours, the cells are washed and replated in duplicate into fresh media at 10% confluence. One of the duplicate libraries is grown to 40-50% confluence and placed tinder G418 selection (250 µg/ml). The other duplicate library is grown to confluence, trypsinized, frozen in 90% FBS/10% DMSO at $10^7$ cells/ml, and stored in liquid nitrogen. Cells grown under G-418 selection are grown, without replating, for 10-12 days with several media changes. G418 resistant clones are counted, trypsinized, and expanded. The library can then be stored in liquid nitrogen or used for phenotypic screening.

Example 2

Combined Mutagenesis of Jurkat Cells

Cellular Screen to Identify Gene Knockouts that cause Resistance to FasL-Induced Apoptosis in Jurkat Cells The combined mutagenesis technology described in this application was developed to speed the discovery of gene function in mammalian cell culture by coupling distinct mutagenesis techniques to efficiently generate phenotypes and simultaneously enable the facile identification of gene mutations that cause these phenotypes, combined mutagenesis combines the strengths of various mutagenic approaches to compensate for distinct deficiencies of each of the individual mutagenesis techniques. The embodiment of combined mutagenesis that is described here uses the following sequence of steps to identify cell based gene function (illustrated in FIG. 1):

high density ENU mutagenesis of cells in culture; creates compact libraries of cells that contain mutations in nearly all genes select only those ENU mutagenized clones for further gene trap mutagenesis that do not already display the phenotype gene trap mutagenesis of selected ENU clones selection for gene trap mutagenized clones that now display the phenotype test to ensure the phenotype reverts to wild type upon Cre-mediated removal of the gene trap sequence identification of the insertionally mutated gene in Cre-revertible gene trap clones siRNA confirmation that specific gene knockouts are sufficient to confer phenotype Efficient creation of phenotypes and identification of mutated genes derives from combining the high efficiency of chemical mutagenesis with the ability of gene trap insertional mutagens to provide a sequence tag for identification of the mutated genes (FIG. 15). Chemical mutagens are highly efficient means to generate high densities of mutations in mammalian cells, and the size of libraries that contain mutations in all genes can be less than 50 cells. However, the identification of the alleles that cause specific phenotypes in these chemically mutated cell lines is extremely difficult. In contrast, while mutagenesis by gene trap vectors is much less efficient, these gene trap mutagens compensate by enabling the easy identification of the genes that are responsible for a given phenotype by means of the physical linkage between the mutagenized gene and sequences in the insertional mutagen. Cells showing phenotypes created by combined mutagenesis carry at least one chemically induced mutation and at least one gene trap mutation whose mutual interaction is needed to generate the cellular phenotype (FIG. 15).

To test the combined mutagenesis technology we needed to 1) establish a high density chemical mutagenesis protocol, 2) construct an effective and reversible gene trap retrovirus, 3) create a combined mutagenesis mutagenized library with these reagents, and 4) conduct a proof-of-principle screen of this library to identify cells that have acquired resistance to Fas-induced apoptosis as a result of the combined mutagenesis. The development and testing of combined mutagenesis is described below.

The ability to identify all genetic mutations that can create a phenotype requires that large numbers of mutations be created in as few cells as possible, and the high efficiency of ENU chemical mutagenesis is suited to this task. We set out to determine the ENU treatment needed to create 50-100 cell libraries in which all genes are mutated at least once (defined as a 1×knockout library) in Jurkat cells. To characterize the mutagenesis we measured both cell survival and the mutation rate in characterizing the optimal ENU treatment (Table I). Survival was determined by limiting dilution, and the mutation rate was estimated in the population of surviving clones based on the frequency of knocking out the single copy HPRT gene (assayed by the survival of such HPRT$^-$ cells upon culture in the presence of 6-thioguanine). As shown in the table below, at an ENU dose of 0.2 mg/ml the mutation rate is 0.02 HPRT$^-$ genes/cell and the 1×library size is therefore ~50 cells. Creation of libraries of these densely mutagenized cells provides a genetically sensitized background in which small increments of further mutagenesis can create phenotypes by knocking out the sole remaining wild type alleles of ENU-mutated genes.

TABLE I

| ENU dose (mg/ml) | % survival | mutation rate | 1× library size* |
|---|---|---|---|
| 0 | 98.40% | $3.9 \times 10^{-7}$ | $2.56 \times 10^6$ |
| 0.1 | 1.83% | $2.4 \times 10^{-3}$ | 417 |
| 0.125 | 0.93% | $4.9 \times 10^{-3}$ | 204 |
| 0.15 | 1.08% | $6.1 \times 10^{-3}$ | 164 |
| 0.175 | 0.88% | $8.2 \times 10^{-3}$ | 122 |
| 0.2 | 0.29% | $2.0 \times 10^{-2}$ | 50 |
| 0.25 | 0.07% | $3.3 \times 10^{-2}$ | 31 |
| 0.45 | $7 \times 10^{-5}$ | NA | NA |

*"1× library size" refers to the number of ENU treated clones needed to contain mutations. Chemical mutagenesis protocol: Jurkat cells were treated with 10 uM O-6-BG (Sigma) at $5 \times 10^5$ cells/ml for 16 hours at 37° C. in a humidified incubator with 5% CO2. The pretreated cells were then incubated with desired concentration of ENU (Sigma) in the presence of O-6-BG for 2 hours at 37° C. with constant shaking. At the end of incubation cells were washed with 10-volume 1 × PBS three times and resuspended in complete media with 10 uM O-6-BG. 24 hours later O-6-BG was washed off, cells were resuspended in complete media and seeded onto 96-well plate at 20 cells per well or 400-2000 cells per well. Cells were then cultured for 10 days. Viability is determined by the lower density seeding based on number of wells containing growing colonies. To determine mutation frequency, cells seeded at the higher density were used to select for Hprt-loss of function mutants in the presence of 40 uM 6-TG (Sigma). Number of wells containing growing colonies in the presence of 6-TG was scored 7-10 days later. Mutation frequency is calculated as # of 6-TG resistant colony divided by # of viable cells seeded.

Similarly mutated libraries were created by treating Jurkat cells with 0.7 mg/ml EMS (Sigma) following above protocol A. 1× library size about 100 cells under this condition.

Karyotype of ENU Mutagenized Jurkat Cells:

In some preferred embodiments, cells subjected to mutation are diploid. Therefore we determined the chromosome count of Jurkat cells and ENU mutagenized Jurkat cells by Giemsa stain. ~75% of ENU mutagenized Jurkat cells are diploid or hypodiploid. This is comparable with wild type Jurkat cells.

In order to prepare the ENU libraries for gene trap mutagenesis, the surviving Jurkat clones were then tested to ensure that they remained susceptible to FasL induced apoptosis after the 0.2 mg/ml ENU mutagenesis; 100 of these Fas-sensitive clones were then chosen as targets for gene trap mutagenesis. This exercise demonstrates that we can create densely mutagenized libraries of cells that do not exhibit the phenotype of interest even though they contain knockouts in one copy of 1-3% of the genes in each cell. This combination of dense mutagenesis with lack of phenotype is crucial since it creates small and tractable libraries of cells that possess genetic backgrounds in which single gene trap knockouts can create a phenotype by disrupting the remaining wild type copy of genes that determine phenotype.

Creation of an efficient gene trap vector was needed to serve as an insertional knockout mutagen and tag of the insertionally mutated genes for the next phase of combined mutagenesis function discovery. The design of the gene trap retroviral vector pDKO2 that was created for this purpose is shown below (FIG. 16). This vector is designed to trap transcriptional active genes using the function of the splice acceptor in the vector. When the vector is integrated within a gene, splicing occurs from splice donors that exist at the end of exons in the trapped endogenous gene onto the splice acceptor that is provided by the vector. Once this splicing event occurs, a fusion transcript will be made that results in the introduction of vector encoded stop codons that cause the premature termination of the protein product of the trapped gene. Downstream IRES (internal ribosome entry site) activity in the fusion transcript enables the reinitiation of translation on the fusion transcript and this translation expresses a selectable drug resistance protein. Expression of drug resistance allows selection to identify the trapping of transcriptionally active genes. Lox signals flank the gene trap portion of pDKO2, and Cre-mediated recombination of these lox sites results in the deletion of the pDKO2 gene trap and knockout functions; this deletion should revert phenotypes that depend upon insertional mutagenesis and aid in the identification of biologically active gene traps.

The function of the various components of pDKO2 were separately tested to ensure activity as follows:
  IRES: We confirmed that this IRES does function to reinitiate translation, and showed that it does not have promoter activity in pDKO2
  TK: expression of TK was shown to cause cell death in gancyclovir containing media
  Cre/lox: transfection of cre expression plasmids into cells carrying the integrated pDKO2 construct resulted in excision events occurring in ~80% of cells
  S/A-x-IRES-DR-bGHpA: the gene trap portion of pDKO2 was introduced into Jurkat cells, followed by selection for drug resistance (neomvcin 1.5 mg/ml for Jurkat), drug resistant clones were harvested and the appearance of drug resistance was associated with splicing of endogenous transcripts onto the pDKO2 splice acceptor in all cases examined by RT-PCR
  Production of the pDKO2 retroviral vector occurred by transfecting pDKO2 into RetroPack PT67 cells (Clontech) via Exgen500 (MBI Fermentas). Individual stable colonies were picked and selected for high titer producers. High titer virus soup was harvested and used to infect Jurkat cells following spin-infection protocol. Briefly, $3 \times 10^6$ Jurkat cells were resuspended in 2 ml complete media plus 1 ml viral soup and polybrene at 8 ug/ml. We spininfected at 1000 g for 1 hour. Cells were then placed in 32 C. incubator overnight and then incubated at 37C for 24 hours to allow integration and expression of retrovirus. Titer was determined by limiting dilution and found to be $1-3 \times 10^4$ per ml.

To assess gene trap efficiency of this vector, we assayed the frequency of gene trap events for several known genes by RT-PCR. Two pairs of nested gene specific primers (specific for DHFR, HPRT, FasR, and Casp8) were used in this analysis, and the resultant RT-PCR products were sequenced to confirm the identity of gene traps. All were confirmed to be true gene trap events with upstream exons from the endogenous gene correctly spliced onto the splice acceptor in pDKO2. In most cases pDKO2 was found to integrate within introns near the 5'-end of the trapped gene. The data shown below suggest that the 1×library size for trapping a single allele is $\sim 2 \times 10^4$ clones. It is easy to generate this number of clones, and this efficiency permits the use of pDKO2 to create genome wide gene trap knockout libraries in each of the Fas-sensitive ENU clones described above.

Gene Trap Frequency:

| Cell type | # clones per pool | # pools total | # clones total | # of pools in which one of the following genes is trapped | | | |
|---|---|---|---|---|---|---|---|
| | | | | HPRT | DHFR | FasR | Casp8 |
| Jurkat | 7500 | 10 | $7.5 \times 10^4$ | 2 | 3 | 3 | 9 |

Characterization of Trapped Genes:

| gene name | HPRT | DHFR | FasR | Casp8 |
|---|---|---|---|---|
| # traps | 2 | 3 | 3 | 9 |
| # alleles/cell | 1 | 2 | 2 | 2 |
| gene size | 40 kb | 30 kb | 26 kb | 55 kb |

For 75,000 clones
(2+3+3+9)/(1+2+2+2)=2.4 hits per allele
for a diploid gene: 4.8 hits per 75,000 clones
average size for assayed genes: (40+30+26+55)/4=38 kb
for average gene size of 28 kb, 1×library size: $2 \times 10^4$ The next step is to combine these elements to implement a combined mutagenesis screen to identify gene functions. Clones from the ENU Jurkat library were infected with the pDKO2 gene trap retrovirus to create a combined mutagenesis knockout library in Jurkat cells (FIG. 17). One hundred ENU mutagenized Jurkat clones (2×genome coverage for ENU mutagen) that had been tested to ensure unchanged sensitivity to Fas-induced apoptosis were chosen for this pDKO2 retrovirus infection and ~$10^4$ drug resistant clones (0.5×genome coverage for pDKO2 mutagen) were obtained for each ENU clone. The final combined mutagenesis library therefore consists of ~one million clones and this number represents ~1×coverage of the range of possible human gene disruptions in these cells. This coverage is sufficient to identify the majority (but not all) of the mutations that decrease FasL induced apoptosis in Jurkat cells. Under above conditions, the spontaneous Fas resistance rate is ~1 in $2$-$3 \times 10^6$ 2. Mutation Screen:

ENU clones were first tested for FasAb sensitivity. Only Fas-sensitive clones were carried forward for the screen. 100 ENU clones (derived from 0.2 mg/ml ENU treatment, table A.1.) were expanded (~2×library coverage) to 5-10×106 cells per clone. Each ENU clone was infected with pDKO2-neo retrovirus to create a pool of cells where one allele of a gene can be potentially mutated by the pDKO2 vector. About 104 drug resistant clones were obtained for each ENU clone, which is about 0.5×library coverage for gene trap event. Cells were split into duplicate, A and B, immediately after infection and were subsequently grown in neomycin containing media for 10-12 days to select for neomycin resistant clones and to deplete endogenous wild type protein produced prior to the mutation of the gene. From each pool A or B, 0.5-1×106 cells (100-200 cells per clone) were taken into Fas screen following protocol in C1. Fas resistant clones were identified by the outgrowth of the cells during the first 2-3 weeks after Fas treatment.

Fas resistant clones were subjected to re-test by Annexin V staining (Molecular Probes) and caspase 3 activity assay (Intergen) (Ref: Blood 84, 1415, 1994; J. Biol. Chem. 273, 32608-32613, 1998). ~70% of the clones confirm the Fas resistant phenotype based on these two assays. To determine if the resistant phenotype is due to insertion of the pDKO2 vector into the genome, cre expression plasmid was transfected into each clone and followed by gancyclovir selection to select for excision event. Clones were then analyzed for reversion of the phenotype, thereby demonstrating that the trapped gene was responsible for the phenotype.

FasL induced apoptosis is well studied in Jurkat cells, and modulators of this pathway have potential clinical relevance in cancer, stroke and other disease processes. Previous genetic and biochemical analysis many systems and laboratories have established the basic signal transduction path involved in initiating FasL induced apoptosis (FIG. 18). We expect to identify combined mutagenesis gene trap knockouts of some of the members of the known Fas signaling pathway (FIG. 18) as one result of this screen. Knockout of novel genes might also reveal previously unknown players important for regulating apoptosis, and these novel regulatory genes are of great interest as potential new targets for therapeutic intervention.

To identify gene traps that affect sensitivity to FasL, the doubly mutagenized combined mutagenesis library was selected for clones that exhibited resistance to Fas-induced apoptosis. Under the FasL selection conditions, there is a low spontaneous background of resistance that occurs at ~1 in $2$-$3 \times 10^6$ cells, and we recovered 35 Fas-resistant clones from the million clone library. The phenotype of each clone was further confirmed by showing that FasL treatment failed to activate the normal levels of Annexin V staining and Caspase 3 activity as molecular markers of apoptosis. These results show that combined mutagenesis can efficiently create reproducible phenotypes in mammalian cells.

To determine which of the FasL-resistant cells have acquired their phenotype as a direct result of the insertion of the pDKO2 vector into the genome, we used transfection of Cre expression plasmids to induce the excision of pDKO2 gene trap sequences from each of the clones. Cre mediated recombination was followed by gancyclovir selection to detect deletion of the thymidine kinase element along with the gene trap functions in pDKO2. Clones were then analyzed for reversion of the phenotype, and 13 out of the 35 clones showed phenotypic reversion after Cre-mediated removal of the gene trap (phenotypic reversion data shown in FIG. 19). The cells that did not show phenotypic reversion after excision of the gene trap may have acquired resistance to FasL as the result of a spontaneous mutation, but since such events are nearly impossible to identify, these clones were not analyzed further. Thirteen clones did show FasL resistance that depended upon gene trap knockout, and these cells were further studied to identify the trapped genes and to characterize their role in apoptosis.

The 13 clones showing FasL resistance caused by the pDKO2 gene trap were analyzed using RT-PCR, 5'-RACE and inverse PCR to identify the biologically active trapped genes. It has been demonstrated previously that mutation of caspase-8 gene leads to FasL resistance (Curr. Biol. 8(18), 1001-1008, 1998). To test whether caspase-8 has been mutated in any of the FasL resistant clones from our screen, we carried out RT-PCR assay with two nested caspase-8 specific forward primers and two nested vector specific reverse primers on those clones. We identified caspase-8 trap in 2 of the clones. 5'-RACE and inverse PCR identified the trapped genes in most of the other Fas-resistant clones. Many of these genes had not been previously characterized as having an involvement in FasL induced apoptosis, and these genes are expected to play unexpected roles in apoptosis and as potential therapeutic targets.

In summary, we have developed a loss of function genetics strategy that enables the discovery of in vivo gene function in mammalian cells, and have shown that this combined mutagenesis strategy permits the rapid identification of known and novel genes that perform these functions. Such a genetic approach should be valuable in the identification of gene function and in the discovery of new targets for therapeutic intervention.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A cell library comprising physicochemically mutated clones, wherein the mutation frequency of physicochemically mutated alleles is 1× genome coverage per $2-10^3$ physicochemically mutated clones, and wherein one or more of said physicochemically mutated clones contains one or more insertional mutagens, wherein said insertional mutagen comprises a polynucleotide.

2. The cell library of claim 1 wherein the mutation frequency of physicochemically mutated alleles is 1× genome coverage per 50-100 clones.

3. The cell library of claim 1 wherein the mutation frequency of physicochemically mutated alleles is 1× genome coverage per 30-400 clones.

4. The cell library of claim 1 wherein the mutation frequency of physicochemically mutated alleles is 1× genome coverage per 2, 5, 10, 25, 50, 100, 200, 400, 600 or 800 clones.

5. The cell library comprising physicochemically mutated clones, wherein the average number of physicochemically mutated alleles per cell is 10-100, 250-5,000, 50-10,000 or 10,000-50,000, and wherein one or more of said physicochemically mutated clones contains one or more insertional mutagens.

6. A method for making a mutagenized cell library, said method comprising insertionally mutagenizing a cell library, said library comprising physicochemically mutated clones, wherein the mutation frequency of physicochemicalty mutated alleles is 1× genome coverage per 2-103 physicochemically mutated clones, and wherein said insertional mutagen comprises a polynucleotide.

---

SEQUENCE LISTING

<160> NUMBER OF SEQ ID NOS: 2

<210> SEQ ID NO 1
<211> LENGTH: 14
<212> TYPE: DNA
<213> ORGANISM: Homo Sapiens
<220> FEATURE:
<221> NAME/KEY: misc_feature
<222> LOCATION: 1-10, 12
<223> OTHER INFORMATION: y = C or T
<220> FEATURE:
<221> NAME/KEY: misc_feature
<222> LOCATION: (11).(0)
<223> OTHER INFORMATION: n = A, T, C or G

<400> SEQUENCE: 1
yyyyyyyyyy nyag                                                         14

<210> SEQ ID NO 2
<211> LENGTH: 8
<212> TYPE: DNA
<213> ORGANISM: Homo Sapiens
<220> FEATURE:
<221> NAME/KEY: misc_feature
<222> LOCATION: 1
<223> OTHER INFORMATION: n = a or c
<220> FEATURE:
<221> NAME/KEY: misc_feature
<222> LOCATION: 6
<223> OTHER INFORMATION: r denotes a purine nucleotide

<400> SEQUENCE: 2 naguragu                                                                 8

7. A method for making a mutagenized cell library, said method comprising physicochemically mutagenizing a cell library, said library comprising insertionally mutated clones, wherein the mutation frequency of physicochemically mutated alleles is 1× genome coverage per 2-10³ physicochemically mutated clones, and wherein said insertional mutagen comprises a polynucleotide.

8. The method of claim 6 wherein, in the cell library, the mutation frequency of physicochemically mutated alleles is 1× genome coverage per about 50-100 physicochemically mutated clones.

9. The method of claim 6 wherein, in the cell library, the mutation frequency of physicochemically mutated alleles is 1× genome coverage per 30-400 physicochemically mutated clones.

10. The method of claim 6 wherein, in the cell library, the mutation frequency of physicochemically mutated alleles is 1× genome coverage per 2, 5, 10, 25, 50, 100, 200, 400, 600 or 800 physicochemically mutated clones.

11. The method of any one claims 6-10 wherein, in the cell library, the average number of physicochemically mutated alleles per cell is 10-100, 250-5,000, 50-10,000 or 10,000-50,000.

12. The cell library of claim 1 or 5, wherein the physicochemical mutagen used to create said physicochemically mutated clones is selected from the group consisting of UV irradiation, gamma irradiation, x-rays, a restriction enzyme, a mutagenic or teratogenic chemical, a DNA repair inhibitor, N-ethyl-N-nitrosourea (ENU), ethylmethanesulphonate (EMS) and ICR191.

13. The cell library of claim 1 or 5, wherein said insertional mutagen comprises at least one or more of a stop codon, a splice acceptor site, a selectable marker, and a reporter gene.

14. The cell library of claim 5 or 10, wherein said insertional mutagen is contained within a virus or transposon.

15. The cell library of claim 14 wherein said virus is selected from the group consisting of an adenovirus, an adeno-associated virus, a retrovirus, an alpha-herpesvirus, a lentivirus, a pseudorabies virus and a herpes simplex virus.

* * * * *

UNITED STATES PATENT AND TRADEMARK OFFICE
CERTIFICATE OF CORRECTION

| | | |
|---|---|---|
| PATENT NO. | : 7,972,853 B2 | Page 1 of 1 |
| APPLICATION NO. | : 10/345115 | |
| DATED | : July 5, 2011 | |
| INVENTOR(S) | : John Joseph Harrington et al. | |

It is certified that error appears in the above-identified patent and that said Letters Patent is hereby corrected as shown below:

In the Claims

Column 58, line 27 - Claim 6 reads "physicochemicalty" but should read -- physicochemically --.

Signed and Sealed this

Thirteenth Day of September, 2011

David J. Kappos
*Director of the United States Patent and Trademark Office*